United States Patent [19]
Wilhelm et al.

[11] Patent Number: 5,716,954
[45] Date of Patent: Feb. 10, 1998

[54] BENZOPYRIDAZINONE AND PYRIDOPYRIDAZINONE COMPOUNDS

[75] Inventors: Robert S. Wilhelm, Mountain View; Bradley E. Loe, Santa Cruz; Bruce H. Devens, Palo Alto; Robert Alvarez, Menlo Park; Michael G. Martin, San Francisco, all of Calif.

[73] Assignee: Syntex U.S.A. Inc., Palo Alto, Calif.

[21] Appl. No.: 369,041

[22] Filed: Jan. 5, 1995

Related U.S. Application Data

[63] Continuation of Ser. No. 86,954, Jul. 2, 1993, abandoned, which is a continuation-in-part of Ser. No. 775,679, Oct. 9, 1991, abandoned, and PCT/US92/0398, Oct. 8, 1992.

[51] Int. Cl.$^6$ .................. A61K 31/535; A61K 31/50; C07D 471/04; C07D 237/32
[52] U.S. Cl. ............ 514/234.2; 514/248; 544/117; 544/236; 544/237; 546/322; 546/326; 560/52
[58] Field of Search ................. 544/236, 117; 514/248, 234.2

[56] References Cited

U.S. PATENT DOCUMENTS

| | | |
|---|---|---|
| 4,806,535 | 2/1989 | Faith et al. ................ 514/248 |
| 5,405,826 | 4/1995 | Hewett et al. ............. 504/238 |

FOREIGN PATENT DOCUMENTS

| | | |
|---|---|---|
| 401981 | 12/1990 | European Pat. Off. |
| 407808 | 1/1991 | European Pat. Off. |
| 2708187 | 2/1977 | Germany . |
| 1224 | 11/1991 | South Africa . |
| 00567 | 1/1989 | WIPO . |
| 12251 | 8/1991 | WIPO . |

OTHER PUBLICATIONS

Ohi et al, Chemical Abstracts, vol. 115, No. 256193 (1991) (Abstract for WO 91 12251, Aug. 22, 1991).
Oishi et al, Yakagaku Zasshi, vol. 103, pp. 631–643 (1983).
Nicholson et al, Tips, 12:19–27 (1991).
Beavo et al, Tips, 11:150–155 (1990).
Livi et al, Mol. Cell. Biol. 10:2678–2686 (1990).
Hirshman et al, J. Allergy Clin. Immunol., 79:46–53 (1987).
Holden et al, J. Invest. Dermatol., 87:372–376 (1986).
Glaser et al, Agents and Actions, 15:341–348 (1984).
Alvarez et al, Mol. Pharmacol. 20:302–309 (1981).
Mitsunobu, Reviews, pp. 1–28 (1981).
Thompson et al, J. Biol. Chem. 251: 4922–4929 (1976).
Kenyon et al, J. Chem. Soc., pp. 2531–2536 (1957).
Sandler et al, Organic Functional Group Preparations (2nd Ed.), vol. 1, Chapter 14, pp. 434–465 (1983).
Galvan et al, Naunyn–Schmiedberg's Arch Pharmacol, 342:221–227 (1990).
Csampai et al, Tetrahedron, 45, pp. 5539–5548 (1989).
Ismail et al, Tetrahedron, 40, pp. 2983–2984 (1984).
Johnson et al, J. Org. Chem. 56, pp. 5218–5221 (1991).
Wermuth et al, Chim. Ther., VI, No. 2, pp. 109–115 (1971).
Bansal et al, Chemical Abstracts, vol. 108, No. 131719 (1988).
Afify et al, Chemical Abstracts, vol. 106, No. 156382 (1987).
Bansal et al, Chemical Abstracts, vol. 105, No. 42152 (1986).
Oishi et al, Chemical Abstracts, vol. 100, No. 51532 (1984).
Yakovlev et al, Chemical Abstracts, vol. III, No. 39285 (1989).
Fahmy et al, Chemical Abstracts, vol. 83, No. 178862 (1975).
Epsztajn et al, Monatshefte für Chemie, vol. 121, pp. 909–921 (1990).
Marek, Chemical Abstracts, vol. 80, No. 59626 (1974).
Bhatt et al, J. Org. Chem., vol. 44, pp. 984–989 (1979).
Bowden et al, J. Chem. Soc. (B), pp. 145–148 (1971).
Glossary of Chemical Terms by Hampel and Hawley (2nd Ed.) pp. 12.25 (1982).

Primary Examiner—Emily Bernhardt
Attorney, Agent, or Firm—Heller Ehrman White & McAuliffe

[57] ABSTRACT

Benzo or pyridopyridazinones and pyridazinthiones of the formula

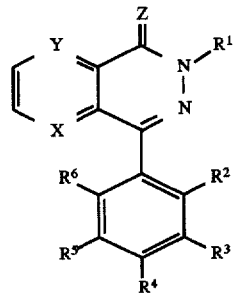

Formula I wherein:

X and Y are nitrogen or carbon, provided that at least one is carbon, and Z is oxygen or sulfur;

$R^1$ is hydrogen, lower alkyl, aryl, aralkyl, heterocyclo, heterocyclo lower-alkyl, heteroaryl, or heteroaralkyl;

$R^2$, $R^3$, $R^4$, $R^5$ and $R^6$ are independently selected from hydrogen, lower alkyl, halo, carboxy, alkoxycarbonyl, carbamoyl, lower-alkyl carbonyl, halocarbonyl, thiomethyl, trifluoromethyl, cyano or nitro;

or a pharmaceutically acceptable ester, ether or salt thereof, have been found to be useful as an anti-inflammatory, antasthmatic, immunosuppressive, anti-allograft rejection, anti-graft-vs-host rejection, autoimmune disease or analgetic agent(s).

45 Claims, No Drawings

BENZOPYRIDAZINONE AND PYRIDOPYRIDAZINONE COMPOUNDS

CROSS-REFERENCE TO RELATED APPLICATIONS

This application is a continuation of application Ser. No. 08/086,954, filed Jul. 2, 1993, abandoned. Application Ser. No. 08/086,954 is a continuation-in-part of application Ser. No. 07/775,679, filed Oct. 9, 1991, abandoned, which is incorporated herein by reference. Application Ser. No. 08/086,954 also claims priority from PCT International Application No. PCT/US92/08398, filed Oct. 8, 1992, incorporated herein by reference and itself claiming priority from application Ser. No. 07/775,679.

BACKGROUND OF THE INVENTION

1. Field of the Invention

This invention relates to benzo and pyridopyridazinones and pyridazinthiones useful as anti-inflammatory agents, antasthmatic agents, immunosuppressive agents, anti-allograft rejection agents, anti-graft-vs-host disease agents, anti-autoimmune agents or analgetic agents, to their intermediates, to their preparation and to pharmaceutical compositions using the compounds of the invention.

2. Background Information

Cyclic 3',5'-adenosine monophosphate (cAMP) modulates a variety of cellular and physiologic functions in mammals, such as cell division, endocrine function, and the immune response. The level of cAMP is controlled, in part, by a class of enzymes called phosphodiesterases, which enzymatically degrade cAMP. There are five families of phosphodiesterase that are categorized according to their function. For instance, phosphodiesterase III (PDE III) is isolated from human platelet cells and modulates platelet aggregation. Another type of phosphodiesterase, (PDE IV), is found in various cells but it is the predominant form in human leukocytes. This enzyme modulates leukocyte activation and function associated with the immune response and inflammation. Both of these phosphodiesterases implement their control by modulating the cellular level of cAMP in their respective cells. Thus, inhibition of phosphodiesterases provides a method of modulating any cellular and bodily function that is controlled by cAMP.

Compounds that are nonspecific phosphodiesterase inhibitors are known, i.e., these compounds inhibit all or multiple types of phosphodiesterases. [See, Beavo, J. A. and D. H. Reifsyder, *Trends in Pharm. Science*, 11:150–155 (1990); and Nicholson, C. D., R. A. J. Challiss and M. Shahid, *Trends in Pharm. Science*, 12:19–27 (1991).]

Nonspecific phosphodiesterase inhibitors are of limited value because of numerous side-effects. Since cAMP is involved in so many functions throughout the body, a nonspecific phosphodiesterase inhibitor has the potential to alter all of the functions modulated by cAMP.

It has been surprisingly discovered that certain benzo and pyridopyridazinones are potent selective inhibitors of phosphodiesterase IV (PDE IV). These compounds are well suited for use as a treatment for any disorder in which PDE IV function plays a role, such as where leukocyte activation or function is involved. In particular, these compounds are especially well suited for use as anti-inflammatory agents, antasthmatic agents, immunosuppressive agents, anti-allograft rejection agents, anti-graft-vs-host disease agents or anti-autoimmune disease agents.

SUMMARY OF THE INVENTION

One aspect of the present invention relates to benzo or pyridopyridazinones and pyridazinthiones, i.e., the compounds of Formula I:

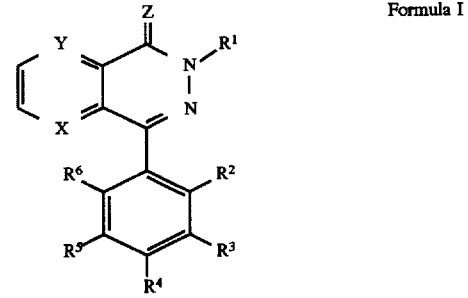

Formula I wherein:

X and Y are nitrogen or carbon, provided that at least one is carbon, and Z is oxygen or sulfur;

$R^1$ is hydrogen, lower alkyl, cycloalkyl, cycloalkyl lower alkyl aryl, aralkyl, heterocyclo, heterocyclo lower-alkyl, heteroaryl, or heteroaralkyl;

$R^2$, $R^3$, $R^4$, $R^5$ and $R^6$ are independently selected from hydrogen, lower alkyl, halo, carboxy, alkoxycarbonyl, carbamoyl, lower-alkyl carbonyl, halocarbonyl, thiomethyl, trifluoromethyl, cyano or nitro; or a pharmaceutically acceptable ester, ether or salt thereof.

In another aspect, the invention relates to a pharmaceutical composition containing a therapeutically effective amount of a compound of Formula I or a pharmaceutically acceptable ester or salt thereof admixed with at least one pharmaceutically acceptable excipient.

In still another aspect, the invention relates to a method of use as an anti-inflammatory, antasthmatic, immunosuppressive, anti-allograft rejection, anti-graft-vs-host rejection, autoimmune disease, or analgetic agent, by administering to a mammal in need of such treatment a therapeutically effective amount of a compound of Formula I or a pharmaceutically acceptable ester or salt thereof.

Yet another aspect of the invention relates to the treatment of the above conditions or diseases by the selective inhibition of phosphodiesterase (PDE) IV.

Yet another aspect of the invention relates to precursors for making the compounds of Formula I and the pharmaceutically acceptable salts and esters thereof, represented by Formula II:

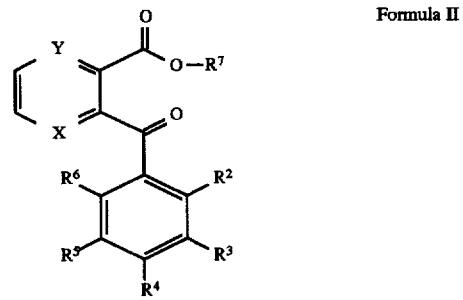

Formula II wherein:

X and Y are nitrogen or carbon atoms, provided that at least one is carbon;

$R^2$, $R^3$, $R^5$ and $R^6$ are independently selected from hydrogen, lower alkyl, halo, carboxy, alkoxycarbonyl, carbamoyl, lower-alkyl carbonyl, halocarbonyl, thiomethyl, trifluoromethyl, cyano or nitro;

$R^4$ is hydrogen, lower alkyl, iodo, bromo, chloro, carboxy, esters, carbamoyl, lower-alkyl carbonyl, halocarbonyl or nitro; and $R^7$ is hydrogen or lower alkyl;

or a pharmaceutically acceptable ester, ether or salt thereof.

Another aspect of the invention relates to processes for making the compounds of Formula I and the pharmaceutically acceptable salts and esters thereof. For example, a compound of Formula I (where Z is oxygen) is made by reacting a compound of Formula II with a suitably substituted hydrazine. Or, a compound of Formula I (where Z is oxygen) is treated with a thiation reagent for ketones, e.g., Lawesson's Reagent, to give the corresponding compound of Formula I where Z is sulfur.

Another aspect of the invention relates to processes for making the compounds of Formula I (where $R^1$ is lower alkyl, aryl or heteroaralkyl) by reacting a compound of Formula I (where $R^1$ is hydrogen) with a suitably substituted alcohol.

In another aspect, this invention provides compositions useful in the treatment of inflammatory, asthmatic, allograft rejection, graft-vs-host or autoimmune conditions or diseases, or pain in mammals through its use as an anti-inflammatory, antasthmatic, immunosuppressive, anti-allograft rejection, anti-graft-vs-host rejection, autoimmune disease, or analgetic agent, wherein the composition comprises a therapeutically effective amount of a compound of Formula I as described above and a pharmaceutically acceptable excipient.

DETAILED DESCRIPTION

Definitions and General Parameters

The following definitions are set forth to illustrate and define the meaning and scope of the various terms used to describe the invention herein.

The term "alkyl" refers to a branched or straight chain monovalent hydrocarbon radical of one to twenty-four carbon atoms.

The term "lower alkyl" refers to a branched or straight chain saturated hydrocarbon radical of one to nine carbon atoms. This term is further exemplified by such radicals as methyl, ethyl, n-propyl, isopropyl, i-butyl, n-butyl, t-butyl, pentyl, n-hexyl, n-heptyl.

The term "lower alkoxy" refers to the group —O—R' where R' is lower alkyl.

The term "cycloalkyl" refers to a monovalent carbocyclic hudrocarbon radical of three to seven carbon atoms. The term is exemplified by such radicals as cyclopropyl, cyclopentyl, cyclohexyl and cycloheptyl.

The term "halo" refers to fluoro, bromo, chloro, iodo.

The term "carboxy" refers to the group —C(O)OH.

The term "alkoxycarbonyl" refers to the group —C(O)OR where R is alkyl.

The term "lower-alkyl carbonyl" refers to the group —C(O)—(lower-alkyl)

The term "halocarbonyl" refers to the group —C(O)X where X is halo.

The term "carbamoyl" refers to the group —C(O)NR'R" where R' and R" are independently hydrogen or lower alkyl.

The term "aryl" refers to a monovalent unsaturated aromatic carbocyclic radical having a single ring (e.g., phenyl) or two condensed rings (e.g., naphthyl), which can optionally be mono-, di-, tri-, tetra- or penta-substituted, independently, with hydroxy (phenol), lower alkyl (toluenyl or benzyl), lower alkoxy, chloro, fluoro, trifluoromethyl, carbamoyl, nitro and/or cyano.

The term "aralkyl" refers to the group aryl-(lower alkyl), wherein aryl and lower alkyl are as defined above. Typical aralkyl groups are, e.g. benzyl (i.e., phenytmethyl), 4-methoxybenzyl, 4-chlorobenzyl, 3,5-dichlorobenzyl, 2-naphthylmethyl and the like.

The term "heterocyclo" refers to saturated or unsaturated monovalent mono- or poly- carbocyclic radicals having at least one hetero atom (such as nitrogen, oxygen or sulfur) or a combination thereof, which can optionally be substituted, independently, with, e.g., hydroxy, amino, imino, lower alkyl, lower alkoxy, carboxy, carbamoyl, lower-alkyl carbonyl, halocarbonyl, aryl, aralkyl, halo, cyano, heteroaryl and/or heterocyclo. Further, the term also includes instances where a heteroatom of the radical has been oxidized, e.g., N-oxides, sulfoxides, sulfones, or oxo. For example, typical heterocyclo groups with one or more nitrogen or sulfur atoms are pyrrolinyl, pyrrolidinyl, dioxolanyl, imidazolinyl, imidazolidinyl, pyrazolinyl, pyrazolidinyl, pyranyl, piperidinyl, dioxoanyl, morpholinyl, 1,4-dithianyl, thiomorpholinyl, piperazinyl, 1,3,5-trithianyl, and the like.

The term "heterocyclo lower-alkyl" refers to the group heterocyclo-(lower alkyl), wherein heterocyclo and lower alkyl are as defined above. Typical heterocyclo lower-alkyl groups are, e.g. piperidinylmethyl, 2-norboranylmethyl, 2-(1,3-dioxolanyl)methyl, 3-(1-methylpyridonyl)methyl, 8-(6-fluorobenzo-1,3-dioxanyl)methyl and the like.

The term "heteroaryl" refers to aromatic monovalent mono- or poly- carbocyclic radicals having at least one hetero atom (such as nitrogen, oxygen or sulfur) or a combination thereof, which can optionally be substituted, independently, with, e.g., hydroxy, amino, imino, lower alkyl, lower alkoxy, carboxy, carbamoyl, lower-alkyl carbonyl, halocarbonyl, aryl, aralkyl, halo, cyano, heteroaryl, and/or heterocyclo. Further, the term also includes instances where an atom of the radical has been oxidized, e.g., N-oxides, sulfoxides, sulfones, or oxo. For example, typical heteroaryl moieties with one or more nitrogen or sulfur atoms are pyrroyl, pyridinyl, furyl, thienyl, [oxazoyl, thiazoyl, imidazoyl, pyrazoyl, isoxazolyl, isothiazoyl, 1,2,3-oxadiazoyl, 1,2,3-triazoyl, 1,3,4-thiadiazoyl, pyridazinyl, pyrimidinyl, pyrazinyl, 1,3,5-triazinyl, indoyl, benzo[b]furanyl, benzo[b]thiophenyl, benzimidazoyl, benzthiazoyl, purinyl, quinolinyl, isoquinolinyl, cinnolinyl, phthalazinyl, quinazolinyl, quinoxalinyl, 1,8-naphthyridinyl, pteridinyl and the like.

The term "heteroaralkyl" refers to the group heteroaryl-(lower alkyl), wherein heteroaryl and lower alkyl are as defined above. Typical heteroaralkyl groups are, e.g. 4-pyridylmethyl, 3-pyridylmethyl, 2-pyridylmethyl, 2-pyridylpropyl, 3-thienylmethyl, 2-thienylethyl, 2-imidazoyl, 3,5-dimethylisoxazolylmethyl, 3-pyridonylmethyl, 5-(4-methylthiazolyl)methyl, 3-furanylmethyl, 2-furanylmethyl, 5-(2-methyl-5-nitroimidazolyl)methyl, 4-[2-(4-chlorophenyl)thiazolyl]methyl, 4-(2-methylthiazolyl)methyl, 4-(5-phenyl-1,2,4-oxadiazolyl)methyl, 4-[2-(4-methoxybenzyl)thiazolyl]methyl, 3-(1,2,4-oxadiazolyl)methyl, 3-[5-(3,5-dimethyl-isoazoyl-4-yl)-1,2,4-oxadiazolyl]methyl and the like.

The term "N-oxide" refers to nitrogen heterocycles where a nitrogen atom in the ring has been oxidized, e.g., 4-pyridyl-N-oxide, 3-pyridyl-N-oxide, or 2-pyridyl-N-oxide.

The term "esterification reagent" refers to a reagent (e.g., diazomethane, methanol, methyl iodide, ethyl iodide or ethanol) that when contacted with a carboxy group results in the formation of the corresponding alkoxycarbonyl group.

The term "alkylating agent" refers to a halo-substituted alkyl, aryl, aralkyl, heterocyclo, heterocyclo lower-alkyl, heteroaryl, or heteroaralkyl compound (e.g., iodoethane, 2-iodopropane, iodobutane, iodopentane, 4-picolyl chloride, 3-picolyl chloride or benzyl bromide) that, when in the presence of a base, can join the alkyl, aryl, aralkyl, heterocyclo, heterocyclo lower-alkyl, heteroaryl, or heteroaralkyl moiety to a nitrogen atom.

The term "compound", as used in the detailed description in reference to the compound of Formula I, is intended to refer to the pharmaceutically acceptable salts, esters and ethers of the compound, unless expressly stated otherwise, such as "the compound of Formula I as a free base".

The term "pharmaceutically acceptable salt" refers to any salt derived from an inorganic or organic acid or base. The term "pharmaceutically acceptable anion" refers to the anion of such acid addition salts. The term "pharmaceutically acceptable cation" refers to the cation of such base addition salts. The salt, anion and/or the cation are chosen not to be biologically or otherwise undesirable.

The anions are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, hexanoic acid, heptanoic acid, cyclopentanepropionic acid, glycolic acid, lactic acid, pyruvic acid, oxalic acid, malic acid, malonic acid, succinic acid, maleic acid, fumaric acid, tartaric acid, citric acid, benzoic acid, o-(4-hydroxybenzoyl)- benzoic acid, benzenesulfonic acid, p-chlorobenzene- sulfonic acid, 2-naphthalenesulfonic acid, cinnamic acid, mandelic acid, methanesulfonic acid, ethanesulfonic acid, 1,2-ethane disulfonic acid, 2-hydroxyethanesulfonic acid, salicylic acid, p-toluensulfonic acid and the like.

The cations are derived from bases, such as alkaline earth hydroxides, including calcium hydroxide, potassium hydroxide, potassium carbonate, sodium hydroxide, sodium hydride, lithium hydroxide and the like, preferably sodium hydroxide.

The term "pharmaceutically acceptable esters" and "pharmaceutically acceptable ethers" refer to those compounds of Formula I where an oxygen or a nitrogen has been modified, e.g., acylated by the addition of the group —C(=O)—W, wherein W is an alkyl group containing 1 to 20 carbon atoms including adamantyl, aryl, aralkyl, amino, alkylamino, dialkylamino, an alkoxy group containing 1 to 20 carbon atoms, —CH$_2$—O—CH$_3$, or —CH$_2$—NH$_2$. This invention contemplates those compounds of Formula I which are esters as described herein and at the same time are the pharmaceutically acceptable acid addition salts thereof. The terms "inert organic solvent" or "inert solvent" refer to a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, pyridine and the like]. Unless specified to the contrary, the solvents used in the reactions of the present invention are inert organic solvents.

As used herein, the term "autoimmune disease" refers to disorders wherein the immune system of a mammal mounts a humoral or cellular immune response to the mammal's own tissue or to antigenic agents that are not intrinsically harmful to the mammal, thereby producing tissue injury in such a mammal. Examples of such disorders include, but are not limited to, systemic lupus erythematosus, rheumatoid arthritis and type I diabetes.

As used herein, the term "allograft rejection" refers to the humoral or cellular immune response mounted by the immune system of a mammal after it has received a histoincompatible tissue graft from another mammal of the same species, thereby producing tissue injury in such a mammal.

As used herein, the term "graft-vs-host disease" refers to the immune response that originates from transplanted graft tissue, in particular, transplanted bone-marrow tissue, and that is directed towards the host tissue, thereby producing tissue injury in the host.

As used herein, the term "treatment" or "treating" means any treatment of a disease in a mammal, including:

(i) preventing the condition or disease, that is, avoiding any clinical symptoms of the disease;

(ii) inhibiting the condition or disease, that is, arresting the development or progression of clinical symptoms; and/or (iii) relieving the condition or disease, that is, causing the regression of clinical symptoms.

As used herein, the term "therapeutically effective amount" refers to that amount of a compound of Formula I which, when administered to a mammal in need thereof, is sufficient to effect treatment (as defined above) as an anti-inflammatory, antasthmatic, immunosuppressive, anti-allograft rejection, anti-graft-vs-host disease, autoimmune disease or analgetic agent(s). What amount constitutes a "therapeutically effective amount" will vary depending on the compound, the condition and its severity, and the mammal to be treated, but may be determined routinely by one of ordinary skill in the art having regard to his own knowledge and to this disclosure.

As used herein, the term "q.s." means adding a quantity sufficient to achieve a stated function, e.g., to bring a solution to a desired volume (e.g., 100 mL).

Unless specified to the contrary, the reactions described herein take place at atmospheric pressure over a temperature range from about −100° C. to about 200° C., more preferably from about 10° C. to about 50° C., and most preferably at about room (or "ambient") temperature, e.g., about 20° C.

Isolation and purification of the compounds and intermediates described herein can be effected, if desired, by any suitable separation or purification procedure such as, for example, filtration, extraction, crystallization, column chromatography, preparative high pressure liquid chromatography (preparative HPLC), thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

For the compounds of the instant invention containing a pyridopyridazinone ring moiety, where X is nitrogen, Y is carbon, and Z is oxygen (i.e., pyrido[2,3-d]pyridazin-5-one compounds), the following numbering system will be used for naming said compounds.

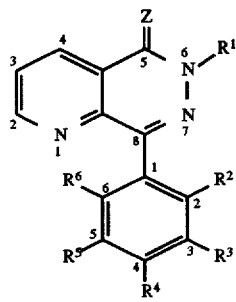

Formula I

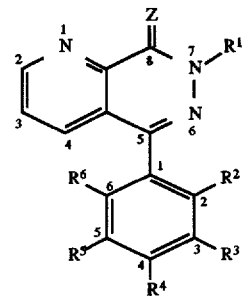

Formula I

Some representative compounds are named in the following examples.

The compound of Formula I where X is nitrogen, Y is carbon, Z is oxygen, $R^1$ is pyridylmethyl, $R^2$, $R^3$, $R^4$, $R^5$ and $R^6$ are hydrogen, can be named 6-(4-pyridylmethyl)-8-phenyl-pyrido[2,3-d]pyridazin-5-one.

The compound of Formula I where X is nitrogen, Y is carbon, Z is oxygen, $R^1$ is benzyl, $R^2$, $R^3$, $R^4$, $R^5$ and $R^6$ are hydrogen, can be named 6-benzyl-8-phenyl-pyrido-[2,3-d]pyridazin-5-one.

The compound of Formula I where X is nitrogen, Y is carbon, Z is oxygen, $R^1$ is benzyl, $R^3$ is nitro, $R^2$, $R^4$, $R^5$ and $R^6$ are hydrogen, can be named 6-benzyl-8-(3-nitrophenyl)-pyrido[2,3-d]pyridazin-5-one.

The compound of Formula I where X is nitrogen, Y is carbon, Z is oxygen, $R^1$ is benzyl, $R^3$ is chloro, $R^2$, $R^4$, $R^5$ and $R^6$ are hydrogen, can be named 6-benzyl-8-(3-chlorophenyl)-pyrido[2,3-d]pyridazin-5-one.

The compound of Formula I where X is nitrogen, Y is carbon, Z is oxygen, $R^1$ is benzyl, $R^3$ is chloro, $R^5$ is bromo, $R^2$, $R^4$ and $R^6$ are hydrogen, can be named 6-benzyl-8-(3-chloro-5-bromophenyl)-pyrido[2,3-d]pyridazin-5-one.

The compound of Formula I where X is nitrogen, Y is carbon, Z is oxygen, $R^1$ is ethyl, $R^3$ is chloro, $R^2$, $R^4$, $R^5$ and $R^6$ are hydrogen, can be named 6-ethyl-8-(3-chlorophenyl)-pyrido[2,3-d]pyridazin-5-one.

The compound of Formula I where X is nitrogen, Y is carbon, Z is oxygen, $R^1$ is 4-pyridyl-N-oxide-methyl, $R^3$ is nitro, $R^2$, $R^4$, $R^5$ and $R^6$ are hydrogen, can be named 6-(4-pyridyl-N-oxide-methyl)-8-(3-nitrophenyl)-pyrido-[2,3-d]pyridazin-5-one.

The compound of Formula I where X is nitrogen, Y is carbon, Z is oxygen, $R^1$ is 4-pyridyl-N-oxide-methyl, $R^3$ is chloro, $R^2$, $R^4$, $R^5$ and $R^6$ are hydrogen, can be named 6-(4-pyridyl-N-oxide-methyl)-8-(3-chlorophenyl)-pyrido-[2,3-d]pyridazin-5-one.

The compound of Formula I where X is nitrogen, Y is carbon, Z is sulfur, $R^1$ is benzyl, $R^3$ is chloro, $R^2$, $R^4$, $R^5$ and $R^6$ are hydrogen, can be named 6-benzyl-8-(3-chlorophenyl)-pyrido[2,3-d]pyridazin-5-thione.

For the compounds of the instant invention containing a pyridopyridazinone ring moiety, where X is carbon, Y is nitrogen, and Z is oxygen (i.e., pyrido[2,3-d]pyridazin-8-one compounds), the following numbering system will be used for naming said compounds.

Some representative compounds are named in the following examples.

The compound of Formula I where X is carbon, Y is nitrogen, Z is oxygen, $R^1$ is 4-pyridylmethyl, $R^2$, $R^3$, $R^4$, $R^5$ and $R^6$ are hydrogen, can be named 7-(4-pyridylmethyl)-5-phenyl-pyrido[2,3-d]pyridazin-8-one.

The compound of Formula I where X is carbon, Y is nitrogen, Z is oxygen, $R^1$ is benzyl, $R^2$, $R^3$, $R^4$, $R^5$ and $R^6$ are hydrogen, can be named 7-benzyl-5-phenyl-pyrido-[2,3-d]pyridazin-8-one.

The compound of Formula I where X is carbon, Y is nitrogen, Z is oxygen, $R^1$ is benzyl, $R^3$ is nitro, $R^2$, $R^4$, $R^5$ and $R^6$ are hydrogen, can be named 7-benzyl-5-(3-nitrophenyl)-pyrido[2,3-d]pyridazin-8-one.

The compound of Formula I where X is carbon, Y is nitrogen, Z is oxygen, $R^1$ is benzyl, $R^3$ is chloro, $R^2$, $R^4$, $R^5$ and $R^6$ are hydrogen, can be named 7-benzyl-5-(3-chlorophenyl)-pyrido[2,3-d]-pyridazin-8-one.

The compound of Formula I where X is carbon, Y is nitrogen, Z is oxygen, $R^1$ is benzyl, $R^3$ is chloro, $R^5$ is bromo, $R^2$, $R^4$ and $R^6$ are hydrogen, can be named 7-benzyl-5-(3-chloro-5-bromophenyl)-pyrido[2,3-d]pyridazin-8-one.

The compound of Formula I where X is carbon, Y is nitrogen, Z is oxygen, $R^1$ is ethyl, $R^3$ is chloro, $R^2$, $R^4$, $R^5$ and $R^6$ are hydrogen, can be named 7-ethyl-5-(3-chlorophenyl)-pyrido[2,3-d]pyridazin-8-one.

The compound of Formula I where X is carbon, Y is nitrogen, Z is oxygen, $R^1$ is 4-pyridyl-N-oxide-methyl, $R^3$ is nitro, $R^2$, $R^4$, $R^5$ and $R^6$ are hydrogen, can be named 7-(4-pyridyl-N-oxide-methyl)-5-(3-nitrophenyl)-pyrido-[2,3-d]pyridazin-8-one.

The compound of Formula I where X is carbon, Y is nitrogen, Z is oxygen, $R^1$ is 4-pyridyl-N-oxide-methyl, $R^3$ is chloro, $R^2$, $R^4$, $R^5$ and $R^6$ are hydrogen, can be named 7-(4-pyridyl-N-oxide-methyl)-5-(3-chlorophenyl)-pyrido-[2,3-d]pyridazin-8-one.

For the compounds of the instant invention containing a benzopyridazinone ring moiety (e.g., the compounds of Formula I where X and Y are carbon atoms, and Z is oxygen) the following numbering system will be used for naming said compounds.

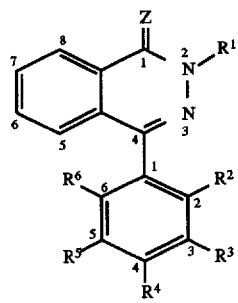

Formula I

Some representative compounds are named in the following examples.

The compound of Formula I where X and Y are carbon, Z is oxygen, $R^1$ is 4-pyridylmethyl, $R^2$, $R^3$, $R^4$, $R^5$ and $R^6$ are hydrogen, can be named 4-phenyl-2-(4-pyridylmethyl)-1-(2H) phthalazinone.

The compound of Formula I where X and Y are carbon, $R^1$ is benzyl, $R^2$, $R^3$, $R^4$, $R^5$ and $R^6$ are hydrogen, can be n is oxygen, amed 4-phenyl-2-benzyl-1-(2H) phthalazinone.

The compound of Formula I where X and Y are carbon, Z is oxygen, $R^1$ is benzyl, $R^3$ is nitro, $R^2$, $R^4$, $R^5$ and $R^6$ are hydrogen, can be named 4-(3-nitrophenyl)-2-benzyl-1-(2H) phthalazinone.

The compound of Formula I where X and Y are carbon, Z is oxygen, $R^1$ is benzyl, $R^3$ is chloro, $R^2$, $R^4$, $R^5$ and $R^6$ are hydrogen, can be named 4-(3-chlorophenyl)-2-benzyl-1-(2H)phthalazinone.

The compound of Formula I where X and Y are carbon, Z is oxygen, $R^1$ is benzyl, $R^3$ is chloro, $R^5$ is bromo, $R^2$, $R^4$ and $R^6$ are hydrogen, can be named 4-(3-chloro-5-bromophenyl)-2-benzyl-1-(2H) phthalazinone.

The compound of Formula I where X and Y are carbon, Z is oxygen, $R^1$ is ethyl, $R^3$ is chloro, $R^2$, $R^4$, $R^5$ and $R^6$ are hydrogen, can be named 4-(3-chlorophenyl)-2-ethyl-1-(2H) phthalazinone.

The compound of Formula I where X and Y are carbon, Z is oxygen, $R^1$ is 4-pyridyl-N-oxide-methyl, $R^3$ is nitro, $R^2$, $R^4$, $R^5$ and $R^6$ are hydrogen, can be named 4-(3-nitrophenyl)-2-(4-pyridyl-N-oxide-methyl)-1-(2 H )phthalazinone.

The compound of Formula I where X and Y are carbon, Z is oxygen, $R^1$ is 4-pyridyl-N-oxide-methyl, $R^3$ is chloro, $R^2$, $R^4$, $R^5$ and $R^6$ are hydrogen, can be named 4-(3-chlorophenyl)-2-(4-pyridyl-N-oxide-methyl)-1-(2H) phthalazinone.

SYNTHESIS OF THE COMPOUNDS OF FORMULAE I AND II

The compounds of Formulae I and II are synthesized as described with reference to Reaction Scheme A. As used in Reaction Scheme A, X and Y are nitrogen or carbon atoms, provided at least one is a carbon atom, and Z is oxygen. $R^1$ is hydrogen, lower alkyl, cycloalkyl, cycloalkyl lower alkyl, aryl, aralkyl, heterocyclo, heterocyclo lower-alkyl, heteroaryl, or heteroaralkyl; and $R^2$, $R^3$, $R^4$, $R^5$ and $R^6$ are independently selected from hydrogen, lower alkyl, halo, carboxy, alkoxycarbonyl, carbamoyl, lower-alkyl carbonyl, halocarbonyl, thiomethyl, trifluoromethyl, cyano or nitro.

Reaction Scheme A illustrates the preparation of novel benzo or pyridopyridazinones (Formula I where X is nitrogen, Y is carbon, and Z is oxygen) and the corresponding intermediate benzo or pyridoarylketoesters (Formula II).

Reaction Scheme B illustrates a preparation for the intermediate benzo or pyridoarylketoesters (Formula II where X and Y are carbon or nitrogen, provided at least one is carbon) using an organolithium, organocadmium or Grignard reagent.

Reaction Scheme C illustrates an alternative preparation of novel benzo or pyridopyridazinones (Formula I where Z is oxygen) from benzo or pyridopyridazinones, where $R^1$ is hydrogen.

Reaction Scheme D illustrates a preparation for the intermediate benzo or pyridoarylketoesters (Formula II where X and Y are carbon or nitrogen, provided at least one is carbon, and $R^3$ is nitro).

Reaction Scheme E illustrates a preparation of novel pyridyl-N-oxide-methyl substituted pyridopyridazinones (Formula I) from pyridopyridazinones (Formula I), where $R^1$ is hydrogen.

Reaction Schemes F and G illustrate an alternative preparation of novel optionally substituted compounds of Formula I, where X is nitrogen, Y is carbon, Z is oxygen, and $R^1$ is hydrogen.

REACTION SCHEME A

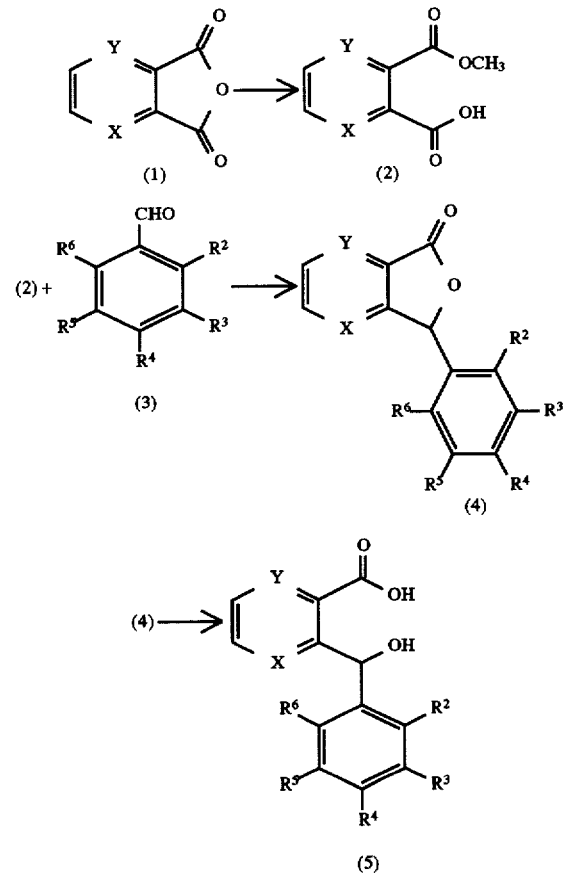

-continued
REACTION SCHEME A

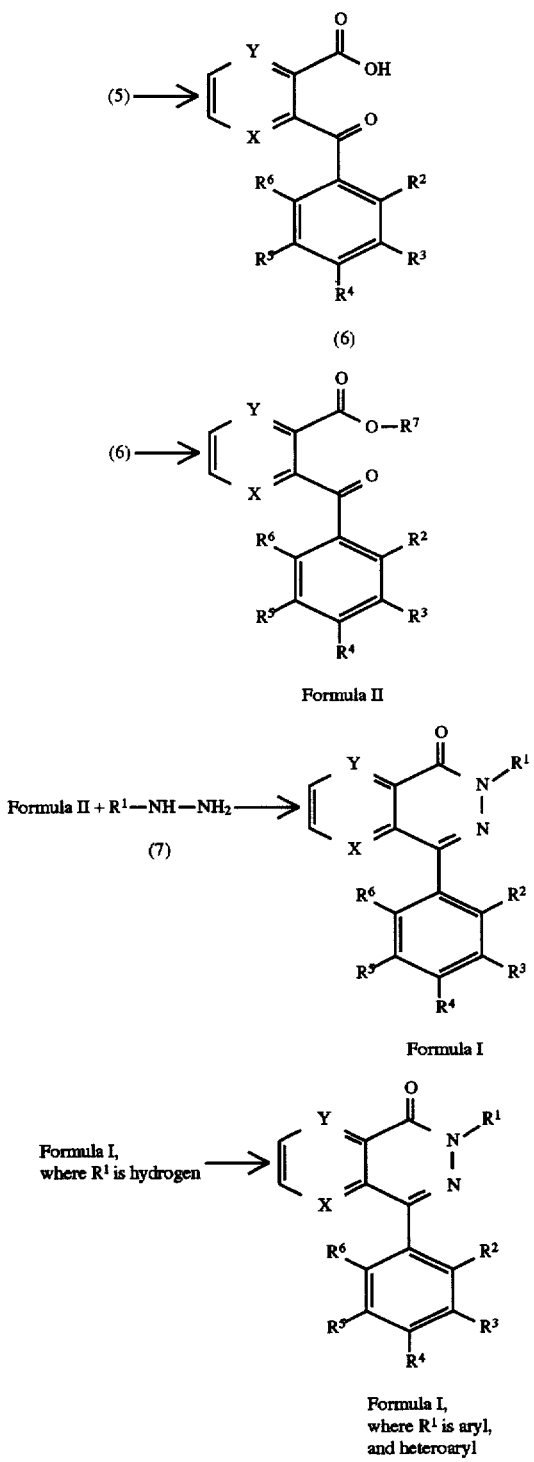

Starting Materials

Referring to Reaction Scheme A, most of the compounds of Formula 1 are commercially available from Aldrich Chemicals and ICN Chemicals. Similarly, many of the substituted hydrazines (Formula 7) are commercially available from Aldrich Chemicals, those that are not can be prepared by following the disclosures of S. R. Sandler and W. Karo, "Organic Functional Group Preparations" 2nd Ed. 1983, Vol 12-I, Academic Press, New York.

Preparation of Formula 2

A benzo or pyridodicarboxylic anhydride (Formula 1) is dissolved in a solvent [e.g., an alcohol (methanol or ethanol), preferably methanol] and heated for a period of about 2 to 20 minutes, preferably about 10 minutes at a temperature of about 60° to 120° C., preferably about 100° C. The desired product is taken directly to the next step without purification.

Preparation of Formula 4

An optionally substituted benzo or pyridoacidester (Formula 2) is added to about 5.0 molar equivalents of an optionally substituted benzaldehyde (Formula 3) and about 5.0 molar equivalents of a solvent, such as p-cymene, dibromobenzene, nitrotoluene, bromoanisole or xylene, preferably p-cymene. The mixture is heated to a temperature of about 150° C. to 210° C., preferably about 180° C. for a period of about 2 to 6 hours, preferably about 4 hours. The solution is cooled and the excess benzaldehyde and solvent are removed yielding the desired optionally substituted benzo or pyridolactone (the compound of Formula 4). The desired compound can be purified by silica gel chromatography or the like, however, preferably the desired compound is taken without purification directly to the next step.

Preparation of Formula 5

An optionally substituted benzo or pyridolactone (Formula 4) is suspended in a basic solution (e.g., potassium hydroxide, sodium hydroxide or ammonium hydroxide in a solvent such as, methanol or ethanol, preferably potassium hydroxide in methanol at a ratio of about 4.5 grams/100 ml) and refluxed for a period of about 3 to 9 hours, preferably about 6 hours. The mixture is cooled and the solvent removed yielding a benzo or pyridobenzylhydroxy acid (Formula 5).

Preparation of Formula 6

A benzo or pyridobenzylhydroxy acid (Formula 5) is suspended in a solvent that is inert to oxidation agents (e.g., methylene chloride, chloroform or carbon tetrachloride, preferably methylene chloride). To this solution is added about 1.0 molar equivalent of an oxidation agent, such as pyridinium dichromate, pyridinium chlorochromate or manganese dioxide, preferably pyridinium dichromate. The solution is stirred at a temperature in the range of about 0° C. to 50° C., preferably about 21° C. (room temperature) for a period of about 9 to 27 hours, preferably about 18 hours, yielding the desired optionally substituted benzo or pyridobenzoylacid (Formula 6). The desired product can be isolated and purified, however, the product is preferably taken directly to the next step without purification.

Preparation of Formula II

A benzo or pyridobenzoylacid (Formula 6) is dissolved in a solvent (e.g., methylene chloride, chloroform or carbon tetrachloride, preferably methylene chloride) and cooled to a temperature in the range of about −20° C. to 20° C., preferably about 0° C. About 1.2 molar equivalent of an esterification reagent such as, diazomethane, is added to the solution and stirred for a period of about 1 to 5 hours, preferably the reaction is monitored by TLC to completion (about 2 hours). The desired optionally substituted benzo or pyridobenzoylester (Formula II) is isolated and purified by the removal of the solvent followed by chromatography.

Alternatively, an optionally substituted benzo or pyridobenzoylester (Formula II) is prepared by dissolving a suitably substituted benzo or pyridobenzoylacid (Formula 6) in a solvent (e.g., methanol, ethanol or the like, preferably methanol) to which is added about 1 molar equivalent of a strong acid (e.g., concentrated $H_2SO_4$, HCl (gas), $BF_3 \cdot Et_2O$, preferably concentrated $H_2SO_4$). The solution is stirred for a period of about 6 to 30 hrs, preferably about 18 hrs at the reflux temperature of the solvent used. The solution is cooled and made basic. The desired optionally substituted benzo or pyridobenzoylester (Formula II) is isolated and purified by chromatography.

As indicated the desired compound may be purified by silica gel chromatography or the like, however, preferably the desired compound is taken without further purification to the next step.

Preparation of Formula I

An optionally substituted benzo or pyridobenzoylester (Formula II) is suspended in a solvent (about 15 ml/mmole) (e.g., ethanol, methanol or the like, preferably ethanol). To this suspension is added about 2 molar equivalents of an unsubstituted or substituted hydrazine (Formula 7, where $R^1$ is hydrogen, lower alkyl, cycloalkyl, cycloalkyl lower alkyl, aryl, aralkyl, heterocyclo, heterocyclo lower-alkyl, heteroaryl, or heteroaralkyl). The mixture is refluxed for a period of about 4 hours to 240 hours. The specific time is dependent on the substituent (i.e., $R^1$) of the hydrazine. Preferably, the reaction mixture is monitored by TLC for completion. The mixture is allowed to cool and filtered to give a crude product. The desired benzo or pyridobenzoylpyridazinones (Formula I) are purified and isolated following extraction and chromatography.

Other optionally substituted compounds of Formula I are prepared by suspending a suitably substituted compound of Formula I, where $R^1$ is hydrogen, in a solvent (about 10 to 100 ml/mmole). To this suspension is added about 1 to 20 molar equivalents of a suitable base (e.g. sodium hydride, potassium carbonate, potassium iodide) and about 1 to 20 molar equivalents of a suitable alkylating agent (e.g., iodoethane, 4-picolyl chloride, 2-iodopropane). The mixture is refluxed under an inert atmosphere for about 6 to 48 hours, preferably about 18 hours, most preferably the reaction is monitored by TLC for completion. The mixture is allowed to cool and purified following standard chromatographic techniques yielding the desired benzo and pyridobenzoylpyridazi- nones (Formula I).

REACTION SCHEME B

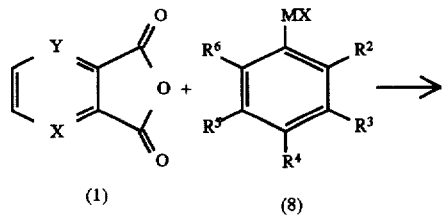

(1)   (8)

-continued
REACTION SCHEME B

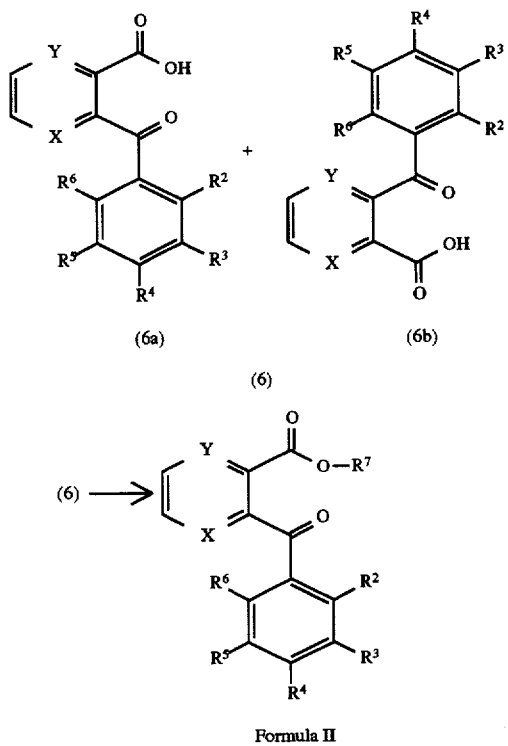

Formula II

Alternate Preparation of Formula II

Alternatively, the compounds of Formula II can be prepared using an organolithium or organocadmium reagent as illustrated in "Preparation of Aroylbenzoic Acid. Reaction of Aryllithium Reagents with Phthalic Anhydride", J. Organic Chem., 41(7), 1268 (1976), or by Grignard reagent.

The Grignard preparation is illustrated in Reaction Scheme B (where M is Mg). A Grignard reagent is prepared by adding to a solution of an optionally substituted halogenated aryl compound (Formula 8) in a solvent (e.g., tetrahydrofuran or ethyl ether, preferably tetrahydrofuran) about 1 molar equivalent of magnesium followed by stirring for a period of 12 to 24 hours, preferably 18 hours, at a temperature in the range of about 0° C. to 50° C., preferably room temperature under an inert atmosphere. The Grignard reagent (Formula 8) is added to a benzo or pyridodicarboxylic anhydride (Formula 1) in a solvent (e.g., tetrahydrofuran, methylene chloride, chloroform or ethyl ether, preferably tetrahydrofuran) at a temperature in the range of about 0° C. to -150° C., preferably about -78° C. in a gradual manner over a period of about 2 hours.

After the addition, the solution is stirred for a period of about 15 minutes to 75 minutes, preferably about 45 minutes. An acid (e.g., 1N HCl) is added to the solution at a slight molar excess and stirred for a period of about 1 hour. In the case where Formula 1 is pyridodi- carboxylic anhydride (i.e., where either X or Y are nitrogen), the preparation results in two positional isomers of the Formula 6, i.e. Formulae 6a and 6b. Depending on the desired product, i.e., Formula I where X is nitrogen and Y is carbon, or Formula I where X is carbon and Y is nitrogen, the suitable isomer of Formula 6 (Formulae 6a or 6b) is isolated and purified and used in the following preparations as the compound of Formula 6.

Preparation of Formula II

An optionally substituted benzo or pyridobenzoylester (Formula II) can be prepared from a benzo or pyridobenzoylacid (Formula 6) by following the procedures set forth in Reaction Scheme A.

REACTION SCHEME C

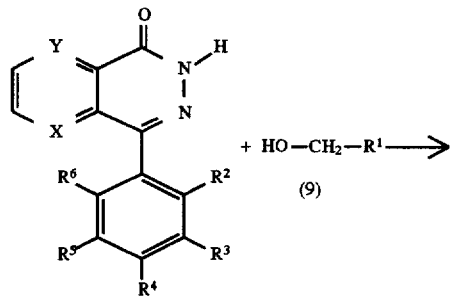

+ HO—CH$_2$—R$^1$ →

(9)

Formula I, where
R$^1$ is hydrogen

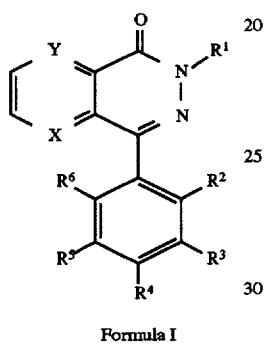

Formula I

Preparation of Formula I Where R$^1$ is Lower Alkyl, Cycloalkyl, Cycloalkyl Lower Alkyl, Aryl, Aralkyl, Heterocyclo, Heterocyclo Lower-Alkyl, Heteroaryl, or Heteroaralkyl Alternatively, optionally substituted benzo or pyridopyridazinone compounds (Formula I, where R$^1$ is lower alkyl, cycloalkyl, cycloalkyl lower alkyl, aryl, aralkyl, heterocyclo, heterocyclo lower-alkyl, heteroaryl, or heteroaralkyl) can be prepared from a benzo or pyridopyridazinone compound (Formula I) where R$^1$ is hydrogen by following Mitsunobu reaction conditions, as illustrated in O. Mitsunobu, *Synthesis*, 1, 1981, and incorporated herein by reference.

To a suspension of a benzo or pyridopyridazinone (Formula I) where R$^1$ is hydrogen in a solvent (e.g., tetrahydrofuran, diethyl ether, dioxane, preferably tetrahydrofuran) is added about 1 molar equivalent of an optionally substituted alcohol (Formula 9, where R$^1$ is lower alkyl, cycloalkyl, cycloalkyl lower alkyl, aryl, aralkyl, heterocyclo, heterocyclo lower-alkyl, heteroaryl, or heteroaralkyl) and about 1.5 molar equivalent of a trisubstituted phosphine, preferably triphenylphosphine. To the solution is added about 1.5 molar equivalent of a disubstituted azodicarboxylate, such as diethyl azodicarboxylate (DEAD) or diisopropyl azodicarboxylate (DIAD), preferably diisopropyl azodicarboxylate in a gradual manner. The solution is stirred for a period of about 12 to 24 hours, preferably about 18 hours at a temperature in the range of about 0° C. to 50° C., preferably about 21° C. (room temperature). The solvent is removed and the desired optionally substituted benzo or pyridopyridazinone (Formula I, where R$^1$ is lower alkyl, cycloalkyl, cycloalkyl lower alkyl, aryl, aralkyl, heterocyclo, heterocyclo lower-alkyl, heteroaryl, or heteroaralkyl) is isolated and purified by chromatography.

REACTION SCHEME D

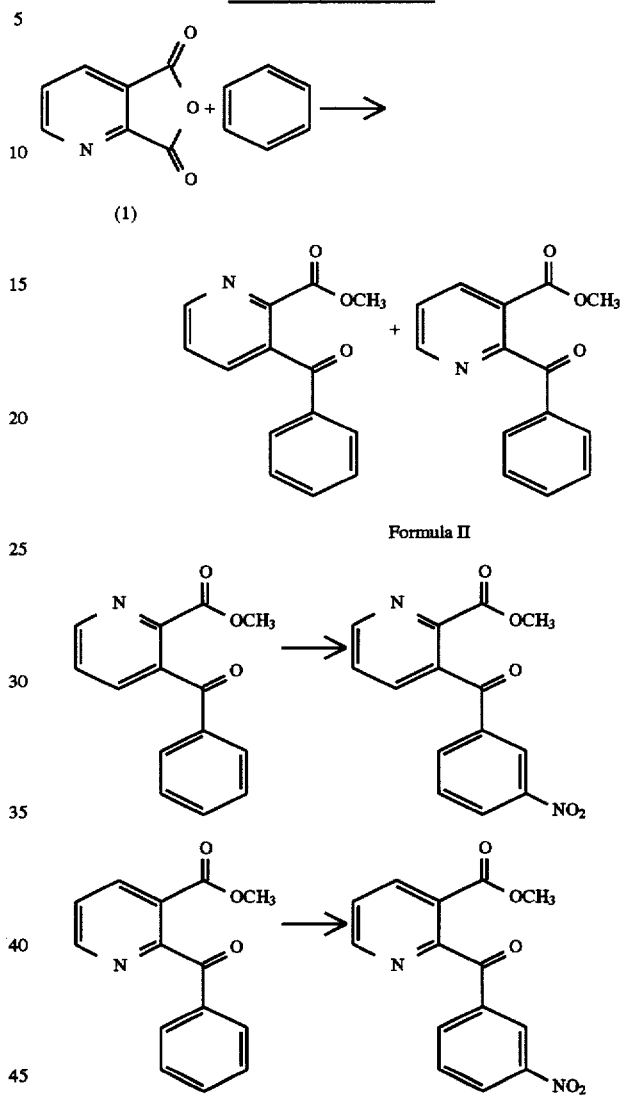

Preparation of Formula II Where X is Carbon and Y is Nitrogen

A pyridophenylketoester (i.e., Formula II where X and Y are carbon or nitrogen, provided at least one is carbon, and R$^2$, R$^3$, R$^4$, R$^5$ and R$^6$ are hydrogen) can be prepared following the procedures in U.S. Pat. No. 4,806,535.

Preparation of Formula II Where X is Carbon, Y is Nitrogen and R$^3$ is Nitro A pyrido(3-nitrobenzoyl)ketoester (Formula II where X is carbon, Y is nitrogen and W is nitro) is prepared by dissolving a pyridophenylketoester in an acid (such as hydrochloric acid, nitric acid, sulfuric acid, preferably, sulfuric acid) and adding in a dropwise manner a solution of nitric acid and sulfuric acid (about 1 to 3 molar equivalent of nitric acid with about 2 ml of sulfuric acid per molar equivalent of nitric acid). The solution is stirred for about 10 to 60 minutes, preferably about 30 minutes, cooled and adjusted to a pH of about 7 to 8. The solvent is removed and the desired optionally substituted pyrido-pyridazinone (Formula I, where X is carbon, Y is nitrogen, Z is oxygen, and R³ is nitro) is isolated and purified by chromatogryaphy.

Preparation of the Salt of Formula I

The pharmaceutically acceptable salts of Formula I are prepared by dissolving a compound of Formula I in a suitable solvent (such as methanol) adding 1 to 3 molar equivalents (preferably about two molar equivalent) of an appropriate acid (such as hydrochloric acid) or base (such as an alkaline earth hydroxide, e.g., lithium hydroxide, calcium hydroxide, potassium hydroxide, sodium hydroxide or the like, preferably sodium hydroxide) with stirring. The salt is isolated by lyophilization or by precipitation, using techniques that will be apparent to those skilled in the art.

REACTION SCHEME E

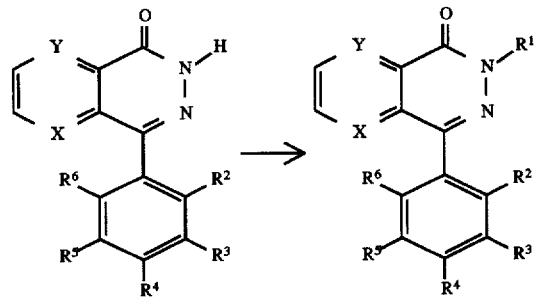

Preparation of Formula I Where R¹ is Pyridyl-N-Oxide-Alkyl

Optionally substituted pyridyl-N-oxide-alkyl pyridopyridazinones are prepared by following Mitsunobu reaction conditions, as illustrated in O. Mitsunobu, *Synthesis*, 1, 1981, and incorporated herein by reference. An optionally substituted pyridopyridazinone (Formula I) where R¹ is hydrogen is combined into a suspension with about 1.1 molar equivalents of an optionally substituted pyridyl-carbinol N-oxide, about 1.5 molar equivalents of triphenylphosphine in a solvent (e.g., tetrahydrofuran, diethyl ether, dioxane, preferably tetrahydrofuran). The suspension is stirred for a period of about 12 to 24 hours, preferably about 18 hours, at a temperature in the range of 12° to 36° C., preferable about 24° C. The solvent is removed and the desired optionally substituted pyridyl-N-oxide-alkyl pyridopyridazinone is isolated by chromatography, e.g., elution by 100% ethylacetate, followed by 10% methanol/ethylacetate or like solvent systems.

REACTION SCHEME F

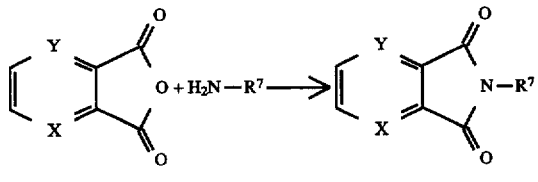

-continued
REACTION SCHEME F

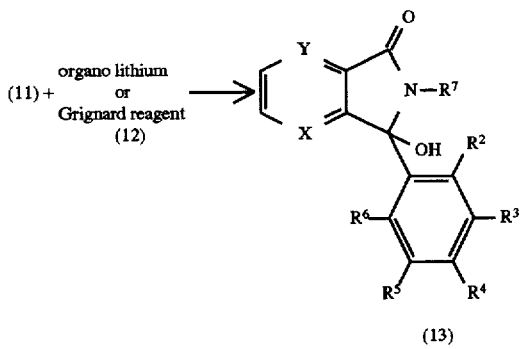

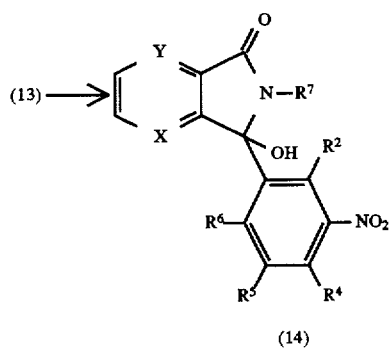

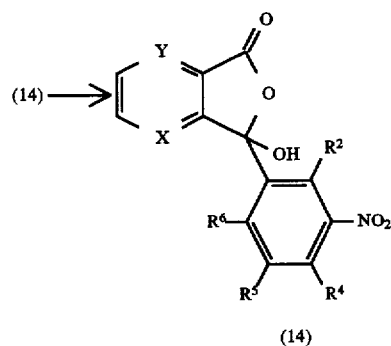

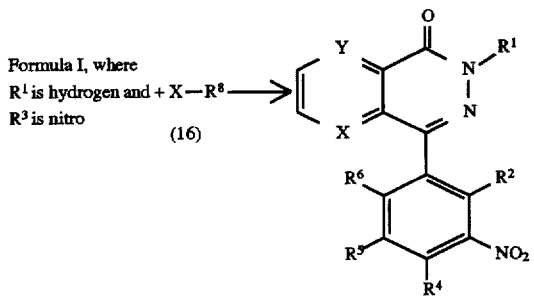

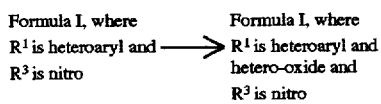

Preparation of a Compound of Formula 11

A pyridodicarboxylic anhydride (Formula 1, where X is nitrogen and Y is carbon) is suspended in a solvent (such as toluene, ethyl acetate, tetrahydrofuran, preferably ethyl acetate) and a primary amine (Formula 10, where $R^7$ is lower alkyl, such as, ethyl, propyl, butyl, hexyl, or n-butyl, preferably n-butyl) is added. The temperature is kept in a range of about −10° C. to about 80° C., preferably room temperature. After a period of about 10 minutes to about 24 hours, preferably about 1 hour, a dehydrating reagent (such as, acetic anhydride, trifluoroacetic anhydride, phosphorous pentoxide, or thionyl chloride, preferably thionyl chloride) is added. The temperature of the mixture is kept in a range of about 0° C. to about 80° C. (depending on the dehydrating reagent) for a period of about 30 minutes to about 4 hours, preferably about 1 hour. The resulting pyridoimide (Formula 11, where X is nitrogen, Y is carbon and $R^7$ is lower alkyl) is isolated by chromatography or crystallization, preferably crystallization.

Preparation of a Compound of Formula 13

The pyridoimide (Formula 11) is dissolved in a solvent that is inert to Grignard reagents and organolithium reagents (e.g., tetrahydrofuran, diethyl ether, toluene, preferably toluene) and cooled to a temperature in the range of about −100° C. to room temperature, preferably about −65° C. About 0.5 to 3.0 molar equivalent, preferably about 1.0 molar equivalent of an optionally substituted phenyl Grignard reagent or optionally substituted phenyl organolithium reagent, preferably an optionally substituted phenyl Grignard reagent (Formula 8) in either tetrahydrofuran or diethyl ether, preferably tetrahydrofuran is added at such a rate that the internal temperature of the solution is maintained in a range of about −78° C. to about room temperature, preferably about −45° C. After a period of about 10 minutes to about 5 hours, preferably about 30 minutes, the reaction is quenched with dilute hydrochloric acid, dilute acetic acid, aqueous ammonium chloride solution, dilute sulfuric acid, or the like, preferably aqueous ammonium chloride solution. The resulting phenyl pyridolactam compound (Formula 13 where X is nitrogen, Y is carbon, $R^7$ is lower alkyl, and $R^3$ is hydrogen) can be isolated by chromatography, crystallization or used as a crude mixture in the next reaction, preferably the product is isolated by crystallization.

Preparation of a Compound of Formula 14 Where $R^3$ is Nitro

The phenyl pyridolactam compound (Formula 13) is suspended in sulfuric acid and cooled to a temperature in the range of about −10° C. to about 40° C., preferably room temperature. Nitric acid is added at such a rate that the temperature is maintained below about 60° C., preferably below about 45° C. Following the addition of the nitric acid the mixture is stirred for a period of about 10 minutes to about 6 hours, preferably about 30 minutes. The mixture is then added to water and extracted with a water immiscible solvent (e.g., diethyl ether, ethyl acetate, toluene, methylene chloride, preferably ethyl acetate). The resulting optionally substituted nitrophenyl pyridolactam compound (Formula 14 where X is nitrogen, Y is carbon, and $R^3$ is nitro) can be isolated by chromatography, crystallization or preferably used directly in the next step.

Preparation of a Compound of Formula 15 Where $R^3$ is Nitro

An optionally substituted nitrophenyl pyridolactam compound (Formula 14) as prepared in the previous step is dissolved or suspended in about 2 to 6 molar equivalent, preferably about 3 molar equivalent, dilute acid (such as, hydrochloric acid, hydrobromic acid, sulfuric acid, preferably hydrochloric acid) and heated to reflux for about 4 hours to about 48 hours, preferably about 24 hours. The optionally substituted nitrophenyl pyridolactone compound (Formula 15 where X is nitrogen, Y is carbon, and $R^3$ is nitro) is isolated by filtration or neutralization and extraction, followed by crystallization or chromatography, preferably filtration.

Preparation of a Compound of Formula I, Where $R^1$ is Hydrogen and $R^3$ is Nitro An optionally substituted nitrophenyl pyridolactone compound (Formula 15) is mixed with a solvent inert and miscible with hydrazine (e.g., methanol, ethanol, dimethylformamide, preferably methanol) and heated to a temperature in the range of about room temperature to about 80° C., preferably about 65° C. After stirring the reaction for a period of about 1 hour to about 24 hours, preferably about 18 hours, an optionally substituted nitrophenyl pyridopyridazinone (Formula I where X is nitrogen, Y is carbon, Z is oxygen, $R^1$ is hydrogen, and $R^3$ is nitro) is isolated by filtration.

Preparation of a Compound of Formula I Where $R^1$ is Aryl, Aralkyl, Heterocyclo, Heterocyclo Lower-Alkyl, Heteroaryl, or Heteroaralkyl and $R^3$ is Nitro An optionally substituted nitrophenyl pyridopyridazinone (Formula I where X is nitrogen, Y is carbon, $R^1$ is hydrogen and $R^3$ is nitro) is dissolved in an aprotic solvent (e.g., tetrahydrofuran, dimethylformamide, dimethylacetamide, preferably dimethylformamide) and treated with a base (e.g., sodium hydride, potassium hydride, preferably sodium hydride). The resulting solution is heated to a temperature in the range of about room temperature to about 95° C., preferably about 65° C. About 1.2 molar equivalent of an optionally substituted aryl, aralkyl, heterocyclo, heterocyclo lower-alkyl, heteroaryl, or heteroaralkyl alkylating reagent (Formula 16, where $R^8$ is aryl, aralkyl, heterocyclo, heterocyclo lower-alkyl, heteroaryl, or heteroaralkyl) is added. The resulting optionally substituted nitrophenyl heterocyclo, heterocyclo lower-alkyl, heteroaryl, or heteroaralkyl pyridopyridazinone (Formula I where X is nitrogen, Y is carbon, Z is oxygen, $R^1$ is heterocyclo, heterocyclo lower-alkyl, heteroaryl, or heteroaralkyl and $R^3$ is nitro) is isolated by crystallization or chromatography, preferably crystallization.

Preparation of a Compound of Formula I Where $R^1$ is Aryl, Aralkyl, Heterocyclo, Heterocyclo Lower-Alkyl, Heteroaryl, or Heteroaralkyl Hetero-Oxide and $R^3$ is Nitro An optionally substituted nitrophenyl aryl, aralkyl, heterocyclo, heterocyclo lower-alkyl, heteroaryl, or heteroaralkyl pyridopyridazinone (Formula I where X is nitrogen, Y is carbon, $R^1$ is aryl, aralkyl, heterocyclo, heterocyclo lower-alkyl, heteroaryl, or heteroaralkyl and $R^3$ is nitro) is dissolved in a solvent compatible with peroxyacid (e.g., ethyl acetate, toluene, methylene chloride, acetic acid, preferably methylene chloride) and a peroxyacid (such as, m-chloroperoxybenzoic acid, peroxyacetic acid, trifluoroperoxyacetic acid, magnesium monoperoxy-phthalate, preferably m-chloroperoxybenzoic acid) is added. The resulting mixture is stirred for a period of about 1 hour to about 48 hours, preferably about 18 hours at a temperature in the range of about 0° C. to about 50° C., preferably room temperature. The resulting optionally substituted nitrophenyl heterocyclo, heterocyclo lower-alkyl, heteroaryl, or heteroaralkyl hetero-oxide pyridopyridazinone (Formula I, where X is nitrogen, Y is carbon, Z is oxygen, $R^1$ is aryl, aralkyl, heterocyclo, heterocyclo lower-alkyl, heteroaryl, or heteroaralkyl hetero-oxide and $R^3$ is nitro) is isolated by crystallization or chromatography, preferably crystallization.

REACTION SCHEME F

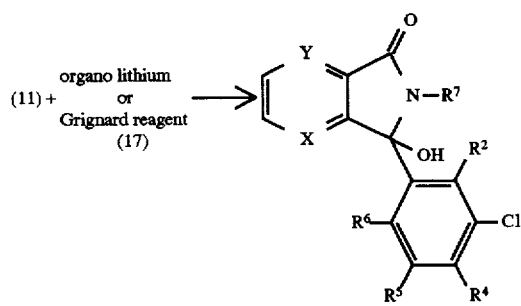

(18)

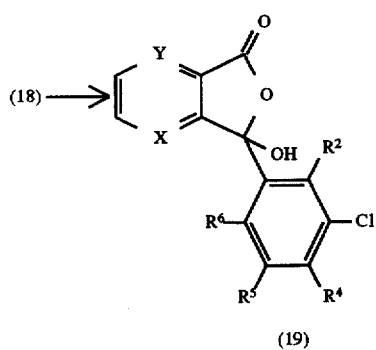

(19)

Formula I, where
$R^1$ is hydrogen and
$R^3$ is chloro

-continued
REACTION SCHEME F

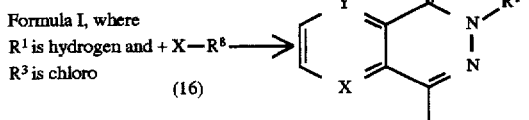

Formula I, where
$R^1$ is hydrogen and + X—$R^8$ ⟶
$R^3$ is chloro
(16)

Formula I, where
$R^1$ is heteroaryl and
$R^3$ is chloro

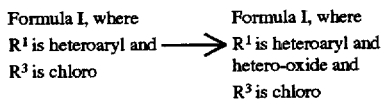

Formula I, where            Formula I, where
$R^1$ is heteroaryl and ⟶   $R^1$ is heteroaryl and
$R^3$ is chloro              hetero-oxide and
                             $R^3$ is chloro Preparation of a Compound of Formula 18 Where $R^3$ is Chloro An optionally substituted m-chlorophenyl pyridolactam is made by following the procedure for preparing Formula 13 set forth in Reaction Scheme F. An optionally substituted m-chloro Grignard reagent or organolithium reagent (Formula 17) is used in lieu of Formula 12, resulting in the desired optionally substituted m-chlorophenyl pyridolactam (Formula 18, where X is nitrogen, Y is carbon and $R^3$ is chloro).

Preparation of a Compound of Formula 19 Where $R^3$ is Chloro

An optionally substituted m-chlorophenyl pyridolactone (Formula 19 where $R^3$ is chloro) is prepared by following the procedure for preparing Formula 15 set forth in Reaction Scheme F.

Preparation of Compound of Formula I Where $R^1$ is Hydrogen and $R^3$ is Chloro An optionally substituted m-chlorophenyl pyridopyridazinone (Formula I where $R^1$ is hydrogen and $R^3$ is chloro) is prepared by following the procedure for preparing Formula I where $R^1$ is hydrogen and $R^3$ is nitro set forth in Reaction Scheme F.

Preparation of a Compound of Formula I Where $R^1$ is Aryl, Aralkyl, Heterocyclo, Heterocyclo Lower-Alkyl, Heteroaryl, or Heteroaralkyl and $R^3$ is Chloro An optionally substituted m-chlorophenyl aryl, aralkyl, heterocyclo, heterocyclo lower-alkyl, heteroaryl, or heteroaralkyl pyridopyridazinone (Formula I where R¹ is aryl, aralkyl, heterocyclo, heterocyclo lower-alkyl, heteroaryl, or heteroaralkyl and R³ is chloro) is prepared by following the procedure for preparing Formula I where R¹ is aryl, aralkyl, heterocyclo, heterocyclo lower-alkyl, heteroaryl, or heteroaralkyl and R³ is nitro set forth in Reaction Scheme F.

Preparation of a Compound of Formula I Where R¹ is Aryl, Aralkyl, Heterocyclo, Heterocyclo Lower-Alkyl, Heteroaryl, or Heteroaralkyl Hetero-Oxide and R³ is Chloro An optionally substituted m-chlorophenyl aryl, aralkyl, heterocyclo, heterocyclo lower-alkyl, heteroaryl, or heteroaralkyl hetero-oxide pyridopyridazinone (Formula I where R¹ is aryl, aralkyl, heterocyclo, heterocyclo lower-alkyl, heteroaryl, or heteroaralkyl and R³ is chloro) is prepared by following the procedure for preparing Formula I where R¹ is aryl, aralkyl, heterocyclo, heterocyclo lower-alkyl, heteroaryl, or heteroaralkyl hetero-oxide and R³ is nitro set forth in Reaction Scheme F.

PREFERRED COMPOUNDS

Presently preferred are the compound of Formula I where X is nitrogen, Y is carbon, Z is oxygen, R³ is chloro or nitro and R¹ is ethyl, 2-propyl, 4-pyridyl- methyl, 4-pyridyl-N-oxide-methyl, 3-pyridylmethyl, 3-pyridyl-N-oxide-methyl, benzyl, 3-thienylmethyl or cyclopentylmethyl.

Preferred are the compounds of Formula I where R³ is chloro and R¹ is ethyl, 4-pyridylmethyl, 4-pyridyl-N-oxide-methyl, 3-pyridylmethyl, 3-pyridyl-N-oxide-methyl, benzyl or 3-thienylmethyl;

particularly the compounds where R², R⁴, R⁵ and R⁶ are hydrogen.

Similarly preferred are the compounds of Formula I where R³ is nitro and R¹ is 4-pyridylmethyl, 4-pyridyl-N-oxide-methyl, 3-pyridylmethyl, 3-pyridyl-N-oxide-methyl, benzyl, 3-thienylmethyl, 2-propyl or cyclopentyl;

particularly the compounds where R², R⁴, R⁵ and R⁶ are hydrogen.

Most preferred are the compounds 6-(4-pyridylmethyl)-8-(3- nitrophenyl)-pyrido[2,3-d]-pyridazin-5-one, 6-(4-pyridyl-N-oxide-methyl)-8-(3-nitrophenyl)-pyrido[2,3-d]pyridazin-5-one, 6-(3-pyridylmethyl)-8-(3-nitrophenyl)-pyrido[2,3-d]pyridazin-5-one, 6-(3-pyridyl-N-oxide-methyl)-8-(3- nitrophenyl)-pyrido[2,3-d]pyridazin-5-one, 6-benzyl-8-(3-nitrophenyl)-pyrido[2,3-d]pyridazin-5-one, 6-ethyl-8-(3-nitrophenyl)-pyrido[2,3-d]pyridazin-5-one and 6-(3-thienylmethyl)-8-(3-nitrophenyl)-pyrido[2,3-d]-pyridazin-5-one.

Also most preferred are the compounds 6-(4-pyridyl-methyl)-8-(3-chlorophenyl)-pyrido[2,3-d]pyridazin-5-one, 6-(4-pyridyl-N-oxide-methyl)-8-(3-chlorophenyl)-pyrido[2,3-d]pyridazin-5-one, 6-(3-pyridylmethyl)-8-(3-chlorophenyl)-pyrido[2,3-d]pyridazin-5-one, 6-(3-pyridyl-methyl)-8-(3-chlorophenyl)-pyrido[2,3-d]pyridazin-5-one, 6-benzyl-8-(3-chloro-phenyl)-pyrido[2,3-d]pyridazin-5-one, 6-(2-propyl)-8-(3-chlorophenyl)-pyrido[2,3-d]pyridazin-5-one, 6-cyclopentyl-8-(3-chlorophenyl)-pyrido[2,3-d]-pyridazin-5-one, and 6-(3-thienylmethyl)-8-(3-chlorophenyl)-pyrido[2,3-d]pyridazin-5-one.

PREFERRED PROCESSES AND LAST STEPS

A preferred process for making optionally substituted pyrido[2,3-d]pyridazin-5-one, pyrido-[2,3-d]pyridazin-8-one or benzopyridazin-1-one compounds entails contacting a suitably substituted 2-benzoyl-3-methoxycarbonylpyridine with a suitably substituted hydrazine.

A preferred process for making optionally substituted 2-benzoyl-3-methoxycarbonylpyridine entails contacting a suitably substituted 2-benzoyl-3-carboxypyridine with an esterification reagent.

A preferred process for making optionally substituted 2-benzoyl-3-carboxypyridine entails contacting a suitably substituted benzo or pyridodicarboxylic anhydride with a suitably substituted Grignard reagent.

A preferred process for making 6-substituted pyrido[2,3-d]pyridazin-5-one entails contacting of the 6-unsubstituted pyrido[2,3-d]pyridazin-5-one with a suitable base, followed by the addition of an alkylating agent.

A preferred process for making 7-substituted pyrido[2,3-d]pyridazin-8-one entails contacting of the 7-unsubstituted pyrido[2,3-d]pyridazin-8-one with a suitable base, followed by the addition of an alkylating agent.

A preferred process for making 2-substituted benzopyridazin-1-one entails contacting of the 2-unsubsituted benzopyridazin-1-one with a suitable base, followed by the addition of an alkylating agent.

A preferred process for making 6-substituted pyrido[2,3-d]pyridazin-5-one entails contacting the 6-unsubstituted pyrido[2,3-d]pyridazin-5-one compound with a suitably substituted alcohol and triphenyl phosphine, followed by diisopropyl azodicarboxylate (i.e., Mitsunobu reaction conditions).

A preferred process for making 7-substituted pyrido[2,3-d]pyridazin-8-one entails contacting the 7-unsubstituted pyrido[2,3-d]pyridazin-8-one compound with a suitably substituted alcohol and triphenyl phosphine, followed by diisopropyl azodicarboxylate (i.e., Mitsunobu reaction conditions).

A preferred process for making 2-substituted benzopyridazin-1-one entails contacting the 2-unsubstituted benzopyridazin-1-one compound with a suitably substituted alcohol and triphenyl phosphine, followed by diisopropyl azodicarboxylate (i.e., Mitsunobu reaction conditions).

A preferred process for making 6-substituted pyrido-N-oxide-alkyl[2,3-d]pyridazin-5-one entails suspending the 6-unsubstituted pyrido[2,3-d]pyridazin-5-one compound with a suitably substituted pyridylcarbinol N-oxide and triphenylphosphine, followed by diisopropyl azodicarboxylate (i.e., Mitsunobu reaction conditions).

A preferred process for making 7-substituted pyrido-N-oxide-alkyl[2,3-d]pyridazin-8-one entails suspending the 7-unsubstituted pyrido[2,3-d]pyridazin-8-one compound with a suitably substituted pyridylcarbinol N-oxide and triphenylphosphine, followed by diisopropyl azodicarboxylate (i.e., Mitsunobu reaction conditions).

A preferred process for converting a 6,8-disubstituted pyrido[2,3-d]pyridazin-5-one into the corresponding 6,8-disubstituted pyrido[2,3-d]pyridazin-5-thione entails treating the 6,8-disubstituted pyrido[2,3-d]pyridazin-5-one with a reagent for the thiation of ketones (such as Lawesson's Reagent or phosphorus pentasulfide) in an appropriate solvent, preferably at reflux.

UTILITY, TESTING AND ADMINISTRATION

General Utility

The compounds of this invention, including the pharmaceutically acceptable salts and esters thereof, and the compositions containing them are particularly useful as anti-inflammatory, antasthmatc, immunosuppressive, anti-allograft rejection, anti-graft-vs-host disease, autoimmune disease or analgetic agents. The compounds of this invention act as PDE IV selective inhibitors, thereby modulating cAMP levels. Thus, these compounds are of use for the treatment of conditions or diseases that are modulated by leukocyte cAMP.

For example, inflammation, immunosuppression, autoimmune diseases, graft-vs-host disease and allograft rejection are conditions that are manifested by the proliferation of lymphocytes. The proliferation is triggered by the presence of cAMP at specific levels. Inhibition of lymphocyte proliferation is accomplished by increasing levels of cAMP resulting from the inhibition of lymphocyte phosphodiesterase.

Testing

Potency and selectivity of compounds as inhibitors of PDE IV is determined by following, for example, the procedures described in Example 54, or modifications thereof.

The immunomodulatory and anti-inflammatory activity of the compounds of the invention can be determined by a variety of assays utilizing both in vitro and in vivo procedures.

Inhibition of the proliferation of lymphocytes in response to mitogenic stimulation is determined by the procedures described by Greaves, et al. ["Activation of human T and B lymphocytes by polyclonal mitogens," *Nature*, 248, 698–701 (1974)]., or modifications thereof (see, Example 48).

Inhibition of lymphocyte activation in response to antigenic challenge is determined in vitro by inhibition of a cytolytic T-cell assay (CTL) as described by Wunderlich, et al., *Nature* (1970), Vol. 228, p. 62, or a modification thereof.

Immune modulation is determined by in vivo procedures utilizing the Jerne Hemolytic Plaque Assay, [Jerne, et al., "The agar plaque technique for recognizing antibody producing cells," *Cell-bound Antibodies*, Amos, B. and Kaprowski, H. editors (Wistar Institute Press, Philadelphia) 1963, p. 109] or a modification thereof (see, Example 47).

Anti-inflammatory activity is determined by the Arachidonic Acid-Induced Mouse Ear Edema Assay [Young, et al., *J. Invest. Derm.*, 82: 367–371 (1984)] (see, Example 49).

Analgetic activity is determined by the phenylquinone-induced Mouse Writhing Assay [Hendershot, et al., *J. Pharmacol. Exp. Ther.*, 125: 237–240 (1959)].

Administration

The compounds of this invention are administered at a therapeutically effective dosage, i.e., that amount which, when administered to a mammal in need thereof, is sufficient to effect treatment, as described above (for example, to reduce or otherwise treat inflammation, pain and/or pyrexia in the mammal). Administration of the active compounds and salts described herein can be via any of the accepted modes of administration for agents that serve similar utilities.

The level of the drug in a formulation can vary within the full range employed by those skilled in the art, e.g., from about 0.01 percent weight (% w) to about 99.99% w of the drug based on the total formulation and about 0.01% w to 99.99% w excipient. Preferably the drug is present at a level of about 10% w to about 70% w.

Generally, an acceptable daily dose is of about 0.0001 to 150 mg per kilogram body weight of the recipient per day, preferably about 0.01 to 75 mg per kilogram body weight per day, and most preferably about 0.1 to 30 mg per kilogram body weight per day. Thus, for administration to a 70 kg person, the dosage range would be about 0.007 mg to 10.5 g per day, preferably about 0.7 to 5.25 g per day, and most preferably about 7.0 mg to 2.1 g per day.

Administration can be via any accepted systemic or local route, for example, via parenteral, oral (particularly for infant formulations), intravenous, nasal, bronchial inhalation (i.e., aerosol formulation) transdermal or topical routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages. The compositions will include a conventional pharmaceutical carrier or excipient and an active compound of Formula I and, in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical excipient in combination with a compound of Formula I. The level of the drug in a formulation can vary within the full range employed by those skilled in the art, e.g., from about 0.01 percent weight (% w) to about 99.99% w of the drug based on the total formulation and about 0.01% w to 99.99% w excipient. Preferably, the formulation will be about 3.5 to 60% by weight of the pharmaceutically active compound, with the rest being suitable pharmaceutical excipients.

Intravenous Administration

Intravenous injection has proven to be an important route of administration for therapeutic agents. The compounds of the present invention can be administered via this route, for example, by dissolving the compound, salt, ester or ether in a suitable solvent (such as water or saline) or incorporation in a liposomal formulation followed, by dispersal into an acceptable infusion fluid. A typical daily dose of a compound of the invention can be administered by one infusion, or by a series of infusions spaced over periodic intervals.

Oral Administration

Oral administration can be used to deliver the compound of Formula I using a convenient daily dosage regimen which can be adjusted according to the degree of affliction or for renal impairment, or to compensate for the toxic effects of other medications administered contemporaneously. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt/wt % and 99.99 wt/wt % of the compound of Formula I, but preferably such compositions will contain between 25 wt/wt % and about 80 wt/wt %.

Preferably the compositions will take the form of a capsule, pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, polyvinylpyrrolidone, gum acacia, gelatin, cellulose and derivatives thereof, and the like. For oral administration to infants, a liquid formulation (such as a syrup or suspension) is preferred.

Aerosol Administration

Aerosol administration is an effective means for delivering a therapeutic agent directly to the respiratory tract. Some of the advantages of this method are: 1) it circumvents the effects of enzymatic degradation, poor absorption from the gastrointestinal tract, or loss of the therapeutic agent to the hepatic first-pass effect; 2) it administers therapeutic agents which would otherwise fail to reach their target sites in the respiratory tract due to their molecular size, charge or affinity to extra-pulmonary sites; 3) it provides for fast absorption into the body via the aveoli of the lungs; and 4) it avoids exposing other organ systems to the therapeutic agent, which is important where exposure might cause undesirable side effects. For these reasons, aerosol administration is particularly advantageous for treatment of asthma, local infections of the lung, and other diseases or disease conditions of the lung and respiratory tract.

There are three types of pharmaceutical inhalation devices, nebulizers inhalers, metered-dose inhalers (MDI) and dry powder inhalers (DPI). Nebulizer devices produce a stream of high velocity air that causes the therapeutic agent (which has been formulated in a liquid form) to spray as a mist which is carried into the patient's respiratory tract. MDIs typically have the formulation packaged with a compressed gas. Upon actuation, the device discharges a measure amount of therapeutic agent by compressed gas, thus affording a reliable method of administering a set amount of agent. Historically, MDIs have used chlorofluorocarbons (CFC) as the compressed gas to propel the therapeutic agent. In recent years, CFCs have been linked with the depletion of the earth's ozone layer. As a result of this, alternative propellants that are non-ozone threatening are being sought out as potential replacements for CFCs.

DPIs administer therapeutic agents in the form of a free flowing powder that can be dispersed in the patient's inspiratory air-stream during breathing by the device. In order to achieve a free flowing powder, the therapeutic agent is formulated with an excipient, such as lactose. A measured amount of the therapeutic is stored in a capsule form and is dispensed to with each actuation. Examples of DPIs being used are Spinbaler® (for the administration of disodium cromoglycate), Rotahaler® (for albuterol) and Turbuhaler® (for terbutaline sulfate). All of the above methods can be used for administering the present invention, particularly for the treatment of asthma and other similar or related respiratory tract disorders.

Liposomal Formulations

Pharmaceutical formulations based on liposomes have recently reached human clinical trials. Their benefits are believed related to favorable changes in tissue distribution and pharmacokinetic parameters that result from liposome entrapment of drugs, and may be applied to the compounds of the present invention by those skilled in the art.

The formulations can be designed to either target drug to disease sites [see: Lopez-Berestein et al., *J. Infect. Dis.*, 151: 704–710 (1985); Gotfredsen et al., *Biochemical Pharmacology*, 32: 3389–3396 (1983)]; or to the reticuloendothelial system [see Eppstein et al., *Int. J. Immunotherapy*, 2: 115–126 (1986)], to increase duration of drug action [see: Gabizon et al., *Cancer Res.*, 42: 4734 (1982); Eppstein et al., *Delivery Systems for Peptide Drugs*, Eds. S. S. Davis, L. Illum and E. Tomlinson, Plenum Pub. Corp., New York, pp. 277–283; C. A. Hunt, *Biochemica et Biophysica Acta.*, 719: 450–463 (1982); and Senior et al., *Biochemica et Biophysica Acta.*, 839: 1–8 (1985)], or to divert a drug away from organs that are particularly sensitive to its toxic effects [see: Weinstein et al., *Pharmac. Ther.*, 24: 207–233 (1983); Olson et al., *Eur. J. Cancer Clin. Oncol.*, 18: 167–176 (1982); and Gabzion et al., supra.].

Controlled release liposomal liquid pharmaceutical formulations for injection or oral administration are described in U.S. Pat. No. 4,016,100. Liposomal applications for oral drug delivery of a lyophilized liposome/peptide drug mixture filled into intestine capsules have also been suggested, see U.S. Pat. No. 4,348,384. The foregoing are incorporated herein by reference.

Suppositories

For systemic administration via suppository, traditional binders and carriers include, for example, polyalkaline glycol or triglycerides [e.g., PEG 1000 (96%) and PEG 4000 (4%)]. Such suppositories may be formed from mixtures containing active ingredients in the range of from about 0.5 wt/wt % to about 10 wt/wt %; preferably from about 1 wt/wt % to about 2 wt/wt %.

Liquids

Liquid pharmaceutically administrable compositions can, for example, be prepared by dissolving, dispersing, etc. an active compound (about 0.5% to about 20%), as described above, and optional pharmaceutical adjuvants in a carrier, such as, for example, water, saline, aqueous dextrose, glycerol, ethanol and the like, to thereby form a solution or suspension.

Actual methods of preparing such dosage forms are known, or will be apparent, to those skilled in this art; for example, see *Remington's Pharmaceutical Sciences*, Mack Publishing Company, Easton, Pa., 16th Ed., 1980. The composition to be administered will, in any event, contain a quantity of the active compound(s) in a pharmaceutically effective amount for relief of the particular condition being treated in accordance with the teachings of this invention.

EXAMPLES

The following preparations and examples are given to enable those skilled in the art to more clearly understand and

Example 1

Preparation of 7-(3-nitrophenyl)-furo-[3,4-b]pyridin-5-one

1A. Formula 4, Where X is nitrogen, Y is carbon, $R^3$ is nitro, and $R^2$, $R^4$, $R^5$ and $R^6$ are hydrogen

A solution of 2,3-pyridinyldicarboxylic anhydride (20 g, 134 mmoles) in 25 ml of anhydrous methanol was refluxed for 30 minutes. The methanol was removed and the two positional isomers (2-carboxy-3-methoxycarbonylpyridine and 2-methoxycarbonyl-3-carboxypyridine) are isolated and separated. The 2-carboxy-3-methoxycarbonyl pyridine was added to a solution of 3-nitrobenzaldehyde (101.35 g, 670 mmoles) in p-cymene (105 ml, 670 mmoles) and heated at 180° C. for 13.5 hours. The solution was cooled, filtered and the excess 3-nitrobenzaldehyde and p-cymene removed by bulb to bulb distillation using a Kugelrohr apparatus. The residue was triturated with methylene chloride and the solid residue was discarded. The product was isolated from the filtrate yielding 12.7 g of 7-(3-nitrophenyl)-furo[3,4-b]pyridin-5-one (37.2%).

1B. Preparation of Other Compounds of Formula 4, Where X is nitrogen and Y is carbon

By following the procedures of Example 1A and substituting for 3-nitrobenzaldehyde with the following:
3-methoxybenzaldehyde;
4-methoxybenzaldehyde;
4-methylbenzaldehyde;
3-bromobenzaldehyde;
3-chlorobenzaldehyde;
3-nitro-4-chlorobenzaldehyde;
3-nitro-4-methylbenzaldehyde;
3-methoxycarbonylbenzaldehyde;
4-methoxycarbonylbenzaldehyde;
3-methoxycarbonyl-4-methyl-benzaldehyde;
4-carboxybenzaldehyde;
4-carbamoylbenzaldehyde;
4-N,N-dimethylcarbamoylbenzaldehyde; and
3,4-methylenedioxybenzaldehyde;
there are obtained the following respective compounds:
7-(3-methoxyphenyl)-furo[3,4-b]pyridin-5-one;
7-(4-methoxyphenyl)-furo[3,4-b]pyridin-5-one;
7-(4-methylphenyl)-furo[3,4-b]pyridin-5-one;
7-(3-bromophenyl)-furo[3,4-b]pyridin-5-one;
7-(3-chlorophenyl)-furo[3,4-b]pyridin -5-one;
7-(3-nitro-4-chlorophenyl)-furo[3,4-b]pyridin-5-one;
7-(3-nitro-4-methylphenyl)-furo[3,4-b]pyridin-5-one;
7-(3-methoxycarbonylphenyl)-furo[3,4-b]pyridin-5-one;
7-(4-methoxycarbonylphenyl)-furo[3,4-b]pyridin-5-one;
7-(3-methoxycarbonylphenyl-4-methyl)-furo-[3,4-b]pyridin-5-one;
7-(4-carboxyphenyl)-furo[3,4-b]pyridin-5-one;
7-(4-carbamoylphenyl)-furo[3,4-b]pyridin-5-one;
7-(4-N,N-dimethylcarbamoylphenyl)-furo-[3,4-b]pyridin-5-one; and
7-(3,4-methylenedioxyphenyl)-furo[3,4-b]pyridin-5-one.

Example 2

Preparation of 2-(hydroxymethyl-3-nitrophenyl)-3-carboxypyridine

2A. Formula 5, Where X is nitrogen, Y is carbon, $R^3$ is nitro and $R^2$, $R^4$, $R^5$ and $R^6$ are hydrogen

7-(3-nitrophenyl)-furo[3,4-b]pyridin-5-one was suspended in methanol (100 ml), solid potassium hydroxide (4.5 gm, 80 mmoles) was added and the mixture refluxed for 6 hours under an inert atmosphere yielding 2-(hydroxymethyl-3-nitrophenyl)-3-carboxypyridine.

2B. Preparation of Other Compounds of Formula 5 Where X is nitrogen and Y is carbon

By following the procedures of Example 2A and substituting for 7-(3-nitrophenyl)-furo[3,4-b]pyridin-5-one with the following:
7-(3-methoxyphenyl)-furo[3,4-b]pyridin-5-one;
7-(4-methoxyphenyl)-furo[3,4-b]pyridin-5-one;
7-(4-methylphenyl)-furo[3,4-b]pyridin-5-one;
7-(3-bromophenyl)-furo[3,4-b]pyridin-5-one;
7-(3-chlorophenyl)-furo[3,4-b]pyridin-5-one;
7-(3-nitro-4-chlorophenyl)-furo[3,4-b]pyridin-5-one;
7-(3-nitro-4-methylphenyl)-furo[3,4-b]pyridin-5-one;
7-(3-methoxycarbonylphenyl)-furo[3,4-b]pyridin-5-one;
7-(4-methoxycarbonylphenyl)-furo[3,4-b]pyridin-5-one;
7-(3-methoxycarbonyl-4-methylphenyl)-furo-[3,4-b]-pyridin-5-one;
7-(4-carboxyphenyl)-furo[3,4-b]pyridin-5-one;
7-(4-carbamoylphenyl)-furo[3,4-b]pyridin-5-one;
7-(4-N,N-dimethylcarbamoylphenyl)-furo-[3,4-b]-pyridin-5-one; and
7-(3,4-methylenedioxyphenyl)-furo[3,4-b]pyridin-5-one;
there are obtained the following compounds:
2-(hydroxymethyl-3-methoxyphenyl)-3-carboxypyridine;
2-(hydroxymethyl-4-methoxyphenyl)-3-carboxypyridine;
2-(hydroxymethyl-4-methylphenyl)-3-carboxypyridine;
2-(hydroxymethyl-3-bromophenyl)-3-carboxypyridine;
2-(hydroxymethyl-3-chlorophenyl)-3-carboxypyridine;
2-(hydroxymethyl-3-nitro-4-chlorophenyl)-3-carboxypyridine;
2-(hydroxymethyl-3-nitro-4-methylphenyl)-3-carboxypyridine;
2-(hydroxymethyl-3-methoxycarbonylphenyl)-3-carboxypyridine;
2-(hydroxymethyl-4-methoxycarbonylphenyl)-3-carboxypyridine;
2-(hydroxymethyl-3-methoxycarbonyl-4-methylphenyl)-3-carboxypyridine;
2-(hydroxymethyl-4-carboxyphenyl)-3-carboxypyridine;
2-(hydroxymethyl-4-carbamoylphenyl)-3-carboxypyridine;
2-(hydroxymethyl-4-N,N-dimethylcarbamoyl-phenyl)-3-carboxypyridine; and
2-(hydroxymethyl-3,4-methylenedioxyphenyl)-3-carboxypyridine.

Example 3

Preparation of 2-(3-nitrobenzoyl)-3-carboxypyridine

3A. Formula 6, Where X is nitrogen, Y is carbon, $R^3$ is nitro and $R^2$, $R^4$, $R^5$ and $R^6$ are hydrogen

To a solution of 2-(hydroxymethyl-3-nitrophenyl)-3-carboxypyridine (2.25 g, 8.2 mmoles) in methylene chloride (20 ml), pyridinium dichromate (4.63 g, 12.3 mmoles) was added and stirred at room temperature (22° C.) for 18 hours. The solution was filtered and the solvent removed yielding 3.43 g of crude 2-(3-nitro-benzoyl)-3-carboxypyridine.

3B. Preparation of Other Compounds of Formula 6 Where X is nitrogen and Y is carbon

By following the procedures of Example 3A and substituting for 2-(hydroxymethyl-3-nitrophenyl)-3-carboxypyridine with the following:

2-(hydroxymethyl-3-methoxyphenyl)-3-carboxypyridine;
2-(hydroxymethyl-4-methoxyphenyl)-3-carboxypyridine;
2-(hydroxymethyl-4-methylphenyl)-3-carboxypyridine;
2-(hydroxymethyl-3-bromophenyl)-3-carboxypyridine;
2-(hydroxymethyl-3-chlorophenyl)-3-carboxypyridine;
2-(hydroxymethyl-3-nitro-4-chlorophenyl)-3-carboxypyridine;
2-(hydroxymethyl-3-nitro-4-methylphenyl)-3-carboxypyridine;
2-(hydroxymethyl-3-methoxycarbonylphenyl)-3-carboxypyridine;
2-(hydroxymethyl-4-methoxycarbonylphenyl)-3-carboxypyridine;
2-(hydroxymethyl-3-methoxycarbonyl-4-methylphenyl)-carboxypyridine;
2-(hydroxymethyl-4-carboxyphenyl)-3-carboxypyridine;
2-(hydroxymethyl-4-carbamoylphenyl)-3-carboxypyridine;
2-(hydroxymethyl-4-N,N-dimethylcarbamoyl-phenyl)-3-carboxypyridine; and
2-(hydroxymethyl-3,4-methylenedioxyphenyl)-3-carboxypyridine;
there are obtained the following compounds:
2-(3-methoxybenzoyl)-3-carboxypyridine;
2-(4-methoxybenzoyl)-3-carboxypyridine;
2-(4-methylbenzoyl)-3-carboxypyridine;
2-(3-bromobenzoyl)-3-carboxypyridine;
2-(3-chlorobenzoyl)-3-carboxypyridine;
2-(3-nitro-4-chlorobenzoyl)-3-carboxypyridine;
2-(3-nitro-4-methylbenzoyl)-3-carboxypyridine;
2-(3-methoxycarbonylbenzoyl)-3-carboxypyridine;
2-(4-methoxycarbonylbenzoyl)-3-carboxypyridine;
2-(3-methoxycarbonyl-4-methylbenzoyl)-3-carboxypyridine;
2-(4-carboxybenzoyl)-3-carboxypyridine;
2-(4-carbamoylbenzoyl)-3-carboxypyridine;
2-(4-N,N-dimethylcarbamoylbenzoyl)-3-carboxypyridine; and
2-(3,4-methylenedioxybenzoyl)-3-carboxypyridine.

Example 4

Preparation of 2-(3-nitrobenzoyl)-3-methoxycarbonylpyridine

4A. Formula II, Where X is nitrogen, Y is carbon, $R^3$ is nitro and $R^2$, $R^4$, $R^5$ and $R^6$ are hydrogen 2-(3-Nitrobenzoyl)-3-carboxypyridine was dissolved in 20 ml of methylene chloride and the solution was cooled in an ice/water bath. Diazomethane (25 ml, 0.33M) was added to the solution and stirred for 2 hours. The solvent was removed and the residue chromatographed (methylene chloride) yielding 0.26 g of 2-(3-nitrobenzoyl)-3-methoxycarbonylpyridine.

4B. Preparation of Other Compounds of Formula II Where X is nitrogen and Y is carbon By following the procedures of Example 4A and substituting for 2-(3-Nitrobenzoyl)-3-carboxypyridine with the following:
2-(3-methoxybenzoyl)-3-carboxypyridine;
2-(4-methoxybenzoyl)-3-carboxypyridine;
2-(4-methylbenzoyl)-3-carboxypyridine;
2-(3-bromobenzoyl)-3-carboxypyridine;
2-(3-chlorobenzoyl)-3-carboxypyridine;
2-(3-nitro-4-chlorobenzoyl)-3-carboxypyridine;
2-(3-nitro-4-methylbenzoyl)-3-carboxypyridine;
2-(3-methoxycarbonylbenzoyl)-3-carboxypyridine;
2-(4-methoxycarbonylbenzoyl)-3-carboxypyridine;
2-(3-methoxycarbonyl-4-methylbenzoyl)-3-carboxypyridine;
2-(4-carboxybenzoyl)-3-carboxypyridine;
2-(4-carbamoylbenzoyl)-3-carboxypyridine;
2-(4-N,N-dimethylcarbamoylbenzoyl)-3-carboxypyridine; and
2-(3,4-methylenedioxybenzoyl)-3-carboxypyridine;
there are obtained the following compounds:
2-(3-methoxybenzoyl)-3-methoxycarbonylpyridine;
2-(4-methoxybenzoyl)-3-methoxy-carbonylpyridine;
2-(4-methylbenzoyl)-3-methoxy-carbonylpyridine;
2-(3-bromobenzoyl)-3-methoxy-carbonylpyridine;
2-(3-chlorobenzoyl)-3-methoxycarbonylpyridine;
2-(3-nitro-4-chlorobenzoyl)-3-methoxycarbonylpyridine;
2-(3-nitro-4-methylbenzoyl)-3-methoxycarbonylpyridine;
2-(3-methoxycarbonylbenzoyl)-3-methoxycarbonylpyridine;
2-(4-methoxycarbonylbenzoyl)-3-methoxycarbonylpyridine;
2-(3-methoxycarbonyl-4-methylbenzoyl)-3-methoxycarbonylpyridine;
2-(4-carboxybenzoyl)-3-methoxycarbonylpyridine;
2-(4-carbamoylbenzoyl)-3-methoxycarbonylpyridine;
2-(4-N,N-dimethylcarbamoylbenzoyl)-3-methoxycarbonylpyridine; and
2-(3,4-methylenedioxybenzoyl)-3-methoxycarbonylpyridine.

Example 5

Preparation of 8-(3-nitrophenyl)-pyrido[2,3-d]pyridazin-5-one

5A. Formula I, Where X is nitrogen, Y is carbon, Z is oxygen, $R^3$ is nitro and $R^1$, $R^2$, $R^4$, $R^5$ and $R^6$ are hydrogen To a solution of 2-(3-nitrobenzoyl)-3-methoxycarbonylpyridine (0.58 g, 2 mmoles) dissolved in ethanol (50 ml), was added hydrazine monohydrate (0.25 ml, 5.1 mmoles). The mixture was refluxed for 4 hours, cooled and ethyl acetate (50 ml) was added. The solid material was collected and dried, yielding 0.58 g of 8-(3-nitrophenyl)-pyrido[2,3-d]pyridazin-5-one, mp 302° C.

5B. Preparation of Other Compounds of Formula I Where X is nitrogen, Y is carbon, and Z is oxygen By following the procedures of Example 5A and substituting for 2-(3-nitrobenzoyl)-3-methoxycarbonylpyridine with the following:
2-(3-methoxybenzoyl)-3-methoxycarbonylpyridine;
2-(4-methoxybenzoyl)-3-methoxycarbonylpyridine;
2-(4-methylbenzoyl)-3-methoxycarbonylpyridine;
2-(3-bromobenzoyl)-3-methoxycarbonylpyridine;
2-(3-chlorobenzoyl)-3-methoxycarbonylpyridine;
2-(3-nitro-4-chlorobenzoyl)-3-methoxycarbonylpyridine;
2-(3-nitro-4-methylbenzoyl)-3-methoxycarbonylpyridine;
2-(3-methoxycarbonylbenzoyl)-3-methoxycarbonylpyridine;
2-(4-methoxycarbonylbenzoyl)-3-methoxycarbonylpyridine;
2-(3-methoxycarbonyl-4-methylbenzoyl)-3-methoxycarbonylpyridine;
2-(4-carboxybenzoyl)-3-methoxycarbonylpyridine;
2-(4-carbamoylbenzoyl)-3-methoxycarbonylpyridine;
2-(4-N,N-dimethylcarbamoylbenzoyl)-3-methoxycarbonylpyridine; and 2-(3,4-methylenedioxybenzoyl)-3-methoxycarbonylpyridine;

there are obtained the following compounds:

8-(3-methoxyphenyl)-pyrido[2,3-d]pyridazin-5-one;
8-(4-methoxyphenyl)-pyrido[2,3-d]pyridazin-5-one;
8-(4-methylphenyl)-pyrido[2,3-d]pyridazin-5-one;
8-(3-bromophenyl)-pyrido[2,3-d]pyridazin-5-one;
8-(3-chlorophenyl)-pyrido[2,3-d]pyridazin-5-one;
8-(3-nitro-4-chlorophenyl)-pyrido[2,3-d]-pyridazin-one;
8-(3-nitro-4-methylphenyl)-pyrido[2,3-d]pyridazin-one;
8-(3-methoxycarbonylphenyl)-pyrido[2,3-d]pyridazin-one;
8-(4-methoxycarbonylphenyl)-pyrido[2,3-d]pyridazin-one;
8-(3-methoxycarbonyl-4-methylphenyl)-pyrido[2,3-d]pyridazin-5-one;
8-(4-carboxyphenyl)-pyrido[2,3-d]pyridazin-5-one;
8-(4-carbamoylphenyl)-pyrido[2,3-d]pyridazin-5-one;
8-(4-N,N-dimethyl carbamoylphenyl)-pyrido[2,3-d]pyridazin-5-one; and
8-(3,4-methylenedioxyphenyl)-pyrido[2,3-d]pyridazin-5-one.

Example 6

Preparation of 6-phenyl-8-(3-nitrophenyl)pyrido [2,3-d]pyridazin-5-one

6A. Formula I, Where X is nitrogen, Y is carbon, Z is oxygen, $R^1$ is phenyl, $R^3$ is nitro and $R^2$, $R^4$, $R^5$ and $R^6$ are hydrogen To a solution of 2-(3-nitrobenzoyl)-3-methoxycarbonylpyridine (0.26 g, 0.97 mmoles) dissolved in ethanol (50 ml), was added phenylhydrazine (0.25 ml, 2.4 mmoles). The mixture was refluxed for 168 hours. The solvent was removed and the solid was precipitated from ethanol and dried, yielding 0.07 g of 6-phenyl-8-(3-nitrophenyl) pyrido[2,3-d]pyridazin-5-one (21%), mp 167° C.

6B. Preparation of Other Compounds of Formula I
Where X is nitrogen, Y is carbon, and Z is oxygen By following the procedures of Example 6A and substituting for 2-(3-nitrobenzoyl)-3-methoxycarbonylpyridine with the following:

2-(3-methoxybenzoyl)-3-methoxycarbonylpyridine;
2-(4-methoxybenzoyl)-3-methoxycarbonylpyridine;
2-(4-methylbenzoyl)-3-methoxycarbonylpyridine;
2-(3-bromobenzoyl)-3-methoxycarbonylpyridine;
2-(3-chlorobenzoyl)-3-methoxycarbonylpyridine;
2-(3-nitro-4-chlorobenzoyl)-3-methoxycarbonylpyridine;
2-(3-nitro-4-methylbenzoyl)-3-methoxycarbonylpyridine;
2-(3-methoxycarbonylbenzoyl)-3-methoxycarbonylpyridine;
2-(4-methoxycarbonylbenzoyl)-3-methoxycarbonylpyridine;
2-(3-methoxycarbonyl-4-methylbenzoyl)-3-methoxycarbonylpyridine;
2-(4-carboxybenzoyl)-3-methoxycarbonylpyridine;
2-(4-carbamoylbenzoyl)-3-methoxycarbonylpyridine;
2-(4-N,N-dimethylcarbamoylbenzoyl)-3-methoxycarbonylpyridine; and
2-(3,4-methylenedioxybenzoyl)-3-methoxycarbonylpyridine;

there are obtained the following compounds:

6-phenyl-8-(3-methoxyphenyl)-pyrido[2,3-d]pyridazin-5-one;
6-phenyl-8-(4-methoxyphenyl)-pyrido[2,3-d]pyridazin-5-one;
6-phenyl-8-(4-methylphenyl)-pyrido[2,3-d]pyridazin-one;
6-phenyl-8-(3-bromophenyl)-pyrido[2,3-d]pyridazin-one;
6-phenyl-8-(3-chlorophenyl)-pyrido[2,3-d]pyridazin-one;
6-phenyl-8-(3-nitro-4-chlorophenyl)-pyrido-[2,3-d]pyridazin-5-one;
6-phenyl-8-(3-nitro-1-methylphenyl)-pyrido-[2,3-d]pyridazin-5-one;
6-phenyl-8-(3-methoxycarbonylphenyl)-pyrido-[2,3-d]pyridazin-5-one;
6-phenyl-8-(4-methoxycarbonylphenyl)-pyrido-[2,3-d]pyridazin-5-one;
6-phenyl-8-(3-methoxycarbonyl-4-methylphenyl)-pyrido[2,3-d]pyridazin-5-one;
6-phenyl-8-(4-carboxyphenyl)-pyrido[2,3-d]pyridazin-5-one;
6-phenyl-8-(4-carbamoylphenyl)-pyrido-[2,3-d]-pyridazin-5-one;
6-phenyl-8-(4-N,N-dimethylcarbamoylphenyl)-pyrido[2,3-d]pyridazin-5-one; and
6-phenyl-8-(3,4-methylenedioxyphenyl)-pyrido[2,3-d]pyridazin-5-one.

Example 7

Preparation of 6-benzyl-8-(3-nitrophenyl)pyrido-[2,3-d]pyridazin-5-one

7A. Formula I, Where X is nitrogen, Y is carbon, Z is oxygen, $R^1$ is benzyl, $R^3$ is nitro and $R^2$, $R^4$, $R^5$ and $R^6$ are hydrogen To a solution of 2-(3-nitrobenzoyl)-3-methoxycarbonylpyridine (0.20 g, 0.75 mmoles) dissolved in ethanol (50 ml), was added benzylhydrazine hydrochloride (0.36 g, 1.86 mmoles). The mixture was heated to 85° C. for 144 hours. The mixture was purified by chromatography yielding 0.11 g of 6-benzyl-8-(3-nitrophenyl)pyrido [2,3-d]pyridazin-5-one (41%), mp 132° C.

7B. Preparation of Other Compounds of Formula I
Where X is nitrogen, Y is carbon, and Z is oxygen By following the procedures of Example 7A and substituting for 2-(3-nitrobenzoyl)-3-methoxycarbonylpyridine with the following:

2-(3-methoxybenzoyl)-3-methoxycarbonylpyridine;
2-(4-methoxybenzoyl)-3-methoxycarbonylpyridine;
2-(4-methylbenzoyl)-3-methoxycarbonylpyridine;
2-(3-bromobenzoyl)-3-methoxycarbonylpyridine;
2-(3-chlorobenzoyl)-3-methoxycarbonylpyridine;
2-(3-nitro-4-chlorobenzoyl)-3-methoxycarbonylpyridine;
2-(3-nitro-4-methylbenzoyl)-3-methoxycarbonylpyridine;
2-(3-methoxycarbonylbenzoyl)-3-methoxycarbonylpyridine;
2-(4-methoxycarbonylbenzoyl)-3-methoxycarbonylpyridine;
2-(3-methoxycarbonyl-4-methylbenzoyl)-3-methoxycarbonylpyridine;
2-(4- carboxybenzoyl)-3-methoxycarbonylpyridine;
2-(4- carbamoylbenzoyl)-3-methoxycarbonylpyridine;
2-(4-N,N-dimethylcarbamoylbenzoyl)-3-methoxycarbonylpyridine; and
2-(3,4-methylenedioxybenzoyl)-3-methoxycarbonylpyridine;

there are obtained the following compounds:

6-benzyl-8-(3- methoxyphenyl)-pyrido[2,3-d]pyridazin-5-one;
6-benzyl-8-(4-methoxyphenyl)-pyrido[2,3-d]pyridazin-5-one;

6-benzyl-8-(4-methylphenyl)-pyrido[2,3-d]pyridazin-one;
6-benzyl-8-(3-bromophenyl)-pyrido[2,3-d]pyridazin-one;
6-benzyl-8-(3-chlorophenyl)-pyrido[2,3-d]pyridazin-one;
6-benzyl-8-(3-nitro-4-chlorophenyl)-pyrido-[2,3-d]pyridazin-5-one;
6-benzyl-8-(3-nitro-4-methylphenyl)-pyrido-[2,3-d]pyridazin-5-one;
6-benzyl-8-(3-methoxycarbonylphenyl)-pyrido-[2,3-d]pyridazin-5-one;
6-benzyl-8-(4-methoxycarbonylphenyl)-pyrido-[2,3-d]pyridazin-5-one; 6-benzyl-8-(3-methoxycarbonyl-4-methylphenyl)-pyrido[2,3-d]pyridazin-5-one;
6-benzyl-8-(4-carboxyphenyl)-pyrido[2,3-d]pyridazin-5-one;
6-benzyl-8-(4-carbamoylphenyl)-pyrido-[2,3-d]-pyridazin-5-one;
6-benzyl-8-(4-N,N-dimethylcarbamoylphenyl)-pyrido[2,3-d]pyridazin-5-one; and
6-benzyl-8-(3,4-methylenedioxyphenyl)-pyrido[2,3-d]pyridazin-5-one.

Example 8

Preparation of 6-ethyl-8-(3-nitrophenyl)-pyrido[2,3-d]pyridazin-5-one

8A. Formula I, Where X is nitrogen, Y is carbon, Z is oxygen, $R^1$ is ethyl, $R^3$ is nitro and $R^2$, $R^4$, $R^5$ and $R^6$ are hydrogen 8-(3-Nitrophenyl)-pyrido[2,3-d]pyridazin-5-one (0.20 g, 0.75 mmoles), sodium hydride (0.04 g, 0.9 mmoles) and iodoethane (0.3 ml, 3.75 mmoles) was dissolved in 25 ml of tetrahydrofuran and refluxed under a nitrogen atmosphere for 18 hours. The solvent was removed and the product chromatographed and eluted with 100% methylene chloride yielding 0.05 g of 6-ethyl-8-(3-nitrophenyl)pyrido[2,3-d]pyridazin-5-one (22.6%), mp. 138° C.

8B. Preparation of Other Compounds of Formula I Where X is nitrogen, Y is carbon, and Z is oxygen By following the procedures of Example 8A and substituting for 8-(3-nitrophenyl)-pyrido[2,3-d]pyridazin-5-one with the following:
8-(3-methoxyphenyl)-pyrido[2,3-d]pyridazin-5-one;
8-(4-methoxyphenyl)-pyrido[2,3-d]pyridazin-5-one;
8-(4-methylphenyl)-pyrido[2,3-d]pyridazin-5-one;
8-(3-bromophenyl)-pyrido[2,3-d]pyridazin-5-one;
8-(3-chlorophenyl)-pyrido[2,3-d]pyridazin-5-one;
8-(3-nitro-4-chlorophenyl)-pyrido[2,3-d]pyridazin-one;
8-(3-nitro-4-methylphenyl)-pyrido[2,3-d]pyridazin-one;
8-(3-methoxycarbonylphenyl)-pyrido[2,3-d]pyridazin-one;
8-(4-methoxycarbonylphenyl)-pyrido[2,3-d]pyridazin-one;
8-(3-methoxycarbonyl-4-methylphenyl)-pyrido[2,3-d]pyridazin-5-one;
8-(4-carboxyphenyl)-pyrido[2,3-d]pyridazin-5-one;
8-(4-carbamoylphenyl)-pyrido[2,3-d]pyridazin-5-one;
8-(4-N,N-dimethylcarbamoylphenyl)-pyrido[2,3-d]pyridazin-5-one; and
8-(3,4-methylenedioxyphenyl)-pyrido[2,3-d]-pyridazin-5-one;
there are obtained the following compounds:
6-ethyl-8-(3-methoxyphenyl)-pyrido[2,3-d]pyridazin-one;
6-ethyl-8-(4-methoxyphenyl)-pyrido[2,3-d]pyridazin-one;
6-ethyl-8-(4-methylphenyl)-pyrido[2,3-d]pyridazin-5-one;
6-ethyl-8-(3-bromophenyl)-pyrido[2,3-d]pyridazin-5-one;
6-ethyl-8-(3-chlorophenyl)-pyrido[2,3-d]pyridazin-5-one;
6-ethyl-8-(3-nitro-4-chlorophenyl)-pyrido-[2,3-d]pyridazin-5-one;
6-ethyl-8-(3-nitro-4-methylphenyl)-pyrido-[2,3-d]pyridazin-5-one;
6-ethyl-8-(3-methoxycarbonylphenyl)-pyrido-[2,3-d]pyridazin-5-one;
6-ethyl-8-(4-methoxycarbonylphenyl)-pyrido-[2,3-d]pyridazin-5-one;
6-ethyl-8-(3-methoxycarbonyl-4-methylphenyl)-pyrido[2,3-d]pyridazin-5-one;
6-ethyl-8-(4-carboxyphenyl)-pyrido[2,3-d]pyridazin-5-one;
6-ethyl-8-(4-carbamoylphenyl)-pyrido[2,3-d]pyridazin-5-one;
6-ethyl-8-(4-N,N-dimethylcarbamoylphenyl)-pyrido[2,3-d]pyridazin-5-one; and
6-ethyl-8-(3,4-methylenedioxyphenyl)-pyrido-[2,3-d]pyridazin-5-one.

Example 9

Preparation of 6-(4-pyridylmethyl)-8-(3-nitrophenyl)pyrido[2,3-d]pyridazin-5-one 9A. Formula I, Where X is nitrogen, Y is carbon, Z is oxygen, $R^1$ is 4-pyridylmethyl, $R^3$ is nitro and $R^2$, $R^4$, $R^5$ and $R^6$ are hydrogen To a solution of 8-(3-nitrophenyl)-pyrido[2,3-d]pyridazin-5-one (0.16 g, 0.6 moles) in tetrahydrofuran (50 ml) was added potassium carbonate (0.19 g, 7.1 moles), potassium iodide (1.0 g, 6.0 moles) and 4-picolyl chloride (0.98 g, 6.0 mmoles). The mixture was stirred and refluxed under an inert atmosphere for 18 hours. The solvent was removed under vacuum. The residue was partitioned in methanol/ethyl acetate (1:1), chromatographed in 100% hexane followed by 100% ethyl acetate. The remaining solvent was removed yielding 0.58 g of crude 6-(4-pyridylmethyl)-8-(3-nitrophenyl)pyrido[2,3-d]pyridazin-5-one, which was recrystallized from methanol yielding 0.08 g of the pure compound (37.1%), mp. 167°–168° C.

9B. Preparation of Other Compounds of Formula I Where X is nitrogen, Y is carbon, and Z is oxygen By following the procedures of Example 9A and substituting for 8-(3-nitrophenyl)-pyrido[2,3-d]pyridazin-5-one with the following:
8-(3-methoxyphenyl)-pyrido[2,3-d]pyridazin-5-one;
8-(4-methoxyphenyl)-pyrido[2,3-d]pyridazin-5-one;
8-(4-methylphenyl)-pyrido[2,3-d]pyridazin-5-one;
8-(3-bromophenyl)-pyrido[2,3-d]pyridazin-5-one;
8-(3-chlorophenyl)-pyrido[2,3-d]pyridazin-5-one;
8-(3-nitro-4-chlorophenyl)-pyrido[2,3-d]pyridazin-one;
8-(3-nitro-4-methylphenyl)-pyrido[2,3-d]pyridazin-one;
8-(3-methoxycarbonylphenyl)-pyrido[2,3-d]pyridazin-one;
8-(4-methoxycarbonylphenyl)-pyrido[2,3-d]pyridazin-one;
8-(3-methoxycarbonyl-4-methylphenyl)-pyrido[2,3-d]pyridazin-5-one;
8-(4-carboxyphenyl)-pyrido[2,3-d]pyridazin-5-one;
8-(4-carbamoylphenyl)-pyrido[2,3-d]pyridazin-5-one;
8-(4-N,N-dimethylcarbamoylphenyl)-pyrido[2,3-d]pyridazin-5-one; and
8-(3,4-methylenedioxyphenyl)-pyrido[2,3-d]-pyridazin-5-one;
there are obtained the following compounds:
6-(4-pyridylmethyl)-8-(3-methoxyphenyl)-pyrido-[2,3-d]pyridazin-5-one;
6-(4-pyridylmethyl)-8-(4-methoxyphenyl)-pyrido-[2,3-d]pyridazin-5-one;
6-(4-pyridylmethyl)-8-(4-methylphenyl)-pyrido-[2,3-d]pyridazin-5-one;

6-(4-pyridylmethyl)-8-(3-bromophenyl)-pyrido-[2,3-d]pyridazin-5-one;
6-(4-pyridylmethyl)-8-(3-chlorophenyl)-pyrido-[2,3-d]pyridazin-5-one;
6-(4-pyridylmethyl)-8-(3-nitro-4-chlorophenyl)-pyrido-[2,3-d]pyridazin-5-one;
6-(4-pyridylmethyl)-8-(3-nitro-4-methylphenyl)-pyrido-[2,3-d]pyridazin-5-one;
6-(4-pyridylmethyl)-8-(3-methoxycarbonylphenyl)-pyrido-[2,3-d]pyridazin-5-one;
6-(4-pyridylmethyl)-8-(4-methoxycarbonylphenyl)-pyrido-[2,3-d]pyridazin-5-one;
6-(4-pyridylmethyl)-8-(3-methoxycarbonyl-4-methylphenyl)-pyrido-[2,3-d]pyridazin-5-one;
6-(4-pyridylmethyl)-8-(4-carboxyphenyl)-pyrido-[2,3-d]pyridazin-5-one;
6-(4-pyridylmethyl)-8-(4-carbamoylphenyl)-pyrido-[2,3-d]pyridazin-5-one;
6-(4-pyridylmethyl)-8-(4-N,N-dimethylcarbamoylphenyl)-pyrido-[2,3-d]pyridazin-5-one; and
6-(4-pyridylmethyl)-8-(3,4-methylenedioxyphenyl)-pyrido-[2,3-d]pyridazin-5-one.

Example 10

Preparation of 7-(3-chlorophenyl)-furo[3,4-b]pyridin-5-one

10A. Formula 4, Where X is nitrogen, Y is carbon, $R^3$ is chloro and $R^2$, $R^4$, $R^5$ and $R^6$ are hydrogen A solution of 2,3-pyridinyldicarboxylic anhydride (20.0 g, 134 mmoles) in methanol (25 g, 617 mmoles) was refluxed for 10 minutes and the solvent removed. The solution was filtered and the remaining solvent was removed. The residue was added to 3-chlorobenzaldehyde (76 ml, 671 moles) and p-cymene (105 ml, 671 moles) and the mixture was stirred at 180° C. for 18 hours under an inert atmosphere. The solvent was removed and the residue was chromatographed yielding 7-(3-chlorophenyl)-furo[3,4-b]pyridin-5-one.

10B. Preparation of Other Compounds of Formula 4, Where X is nitrogen and Y is carbon By following the procedures of Example 10A and substituting 3-chlorobenzaldehyde with the following:
3-methoxybenzaldehyde;
4-methoxybenzaldehyde;
4-methylbenzaldehyde;
3-bromobenzaldehyde;
3-nitrobenzaldehyde;
3-nitro-4-chlorobenzaldehyde;
3-nitro-4-methylbenzaldehyde;
3-methoxycarbonylbenzaldehyde;
4-methoxycarbonylbenzaldehyde;
3-methoxycarbonyl-4-methyl-benzaldehyde;
4-carboxybenzaldehyde;
4-carbamoylbenzaldehyde;
4-N,N-dimethylcarbamoylbenzaldehyde; and
3,4-methylenedioxybenzaldehyde;
there are obtained the following respective compounds:
7-(3-methoxyphenyl)-furo[3,4-b]pyridin-5-one;
7-(4-methoxyphenyl)-furo[3,4-b]pyridin-5-one;
7-(4-methylphenyl)-furo[3,4-b]pyridin-5-one;
7-(3-bromophenyl)-furo[3,4-b]pyridin-5-one;
7-(3-nitrophenyl)-furo[3,4-b]pyridin-5-one;
7-(3-nitro-4-chlorophenyl)-furo[3,4-b]pyridin-5-one;
7-(3-nitro-4-methylphenyl)-furo[3,4-b]pyridin-5-one;
7-(3-methoxycarbonylphenyl)-furo[3,4-b]pyridin-5-one;
7-(4-methoxycarbonylphenyl)-furo[3,4-b]pyridin-5-one;
7-(3-methoxycarbonylphenyl-4-methyl)-furo[3,4-b]pyridin-5-one;
7-(4-carboxyphenyl)-furo[3,4-b]pyridin-5-one;
7-(4-carbamoylphenyl)-furo[3,4-b]pyridin-5-one;
7-(4-N,N-dimethylcarbamoylphenyl)-furo-[3,4-b]pyridin-5-one; and
7-(3,4-methylenedioxyphenyl)-furo[3,4-b]pyridin-5-one.

Example 11

Preparation of 2-(hydroxymethyl-3-chlorophenyl)-3-carboxypyridine

11A. Formula 5, Where X is nitrogen, Y is carbon, $R^3$ is chloro and $R^2$, $R^4$, $R^5$ and $R^6$ are hydrogen 7-(3-Chlorobenzoyl)-furo[3,4-b]pyridin-5-one (4.77 g, 19.4 mmoles) and 0.2N sodium hydroxide (21.4 mmoles) was dissolved in methanol and tetrahydrofuran (100 ml, 1:1). The mixture was heated to 75° C. and stirred for 3 hours and cooled. 1N Hydrochloric acid (20 ml) and water (200 ml) was added to the mixture. The resulting solution was extracted with ethyl acetate and dried over $Na_2SO_4$. The solution was filtered and the solvent removed yielding 4.94 g (96.8%) of 2-(hydroxymethyl-3-chlorophenyl)-3-carboxypyridine.

11B. Preparation of Other Compounds of Formula 5, Where X is nitrogen, Y is carbon By following the procedures of Example 11A and substituting for 7-(3-chlorophenyl)-furo[3,4-b]pyridin-5-one with the following:
7-(3-methoxyphenyl)-furo[3,4-b]pyridin-5-one;
7-(4-methoxyphenyl)-furo[3,4-b]pyridin-5-one;
7-(4-methylphenyl)-furo[3,4-b]pyridin-5-one;
7-(3-bromophenyl)-furo[3,4-b]pyridin-5-one;
7-(3-nitrophenyl)-furo[3,4-b]pyridin-5-one;
7-(3-nitro-4-chlorophenyl)-furo[3,4-b]pyridin-5-one;
7-(3-nitro-4-methylphenyl)-furo[3,4-b]pyridin-5-one;
7-(3-methoxycarbonylphenyl)-furo[3,4-b]pyridin-5-one;
7-(3-methoxycarbonyl-4-methylphenyl)-furo[3,4-b]-pyridin-5-one;
7-(4-carboxyphenyl)-furo[3,4-b]pyridin-5-one;
7-(4-carbamoylphenyl)-furo[3,4-b]pyridin-5-one;
7-(4-N,N-dimethylcarbamoylphenyl)-furo[3,4-b]-pyridin-5-one; and
7-(3,4-methylenedioxyphenyl)-furo[3,4-b]pyridin-5-one;
there are obtained the following compounds:
2-(hydroxymethyl-3-methoxyphenyl)-3-carboxypyridine;
2-(hydroxymethyl-4-methoxyphenyl)-3-carboxypyridine;
2-(hydroxymethyl-4-methylphenyl)-3-carboxypyridine;
2-(hydroxymethyl-3-bromophenyl)-3-carboxypyridine;
2-(hydroxymethyl-3-nitrophenyl)-3-carboxypyridine;
2-(hydroxymethyl-3-nitro-4-chlorophenyl)-3-carboxypyridine;
2-(hydroxymethyl-3-nitro-4-methylphenyl)-3-carboxypyridine;
2-(hydroxymethyl-3-carboxyphenyl)-3-carboxypyridine;
2-(hydroxymethyl-3-carboxy-4-methylphenyl)-3-carboxypyridine;
2-(hydroxymethyl-4-carboxyphenyl)-3-carboxypyridine;
2-(hydroxymethyl-4-carbamoylphenyl)-3-carboxypyridine;
2-(hydroxymethyl-4-N,N-dimethylcarbamoylphenyl)-3-carboxypyridine; and
2-(hydroxymethyl-3,4-methylenedioxyphenyl)-3-carboxypyridine.

Example 12

Preparation of 2-(3-chlorobenzoyl)-3-carboxypyridine

12A. Formula 6, Where X is nitrogen, Y is carbon, $R^3$ is chloro and $R^2$, $R^4$, $R^5$ and $R^6$ are hydrogen 2-(Hydroxymethyl-3-chlorophenyl)-3-carboxypyridine was dissolved in a solution of methylene chloride/glacial acetic acid (5:1). Pyridinium dichromate (10.95 g, 29 mmoles) was added and the solution was stirred at room temperature under an inert atmosphere. The solvent was removed yielding 2-(3-chlorobenzoyl)-3-carboxypyridine.

12B. Preparation of Other Compounds of Formula 6 Where X is nitrogen and Y is carbon By following the procedures of Example 12A and substituting for 2-(hydroxymethyl-3-chlorophenyl)-3-carboxypyridine with the following:

2-(hydroxymethyl-3-methoxyphenyl)-3-carboxypyridine;
2-(hydroxymethyl-4-methoxyphenyl)-3-carboxypyridine;
2-(hydroxymethyl-4-methylphenyl)-3-carboxypyridine;
2-(hydroxymethyl-3-bromophenyl)-3-carboxypyridine;
2-(hydroxymethyl-3-nitrophenyl)-3-carboxypyridine;
2-(hydroxymethyl-3-nitro-4-chlorophenyl)-3-carboxypyridine;
2-(hydroxymethyl-3-nitro-4-methylphenyl)-3-carboxypyridine;
2-(hydroxymethyl-3-methoxycarbonylphenyl)-3-carboxypyridine;
2-(hydroxymethyl-4-methoxycarbonylphenyl)-3-carboxypyridine;
2-(hydroxymethyl-3-methoxycarbonyl-4-methylphenyl)-3-carboxypyridine;
2-(hydroxymethyl-4-carboxyphenyl)-3-carboxypyridine;
2-(hydroxymethyl-4-carbamoylphenyl)-3-carboxypyridine;
2-(hydroxymethyl-4-N,N-dimethyl-carbamoylphenyl)-3-carboxypyridine; and
2-(hydroxymethyl-3,4-methylenedioxyphenyl)-3-carboxypyridine;

there are obtained the following compounds:

2-(3-methoxybenzoyl)-3-carboxypyridine;
2-(4-methoxybenzoyl)-3-carboxypyridine;
2-(4-methylbenzoyl)-3-carboxypyridine;
2-(3-bromobenzoyl)-3-carboxypyridine;
2-(3-nitrobenzoyl)-3-carboxypyridine;
2-(3-nitro-4-chlorobenzoyl)-3-carboxypyridine;
2-(3-nitro-4-methylbenzoyl)-3-carboxypyridine;
2-(3-methoxycarbonylbenzoyl)-3-carboxypyridine;
2-(4-methoxycarbonylbenzoyl)-3-carboxypyridine;
2-(3-methoxycarbonyl-4-methylbenzoyl)-3-carboxypyridine;
2-(4-carboxybenzoyl)-3-carboxypyridine;
2-(4-carbamoylbenzoyl)-3-carboxypyridine;
2-(4-N,N-dimethylcarbamoylbenzoyl)-3-carboxypyridine; and
2-(3,4-methylenedioxybenzoyl)-3-carboxypyridine.

Example 13

Preparation of 2-(3-chlorobenzoyl)-3-methoxycarbonylpyridine

13A. Formula II, Where X is nitrogen, Y is carbon, $R^3$ is chloro and $R^2$, $R^4$, $R^5$ and $R^6$ are hydrogen 2-(3-Chlorobenzoyl)-3-carboxypyridine was dissolved in a solution of 10% methanol and methylene chloride. Diazomethane was added and the solution was stirred for 1 hour at room temperature. The solution was extracted with methylene chloride followed by methylene chloride +1% methanol The desired product was combined from recrystallization (ethyl ether/hexane) and from the filtrate to yield 1.23 g of 2-(3-chlorobenzoyl)-3-methoxycarbonyl-pyridine.

13B. Preparation of Other Compounds of Formula II Where X is nitrogen and Y is carbon By following the procedures of Example 13A and substituting for 2-(3-chlorobenzoyl)-3-carboxypyridine with the following:

2-(3-methoxybenzoyl)-3-carboxypyridine;
2-(4-methoxybenzoyl)-3-carboxypyridine;
2-(4-methylbenzoyl)-3-carboxypyridine;
2-(3-bromobenzoyl)-3-carboxypyridine;
2-(3-nitrobenzoyl)-3-carboxypyridine;
2-(3-nitro-4-chlorobenzoyl)-3-carboxypyridine;
2-(3-nitro-4-methylbenzoyl)-3-carboxypyridine;
2-(3-methoxycarbonylbenzoyl)-3-carboxypyridine;
2-(4-methoxycarbonylbenzoyl)-3-carboxypyridine;
2-(3-methoxycarbonyl-4-methylbenzoyl)-3-carboxypyridine;
2-(4-carboxybenzoyl)-3-carboxypyridine;
2-(4-carbamoylbenzoyl)-3-carboxypyridine;
2-(4-N,N-dimethylcarbamoylbenzoyl)-3-carboxypyridine; and
2-(3,4-methylenedioxybenzoyl)-3-carboxypyridine;

there are obtained the following compounds:

2-(3-methoxybenzoyl)-3-methoxycarbonylpyridine;
2-(4-methoxybenzoyl)-3-methoxycarbonylpyridine;
2-(4-methylbenzoyl)-3-methoxycarbonylpyridine;
2-(3-bromobenzoyl)-3-methoxycarbonylpyridine;
2-(3-nitrobenzoyl)-3-methoxycarbonylpyridine;
2-(3-nitro-4-chlorobenzoyl)-3-methoxycarbonylpyridine;
2-(3-nitro-4-methylbenzoyl)-3-methoxycarbonylpyridine;
2-(3-methoxycarbonylbenzoyl)-3-methoxycarbonylpyridine;
2-(4-methoxycarbonylbenzoyl)-3-methoxycarbonylpyridine;
2-(3-methoxycarbonyl-4-methylbenzoyl)-3-methoxycarbonylpyridine;
2-(4-carboxybenzoyl)-3-methoxycarbonylpyridine;
2-(4-carbamoylbenzoyl)-3-methoxycarbonylpyridine;
2-(4-N,N-dimethylcarbamoylbenzoyl)-3-methoxycarbonylpyridine; and
2-(3,4-methylenedioxybenzoyl)-3-methoxycarbonylpyridine.

Example 14

Preparation of 8-(3-chlorophenyl)pyrido[2,3-d]pyridazin-5-one

14A. Formula I, Where X is nitrogen, Y is carbon, Z is oxygen, $R^1$ is hydrogen, $R^3$ is chloro and $R^2$, $R^4$, $R^5$ and $R^6$ are hydrogen A solution of 2-(3-chlorobenzoyl)-3-methoxycarbonylpyridine (0.55 g, 2.0 mmoles), hydrazine hydrate (0.15 ml, 3.0 mmoles) in ethanol (50 ml) was stirred at 100° C. for 18 hours under an inert atmosphere. The solution was cooled and solid in the solution was collected, washed with ethyl ether and dried to give 0.26 g of 8-(3-chlorophenyl)pyrido-[2,3-d]pyridazin-5-one (50.5%), mp 268°–269° C.

14B. Preparation of Other Compounds of Formula I Where X is nitrogen, Y is carbon, and Z is oxygen By following the procedures of Example 14A and substituting for 2-(3-chlorobenzoyl)-3-methoxycarbonylpyridine with the following:

2-(3-methoxybenzoyl)-3-methoxycarbonylpyridine;
2-(4-methoxybenzoyl)-3-methoxycarbonylpyridine;
2-(4-methylbenzoyl)-3-methoxycarbonylpyridine;
2-(3-bromobenzoyl)-3-methoxycarbonylpyridine;
2-(3-nitrobenzoyl)-3-methoxycarbonylpyridine;
2-(3-nitro-4-chlorobenzoyl)-3-methoxycarbonylpyridine;
2-(3-nitro-4-methylbenzoyl)-3-methoxycarbonylpyridine;

2-(3-methoxycarbonylbenzoyl)-3-methoxycarbonylpyridine;
2-(4-methoxycarbonylbenzoyl)-3-methoxycarbonylpyridine;
2-(3-methoxycarbonyl-4-methylbenzoyl)-3-methoxycarbonylpyridine;
2-(4-carboxybenzoyl)-3-methoxycarbonylpyridine;
2-(4-carbamoylbenzoyl)-3-methoxycarbonylpyridine;
2-(4-N,N-dimethylcarbamoylbenzoyl)-3-methoxycarbonylpyridine; and
2-(3,4-methylenedioxybenzoyl)-3-methoxycarbonylpyridine;
there are obtained the following compounds:
8-(3-methoxyphenyl)-pyrido[2,3-d]pyridazin-5-one;
8-(4-methoxyphenyl)-pyrido[2,3-d]pyridazin-5-one;
8-(4-methylphenyl)-pyrido[2,3-d]pyridazin-5-one;
8-(3-bromophenyl)-pyrido[2,3-d]pyridazin-5-one;
8-(3-nitrophenyl)-pyrido[2,3-d]pyridazin-5-one;
8-(3-nitro-4-chlorophenyl)-pyrido[2,3-d]pyridazin-5-one;
8-(3-nitro-4-methylphenyl)-pyrido[2,3-d]pyridazin-5-one;
8-(3-methoxycarbonylphenyl)-pyrido[2,3-d]pyridazin-5-one;
8-(4-methoxycarbonylphenyl)-pyrido[2,3-d]pyridazin-5-one;
8-(3-methoxycarbonyl-4-methylphenyl)-pyrido[2,3-d]pyridazin-5-one;
8-(4-carboxyphenyl)-pyrido[2,3-d]pyridazin-5-one;
8-(4-carbamoylphenyl)-pyrido[2,3-d]pyridazin-5-one;
8-(4-N,N-dimethylcarbamoylphenyl)-pyrido[2,3-d]-pyridazin-5-one; and
8-(3,4-methylenedioxyphenyl)-pyrido[2,3-d]pyridazin-5-one.

2-(4-carboxybenzoyl)-3-methoxycarbonylpyridine;
2-(4-carbamoylbenzoyl)-3-methoxycarbonylpyridine;
2-(4-N,N-dimethylcarbamoylbenzoyl)-3-methoxycarbonylpyridine; and
2-(3,4-methylenedioxybenzoyl)-3-methoxycarbonylpyridine;
there are obtained the following compounds:
6-phenyl-8-(3-methoxyphenyl)-pyrido[2,3-d]pyridazin-5-one;
6-phenyl-8-(4-methoxyphenyl)-pyrido[2,3-d]pyridazin-5-one;
6-phenyl-8-(4-methylphenyl)-pyrido[2,3-d]pyridazin-one;
6-phenyl-8-(3-bromophenyl)-pyrido[2,3-d]pyridazin-one;
6-phenyl-8-(3-nitrophenyl)-pyrido[2,3-d]pyridazin-one;
6-phenyl-8-(3-nitro-4-chlorophenyl)-pyrido-[2,3-d]pyridazin-5-one;
6-phenyl-8-(3-nitro-4-methylphenyl)-pyrido-[2,3-d]pyridazin-5-one;
6-phenyl-8-(3-methoxycarbonylphenyl)-pyrido-[2,3-d]pyridazin-5-one;
6-phenyl-8-(4-methoxycarbonylphenyl)-pyrido-[2,3-d]pyridazin-5-one;
6-phenyl-8-(3-methoxycarbonyl-4-methylphenyl)-pyrido-[2,3-d]pyridazin-5-one;
6-phenyl-8-(4-carboxyphenyl)-pyrido[2,3-d]pyridazin-5-one;
6-phenyl-8-(4-carbamoylphenyl)-pyrido-[2,3-d]pyridazin-5-one;
6-phenyl-8-(4-N,N-dimethylcarbamoylphenyl)-pyrido[2,3-d]pyridazin-5-one; and
6-phenyl-8-(3,4-methylenedioxyphenyl)-pyrido[2,3-d]pyridazin-5-one.

Example 15

Preparation of 6-phenyl-8-(3-chlorophenyl)pyrido[2,3-d]pyridazin-5-one

15A. Formula I, Where X is nitrogen, Y is carbon, Z is oxygen, $R^1$ is phenyl, $R^3$ is chloro and $R^2$, $R^4$, $R^5$ and $R^6$ are hydrogen A solution of 2-(3-chlorobenzoyl)-3-methoxycarbonylpyridine (0.30 g, 1.09 mmoles), phenylhydrazine (0.27 ml, 2.72 mmoles) in ethanol (18 ml) was stirred at 100° C. for 72 hours. The solution was cooled and the solvent was removed. The residue was triturated with methanol to give a white solid, which was collected and air dried, yielding 0.26 g of 6-phenyl-8-(3-chlorophenyl)pyrido[2,3-d]pyridazin-5-one (71.5%), mp 144°–145° C.

15B. Preparation of Other Compounds of Formula I Where X nitrogen, Y is carbon, and Z is oxygen By following the procedures of Example 15A and substituting for 2-(3-chlorobenzoyl)-3-methoxycarbonylpyridine with the following:
2-(3-methoxybenzoyl)-3-methoxycarbonylpyridine;
(4-methoxybenzoyl)-3-methoxycarbonylpyridine;
(4-methylbenzoyl)-3-methoxycarbonylpyridine;
2-(3-bromobenzoyl)-3-methoxycarbonylpyridine;
2-(3-nitrobenzoyl)-3-methoxycarbonylpyridine;
2-(3-nitro-4-chlorobenzoyl)-3-methoxycarbonylpyridine;
2-(3-nitro-4-methylbenzoyl)-3-methoxycarbonylpyridine;
2-(3-methoxycarbonylbenzoyl)-3-methoxycarbonylpyridine;
2-(4-methoxycarbonylbenzoyl)-3-methoxycarbonylpyridine;
2-(3-methoxycarbonyl-4-methylbenzoyl)-3-methoxycarbonylpyridine;

Example 16

Preparation of 6-benzyl-8-(3-nitrophenyl)pyrido[2,3-d]pyridazin-5-one

16A. Formula I, Where X is nitrogen, Y is carbon, Z is oxygen, $R^1$ is benzyl, $R^3$ is chloro and $R^2$, $R^4$, $R^5$ and $R^6$ are hydrogen A solution of 2-(3-chlorobenzoyl)-3-methoxycarbonylpyridine (0.30 g, 1.09 mmoles), benzylhydrazine hydrochloride (0.53 ml, 2.72 mmoles) in ethanol (18 ml) was refluxed for 132 hours (5 days). The solution was cooled and the solvent was removed. The residue was dissolved in ethanol (minimal amount used) and stored in a freezer to induce crystallization. The solid material was collected from the solution, chromatographed, eluted with 100% methylene chloride, and crystallized from methanol to yield 0.21 g of 6-benzyl-8-(3-nitrophenyl)pyrido[2,3-d]pyridazin-5-one (55.4%), mp 141° C.

16B. Preparation of Other Compounds of Formula I Where X is nitrogen, Y is carbon, and Z is oxygen By following the procedures of Example 16A and substituting for 2-(3-chlorobenzoyl)-3-methoxycarbonylpyridine with the following:
2-(3-methoxybenzoyl)-3-methoxycarbonylpyridine;
2-(4-methoxybenzoyl)-3-methoxycarbonylpyridine;
2-(4-methylbenzoyl)-3-methoxycarbonylpyridine;
2-(3-bromobenzoyl)-3-methoxycarbonylpyridine;
2-(3-nitrobenzoyl)-3-methoxycarbonylpyridine;
2-(3-nitro-4-chlorobenzoyl)-3-methoxycarbonylpyridine;
2-(3-nitro-4-methylbenzoyl)-3-methoxy-carbonylpyridine;
2-(3-methoxycarbonylbenzoyl)-3-methoxycarbonylpyridine;

2-(4-methoxycarbonylbenzoyl)-3-methoxy-
carbonylpyridine;
2-(3-methoxycarbonyl-4-methylbenzoyl)-3-methoxy-
carbonylpyridine;
2-(4-carboxybenzoyl)-3-methoxycarbonylpyridine;
2-(4-carbamoylbenzoyl)-3-methoxycarbonylpyridine;
2-(4-N,N-dimethylcarbamoylbenzoyl)-3-methoxy-
carbonylpyridine; and
2-(3,4-methylenedioxybenzoyl)-3-methoxy-
carbonylpyridine;
there are obtained the following compounds:
6-benzyl-8-(3-methoxyphenyl)-pyrido[2,3-d]pyridazin-5-one;
6-benzyl-8-(4-methoxyphenyl)-pyrido[2,3-d]pyridazin-5-one;
6-benzyl-8-(4-methylphenyl)-pyrido[2,3-d]pyridazin-5-one;
6-benzyl-8-(3-bromophenyl)-pyrido[2,3-d]pyridazin-5-one;
6-benzyl-8-(3-nitrophenyl)-pyrido[2,3-d]pyridazin-5-one;
6-benzyl-8-(3-nitro-4-chlorophenyl)-pyrido-[2,3-d]pyridazin-5-one;
6-benzyl-8-(3-nitro-4-methylphenyl)-pyrido-[2,3-d]pyridazin-5-one;
6-benzyl-8-(3-methoxycarbonylphenyl)-pyrido-[2,3-d]pyridazin-5-one;
6-benzyl-8-(4-methoxycarbonylphenyl)-pyrido-[2,3-d]pyridazin-5-one;
6-benzyl-8-(3-methoxycarbonyl-4-methylphenyl)-pyrido[2,3-d]pyridazin-5-one;
6-benzyl-8-(4-carboxyphenyl)-pyrido[2,3-d]pyridazin-5-one;
6-benzyl-8-(4-carbamoylphenyl)-pyrido-[2,3-d]-pyridazin-5-one;
6-benzyl-8-(4-N,N-dimethylcarbamoylphenyl)-pyrido[2,3-d]pyridazin-5-one; and
6-benzyl-8-(3,4-methylenedioxyphenyl)-pyrido[2,3-d]pyridazin-5-one.

Example 17

Preparation of 6-ethyl-8-(3-chlorophenyl)pyrido[2,3-d]pyridazin-5-one

17A. Formula I, Where X is nitrogen, Y is carbon, Z is oxygen, $R^1$ is ethyl, $R^3$ is chloro and $R^2$, $R^4$, $R^5$ and $R^6$ are hydrogen.

To a suspension of 8-(3-chlorophenyl)pyrido[2,3-d]pyridazin-5-one (0.32 g, 1.24 mmoles) in tetrahydrofuran (50 ml) was added sodium hydride (0.06 g, 1.4 mmoles). The mixture was stirred for 1 hour at room temperature. Iodoethane (0.48 g, 3.1 mmoles) was added and the solution was refluxed for 18 hours under an inert atmosphere. The mixture was cooled and acidified by the addition of 50 ml of 1N HCl. The desired compound was isolated by extraction with ethyl acetate (extracted until no product detected in aqueous layer), washed with sodium bicarbonate, brine and dried over magnesium sulfate. The solution was filtered and the solvent removed yielding 0.85 g of the crude desired product. The product was purified by recrystallization from methanol to yield 0.24 g of 6-ethyl-8-(3-chlorophenyl) pyrido-[2,3-d]pyridazin-5-one (67.8%), mp. 117°–118° C.

17B. Preparation of Other Compounds of Formula I Where X is nitrogen, Y is carbon, and Z is oxygen.

By following the procedures of Example 17A and substituting for 8- (3-chlorophenyl)-pyrido[2,3- d]pyridazin-5-one with the following:
8-(3-methoxyphenyl)-pyrido[2,3-d]pyridazin-5-one;
8-(4-methoxyphenyl)-pyrido[2,3- d]pyridazin-5-one;
8-(4-methylphenyl)-pyrido[2,3 -d]pyridazin-5-one;
8-(3-bromophenyl)-pyrido[2,3 - d]pyridazin-5-one;
8-(3-nitrophenyl)- pyrido[2,3- d]pyridazin-5-one;
8-(3-nitro-4-chlorophenyl)-pyrido[2,3-d]pyridazin-5-one;
8-(3 -nitro-4-methylphenyl)-pyrido[2,3-d]pyridazin-5-one;
8-(3-methoxycarbonylphenyl)-pyrido [2,3-d]pyridazin-5-one;
8-(4-methoxycarbonylphenyl)-pyrido [2,3-d]pyridazin-5-one;
8-(3-methoxycarbonyl-4-methylphenyl)-pyrido[2,3-d]-pyridazin-5-one;
8-(4-carboxyphenyl)-pyrido[2,3 -d]pyridazin-5-one;
8-(4-carbamoylphenyl)-pyrido[2,3-d]pyridazin-5-one;
8-(4-N,N-dimethylcarbamoylphenyl)-pyrido[2,3-d]-pyridazin-5-one; and
8-(3,4-methylenedioxyphenyl)-pyrido[2,3 -d]-pyridazin-5-one;
there are obtained the following compounds:
6-ethyl-8-(3-methoxyphenyl)-pyrido[2,3-d]pyridazin-5-one;
6-ethyl-8-(4-methoxyphenyl)-pyrido[2,3-d]pyridazin-5-one;
6-ethyl-8-(4-methylphenyl)-pyrido[2,3-d]pyridazin-5-one;
6-ethyl-8-(3-bromophenyl)-pyrido[2,3-d]pyridazin- 5-one;
6-ethyl-8-(3-nitrophenyl)-pyrido[2,3 -d]pyridazin-5-one;
6-ethyl-8-(3-nitro-4-chlorophenyl)-pyrido-[2,3-d]pyridazin-5-one;
6-ethyl-8-(3-nitro-4-methylphenyl)-pyrido-[2,3-d]pyridazin-5-one;
6-ethyl-8-(3-methoxycarbonylphenyl)-pyrido-[2,3-d]pyridazin-5-one;
6-ethyl-8-(4-methoxycarbonylphenyl)-pyrido-[2,3-d]pyridazin-5-one;
6-ethyl-8-(3-methoxycarbonyl-4-methylphenyl)-pyrido[2,3-d]pyridazin-5-one;
6-ethyl-8-(4-carboxyphenyl)-pyrido[2,3-d]pyridazin-one;
6-ethyl-8-(4-carbamoylphenyl)-pyrido[2,3-d]pyridazin-5-one;
6-ethyl-8-(4-N,N-dimethylcarbamoylphenyl)-pyrido-[2,3-d]pyridazin-5-one; and
6-ethyl-8-(3,4-methylenedioxyphenyl)-pyrido-[2,3-d]pyridazin-5-one.

Example 18

Preparation of 6-(2-propyl)-8-(3-chlorophenyl) pyrido [2,3-d]pyridazin -5-one

18A. Formula i, Where X is nitrogen, Y is carbon, Z is oxygen, $R^1$ is 2-propyl, $R^3$ is chloro and $R^2$, $R^4$, $R^5$ and $R^6$ are hydrogen.

To a suspension of 8- (3-chlorophenyl)pyrido [2,3 -d]pyridazin-5-one (0.33 g, 1.28 mmoles) in tetrahydrofuran (50 ml) was added sodium hydride (0.07 g, 1.53 mmoles). The mixture was stirred at room temperature for 30 minutes under an inert atmosphere. 2-Iodopropane (0.64 ml, 6.4 mmoles) was added and the mixture refluxed for 48 hours. The mixture was cooled and acidified by the addition of 50 ml of 1N HCl. The mixture was extracted with ethyl acetate (3×50 ml) and dried over magnesium sulfate. The solution was filtered and the solvent removed to yield the crude product. The product was purified by crystallization (ethyl ether/hexane) yielding 0.15 g of 6-(2-propyl)-8-(3-chlorophenyl)pyrido[2,3-d]pyridazin-5-one (39%), mp 80°–81° C.

18B. Preparation of Other Compounds of Formula I Where X is nitrogen, Y is carbon, and Z is oxygen.

By following the procedures of Example 18A and substituting for 8-(3-chlorophenyl) -pyrido[2,3 -d]pyridazin-5 -one with the following:

8-(3-methoxyphenyl)-pyrido[2,3-d]pyridazin-5-one;
8-(4-methoxyphenyl)-pyrido[2,3-d]pyridazin-5-one;
8-(4-methylphenyl)-pyrido[2,3-d]pyridazin-5-one;
8-(3-bromophenyl)-pyrido[2,3-d]pyridazin-5-one;
8-(3-nitrophenyl)-pyrido[2,3-d]pyridazin-5-one;
8-(3-nitro-4-chlorophenyl)-pyrido[2,3-d]pyridazino-5-one;
8-(3-nitro-4-methylphenyl)-pyrido[2,3-d]pyridazin-5-one;
8-(3-methoxycarbonylphenyl)-pyrido[2,3-d]pyridazin-5-one;
8-(4-methoxycarbonylphenyl)-pyrido[2,3-d]pyridazin-5-one;
8-(3-methoxycarbonyl-4-methylphenyl)-pyrido[2,3-d]pyridazin-5-one;
8-(4-carboxyphenyl)-pyrido[2,3-d]pyridazin-5-one;
8-(4-carbamoylphenyl)-pyrido[2,3-d]pyridazin-5-one;
8-(4-N,N-dimethylcarbamoylphenyl)-pyrido[2,3-d]pyridazin-5-one; and
8-(3,4-methylenedioxyphenyl)-pyrido[2,3-d]pyridazin-5-one;

there are obtained the following compounds:

6-(2-propyl)-8-(3-methoxyphenyl)-pyrido-[2,3-d]pyridazin-5-one;
6-(2-propyl)-8-(4-methoxyphenyl)-pyrido-[2,3-d]pyridazin-5-one;
6-(2-propyl)-8-(4-methylphenyl)-pyrido-[2,3-d]-pyridazin-5-one;
6-(2-propyl)-8-(3-bromophenyl)-pyrido-[2,3-d]-pyridazin-5-one;
6-(2-propyl)-8-(3-nitrophenyl)-pyrido-[2,3-d]-pyridazin-5-one;
6-(2-propyl)-8-(3-nitro-4-chlorophenyl)-pyrido-[2,3-d]pyridazin-5-one;
6-(2-propyl)-8-(3-nitro-4-methylphenyl)-pyrido-[2,3-d]pyridazin-5-one;
6-(2-propyl)-8-(3-methoxycarbonylphenyl)-pyrido-[2,3-d]pyridazin-5-one;
6-(2-propyl)-8-(4-methoxycarbonylphenyl)-pyrido-[2,3-d]pyridazin-5-one;
6-(2-propyl)-8-(3-methoxycarbonyl-4-methylphenyl)-pyrido-[2,3-d]pyridazin-5-one;
6-(2-propyl)-8-(4-carboxyphenyl)-pyrido-[2,3-d]pyridazin-5-one;
6-(2-propyl)-8-(4-carbamoylphenyl)-pyrido-[2,3-d]pyridazin-5-one;
6-(2-propyl)-8-(4-N,N-dimethylcarbamoylphenyl)-pyrido[2,3-d]pyridazin-5-one; and
6-(2-propyl)-8-(3,4-methylenedioxyphenyl)-pyrido-[2,3-d]pyridazin-5-one.

Example 19

Preparation of 6-(4-pyridylmethyl)-8-(3-chlorophenyl)pyrido[2,3-d]pyridazin-5-one 19A. Formula I, Where X is nitrogen, Y is carbon, Z is oxygen, $R^1$ is 4-pyridylmethyl, $R^3$ is chloro and $R^2$, $R^4$, $R^5$ and $R^6$ are hydrogen.

To a suspension of 8-(3-chlorophenyl)pyrido[2,3-d]pyridazin-5-one (0.50 g, 1.90 mmoles) in dimethylformamide (50 ml) was added potassium carbonate (3.22 g, 23.3 mmoles). The mixture was stirred at room temperature for 1 hour under an inert atmosphere. 4-Picolyl chloride (1.59 g, 9.7 mmoles) and potassium iodide (1.61 g, 9.7 mmoles) was added, the mixture was stirred at 80° C. for 168 hours (7 days). The mixture was cooled, the insoluble material was filtered out and the solvent removed yielding 2.13 g of the crude product. The product was purified by chromatography, eluted with 100% ethylacetate and crystallized from methanol yielding 0.091 g of 6-(4-pyridylmethyl)-8-(3-chlorophenyl)pyrido[2,3-d]pyridazin-5-one (13.7%), mp 152° C.

19B. Preparation of Other Compounds of Formula I Where X is nitrogen, Y is carbon, and Z is oxygen.

By following the procedures of Example 19A and substituting for 8-(3-chlorophenyl)-pyrido[2,3-d]pyridazin-5-one with the following:

8-(3-methoxyphenyl)-pyrido[2,3-d]pyridazin-5-one;
8-(4-methoxyphenyl)-pyrido[2,3-d]pyridazin-5-one;
8-(4-methylphenyl)- pyrido[2,3-d]pyridazin-5-one;
8-(3-bromophenyl)- pyrido[2,3-d]pyridazin-5-one;
8-(3-nitrophenyl)-pyrido[2,3-d]pyridazin-5-one;
8-(3-nitro-4-chlorophenyl)-pyrido[2,3-d]pyridazin-5-one;
8-(3-nitro-4-methylphenyl)-pyrido[2,3-d]pyridazin-5-one;
8-(3-methoxycarbonylphenyl)-pyrido[2,3-d]pyridazin-5-one;
8-(4-methoxycarbonylphenyl)-pyrido[2,3-d]pyridazin-5-one;
8-(3-methoxycarbonyl-4-methylphenyl)-pyrido[2,3-d]pyridazin-5-one;
8-(4-carboxyphenyl)- pyrido[2,3-d]pyridazin-5-one;
8-(4-carbamoylphenyl)-pyrido[2,3-d]pyridazin-5-one;
8-(4-N,N-dimethylcarbamoylphenyl)-pyrido[2,3-d]pyridazin-5-one; and
8-(3,4-methylenedioxyphenyl)-pyrido[2,3-d]pyridazin-5-one;

there are obtained the following compounds:

6-(4-pyridylmethyl)-8-(3-methoxyphenyl)-pyrido-[2,3-d]pyridazin-5-one;
6-(4-pyridylmethyl)-8-(4-methoxyphenyl)-pyrido-[2,3-d]pyridazin-5-one;
6-(4-pyridylmethyl)-8-(4-methylphenyl)-pyrido-[2,3-d]pyridazin-5-one;
6-(4-pyridylmethyl)-8-(3-bromophenyl)-pyrido-[2,3-d]pyridazin-5-one;
6-(4-pyridylmethyl)-8-(3-nitrophenyl)-pyrido-[2,3-d]pyridazin-5-one;
6-(4-pyridylmethyl)-8-(3-nitro-4-chlorophenyl)-pyrido-[2,3-d]pyridazin-5-one;
6-(4-pyridylmethyl)-8-(3-nitro-4-methylphenyl)-pyrido-[2,3-d]pyridazin-5-one;
6-(4-pyridylmethyl)-8-(3-methoxycarbonylphenyl)-pyrido-[2,3-d]pyridazin-5-one;
6-(4-pyridylmethyl)-8-(4-methoxycarbonylphenyl)-pyrido-[2,3-d]pyridazin-5-one;
6-(4-pyridylmethyl)-8-(3-methoxycarbonyl-4-methylphenyl)-pyrido-[2,3-d]pyridazin-5-one;
6-(4-pyridylmethyl)-8-(4-carboxyphenyl)-pyrido-[2,3-d]pyridazin-5-one;
6-(4-pyridylmethyl)-8-(4-carbamoylphenyl)-pyrido-[2,3-d]pyridazin-5-one;
6-(4-pyridylmethyl)-8-(4-N,N-dimethylcarbamoylphenyl)-pyrido-[2,3-d]pyridazin-5-one; and
6-(4-pyridylmethyl)-8-(3,4-methylenedioxyphenyl)-pyrido-[2,3-d]pyridazin-5-one.

Example 20

Preparation of 2-(3-chlorobenzoyl)-3-carboxypyridine and 2-carboxy-3-(3-chlorobenzoyl)pyridine Using A Grignard Reagent 20A. Formula 6, Where X is nitrogen, Y is carbon, $R^3$ is chloro and $R^2$, $R^4$, $R^5$ and $R^6$ are hydrogen.

A Grignard reagent was prepared by adding 1-bromo-3-chlorobenzene (11.75 ml, 100 mmoles) to a suspension of magnesium (2.43 g, 100 mmoles) in tetrahydrofuran (100 ml) and stirred at room temperature for 18 hours under an inert atmosphere. The Grignard reagent was added in a dropwise manner to a solution of 2,3-pyridyldicarboxylic anhydride (14.91ml, 100mmoles) in tetrahydrofuran (200 ml) at a temperature of −78° C. over a 2 hour period. After the addition the solution was stirred for an additional 45 minutes. 1N HCl (110 ml) was added and the solution was stirred for 1 hour. The desired product was extracted with ethyl acetate, washed in brine and dried over $Na_2SO_4$ yielding 2-(3-chlorobenzoyl)-3-carboxypyridine and 2-carboxy-3-(3-chlorobenzoyl)pyridine.

2-(3-Chlorobenzoyl)-3-carboxypyridine (Formula 6, where X is nitrogen, Y is carbon, $R^3$ is chloro and $R^2$, $R^4$, $R^5$ and $R^6$ are hydrogen) can be converted to the corresponding compounds of Formulae II and I by following the procedures of Examples 13–19, respectively.

20B. Preparation of Other Compounds of Formula II Where X is nitrogen and Y is carbon.

By following the procedures of Example 20A and substituting for 1-bromo-3-chlorobenzene with the following:
1-bromo-3-thiomethylbenzene;
1-bromo-3-methylbenzene;
1-bromo-3-trifluoromethylbenzene;
1-bromo-3,4-methylenedioxybenzene;
1-chloro-3-thiomethylbenzene;
1-chloro-3-methylbenzene;
1-chloro-3-trifluoromethylbenzene;
1-chloro-3,4-methylenedioxybenzene;
1-chloro-3-methoxybenzene;
1-chlorobenzene; and
1-bromobenzene;
there are obtained the following respective compounds:
2-(3-thiomethylbenzoyl)-3-carboxypyridine and 2-carboxy-3-(3-thiomethylbenzoyl)pyridine;
2-(3-methylbenzoyl)-3-carboxypyridine and 2-carboxy-3-(3-methylbenzoyl)pyridine;
2-(3- trifluoromethylbenzoyl )-3-carboxypyridine and 2-carboxy-3-(3-trifluoromethylbenzoyl)pyridine;
2-(3,4 -methylenedioxybenzoyl)-3-carboxypyridine and 2-carboxy-3-(3,4-methylenedioxybenzoyl)pyridine;
2-(3-thiomethylbenzoyl)-3-carboxypyridine and 2-carboxy-3-(3-thiomethylbenzoyl)pyridine;
2-(3-methylbenzoyl)-3-carboxypyridine and 2-carboxy-3-(3-methylbenzoyl)pyridine;
2-(3- trifluoromethylbenzoyl)-3-carboxypyridine and 2-carboxy-3-(3- trifluoromethylbenzoyl)pyridine;
2-(3,4 -methylenedioxybenzoyl)-3-carboxypyridine and 2-carboxy-3-(3,4-methylenedioxybenzoyl)pyridine;
2-(3-methoxybenzoyl)-3-carboxypyridine and 2-carboxy-3-(3-methoxybenzoyl)pyridine;
2-benzoyl-3-carboxypyridine and 2-carboxy-3-benzoylpyridine; and
2-benzoyl-3-carboxypyridine and 2-carboxy-3-benzoylpyridine.

Example 21

Preparation of 2-methoxycarbonyl-3-(3-chlorobenzoyl)pyridine

21A. Formula II, Where X is carbon and Y is nitrogen, $R^3$ is chloro, and $R^2$, $R^4$, $R^5$ and $R^6$ are hydrogen.

Following the procedures of Example 13A and substituting for 2-(3-chlorobenzoyl)-3-carboxypyridine with 2-carboxy-3-(3-chlorobenzoyl)pyridine there is obtained 2-methoxy-carbonyl-3-(3-chlorobenzoyl)pyridine.

21B. Formula II, Where X is carbon and Y is nitrogen.

By following the procedures of Example 21A and substituting for 2-carboxy-3-(3-chlorobenzoyl)pyridine with the following:

2-carboxy-3-(3-methoxybenzoyl)pyridine;
2-carboxy-3-(4-methoxybenzoyl)pyridine;
2-carboxy-3-(4-methylbenzoyl)pyridine;
2-carboxy-3-(3-bromobenzoyl)pyridine;
2-carboxy-3-(3-methoxycarbonylbenzoyl)pyridine;
2-carboxy-3-(4-methoxycarbonylbenzoyl)pyridine;
2-carboxy-3-(3-methoxycarbonyl-4-methylbenzoyl) pyridine;
2-carboxy-3-(4-carboxybenzoyl)pyridine;
2-carboxy-3-(4-carbamoylbenzoyl)pyridine;
2-carboxy-3o(4-N,N-dimethylcarbamoylbenzoyl)pyridine; and
2-carboxy-3-(3,4-methylenedioxybenzoyl)pyridine;
there are obtained the following compounds:
2-methoxycarbonyl-3-(3-methoxybenzoyl)pyridine;
2-methoxycarbonyl-3-(4-methoxybenzoyl)pyridine;
2-methoxycarbonyl-3-(4-methylbenzoyl)pyridine;
2-methoxycarbonyl-3-(3-bromobenzoyl)pyridine;
2-methoxycarbonyl-3-(3-methoxycarbonylbenzoyl) pyridine;
2-methoxycarbonyl-3-(4-methoxycarbonylbenzoyl) pyridine;
2-methoxycarbonyl-3-(3-methoxycarbonyl-4-methylbenzoyl)pyridine;
2-methoxycarbonyl-3-(4-carboxybenzoyl)pyridine;
2-methoxycarbonyl-3-(4-carbamoylbenzoyl)pyridine;
2-methoxycarbonyl-3-(4-N,N-dimethylcarbamoylbenzoyl) pyridine; and
2-methoxycarbonyl-3-(3,4-methylenedioxybenzoyl) pyridine.

Example 22

Preparation of 5-(3-chlorophenyl)-pyrido[2,3-d] pyridazin-8-one

22A. Formula I, Where X is carbon, Y is nitrogen, Z is oxygen, $R^3$ is chloro and $R^1$, $R^2$, $R^4$, $R^5$ and $R^6$ are hydrogen.

Following the procedures of Example 14A and substituting for 2-(3-chlorobenzoyl)-3-methoxycarbonylpyridine with 2-methoxycarbonyl-3-(3-chlorobenzoyl)pyridine there is obtained 5-(3-chlorophenyl)-pyrido[2,3-d]pyridazin-8-one.

22B. Preparation of Other Compounds of Formula II Where X is carbon, Y is nitrogen, Z is oxygen.

By following the procedures of EXample 22A and substituting for 2-methoxycarbonyl-3-(3-chlorobenzoyl) pyridine with the following:
2-methoxycarbonyl-3-(3-methoxybenzoyl)pyridine;
2-methoxycarbonyl-3-(4-methoxybenzoyl)pyridine;
2-methoxycarbonyl-3-(4-methylbenzoyl)pyridine;
2-methoxycarbonyl-3-(3-bromobenzoyl)pyridine;
2-methoxycarbonyl-3-(3-methoxycarbonylbenzoyl) pyridine;
2-methoxycarbonyl-3-(4-methoxycarbonylbenzoyl) pyridine;
2-methoxycarbonyl-3-(3-methoxycarbonyl-4-methylbenzoyl)pyridine;
2-methoxycarbonyl-3-(4-carboxybenzoyl)pyridine;
2-methoxycarbonyl-3-(4-carbamoylbenzoyl)pyridine;
2-methoxycarbonyl-3-(4-N,N-dimethylcarbamoylbenzoyl) pyridine; and
2-methoxycarbonyl-3-(3,4-methylenedioxybenzoyl) pyridine;
there are obtained the following compounds:
5 -(3-methoxyphenyl)-pyrido[2,3-d]pyridazin-8-one;
5-(4-methoxyphenyl)-pyrido[2,3-d]pyridazin-8-one;

5-(4-methylphenyl)-pyrido[2,3-d]pyridazin-8-one;
5-(3-bromophenyl)-pyrido[2,3-d]pyridazin-8-one;
5-(3-methoxycarbonylphenyl)-pyrido[2,3-d]pyridazin-one;
5-(4-methoxycarbonylphenyl)-pyrido[2,3-d]pyridazin-one;
5-(3-methoxycarbonyl-4-methylphenyl)-pyrido[2,3-d]-pyridazin-8-one;
5-(4- carboxyphenyl)- pyrido[2,3-d]pyridazin -8-one;
5-(4 - carbamoylphenyl)-pyrido[2,3-d]pyridazin-8-one;
5-(4-N,N-dimethylcarbamoylphenyl)-pyrido[2,3-d]-pyridazin-8-one; and
5-(3,4-methylenedioxyphenyl)-pyrido[2,3-d]-pyridazin-8-one.

Example 23

Preparation of 5-(3-chlorophenyl)-7-phenylpyrido[2,3-d]pyridazin-8-one

23A. Formula I, Where X is carbon, Y is nitrogen, Z is oxygen, $R^1$ is phenyl, $R^3$ is chloro and $R^2$, $R^4$, $R^5$ and $R^6$ are hydrogen.

Following the procedures of Example 15A and substituting for 2-(3-chlorobenzoyl)-3-methoxycarbonylpyridine with 2-methoxycarbonyl-3-(3-chlorobenzoyl)pyridine there is obtained 5-(3-chlorophenyl)-7-phenylpyrido[2,3-d]pyridazin-8-one.

23B. Preparation of Other Compounds of Formula I, Where X is carbon, Y is nitrogen, and Z is oxygen.

By following the procedures of Example 23A and substituting for 2-methoxycarbonyl-3-(3-chlorobenzoyl)pyridine with the following:
2-methoxycarbonyl-3-(3-methoxybenzoyl)pyridine;
2-methoxycarbonyl-3-(4-methoxybenzoyl)pyridine;
2-methoxycarbonyl-3-(4-methylbenzoyl)pyridine;
2-methoxycarbonyl-3-(3-bromobenzoyl)pyridine;
2-methoxycarbonyl-3-(3-methoxycarbonylbenzoyl) pyridine;
2-methoxycarbonyl-3-(4-methoxycarbonylbenzoyl) pyridine;
2-methoxycarbonyl-3-(3-methoxycarbonyl-4-methylbenzoyl)pyridine;
2-methoxycarbonyl-3-(4-carboxybenzoyl)pyridine;
2-methoxycarbonyl-3-(4-carbamoylbenzoyl)pyridine;
2-methoxycarbonyl-3-(4- N,N-dimethylcarbamoylbenzoyl) pyridine; and
2-methoxycarbonyl -3-(3,4-methyl enedioxybenzoyl) pyridine;

there are obtained the following compounds:
5-(3-methoxyphenyl)-7-phenylpyrido[2,3-d]pyridazin-one;
5-(4-methoxyphenyl)-7-phenylpyrido[2,3-d]pyridazin-one;
5-(4-methylphenyl)-7-phenylpyrido[2,3-d]pyridazin-one;
5-(3-bromophenyl)-7-phenylpyrido[2,3-d]pyridazin-8-one;
5-(3-methoxycarbonylphenyl)-7-phenylpyrido[2,3-d]-pyridazin-8-one;
5-(4-methoxycarbonylphenyl)-7-phenylpyrido[2,3-d]-pyridazin-8-one;
5-(3-methoxycarbonyl-4-methylphenyl)-7-phenylpyrido[2,3-d]pyridazin-8-one;
5-(4-carboxyphenyl)-7-phenylpyrido[2,3-d]pyridazin-one;
5-(4-carbamoylphenyl)-7-phenylpyrido[2,3-d]-pyridazin-8-one;
5-(4-N,N-dimethylcarbamoylphenyl)-7-phenylpyrido-[2,3-d]pyridazin-8-one; and
5-(3,4-methylenedioxyphenyl)-7-phenylpyrido[2,3-d]-pyridazin-8-one.

Example 24

Preparation of 5-(3-chlorophenyl)-7-benzylpyrido[2,3-d]pyridazin-8-one

24A. Formula I, Where X is carbon, Y is nitrogen, Z is oxygen, $R^1$ is benzyl, $R^3$ is chloro and $R^2$, $R^4$, $R^5$ and $R^6$ are hydrogen.

Following the procedures of Example 16A and substituting for 2-(3-chlorobenzoyl)-3-methoxycarbonylpyridine with 2-methoxycarbonyl-3-(3-chlorobenzoyl)pyridine there is obtained 5-(3-chlorophenyl)-7-benzylpyrido[2,3-d] pyridazin-8-one.

24B. Preparation of Other Compounds of Formula I, Where X is carbon, Y is nitrogen, and Z is oxygen.

By following the procedures of Example 24A and substituting for 2-methoxycarbonyl-3-(3-chlorobenzoyl)-pyridine with the following:
2-methoxycarbonyl-3-(3-methoxybenzoyl)pyridine;
2-methoxycarbonyl-3-(4-methoxybenzoyl)pyridine;
2-methoxycarbonyl-3-(4-methylbenzoyl)pyridine;
2-methoxycarbonyl-3-(3-bromobenzoyl)pyridine;
2-methoxycarbonyl-3-(3-methoxycarbonylbenzoyl) pyridine;
2-methoxycarbonyl-3-(4-methoxycarbonylbenzoyl) pyridine;
2-methoxycarbonyl-3-(3-methoxycarbonyl-4-methylbenzoyl)pyridine;
2-methoxycarbonyl-3-(4-carboxybenzoyl)pyridine;
2-methoxycarbonyl-3-(4-carbamoylbenzoyl)pyridine;
2-methoxycarbonyl-3-(4-N,N-dimethylcarbamoylbenzoyl) pyridine; and
2-methoxycarbonyl-3-(3,4-methylenedioxybenzoyl) pyridine;

there are obtained the following compounds:
5-(3-methoxyphenyl)-7-benzylpyrido[2,3-d]pyridazin-one;
5-(4-methoxyphenyl)-7-benzylpyrido[2,3-d]pyridazin-one;
5-(4-methylphenyl)-7-benzylpyrido[2,3-d]pyridazin-one;
5-(3-bromophenyl)-7-benzylpyrido[2,3-d]pyridazin -8-one;
5-(3-methoxycarbonylphenyl)-7-benzylpyrido[2,3-d]-pyridazin-8-one;
5-(4-methoxycarbonylphenyl)-7-benzylpyrido[2,3-d]-pyridazin-8-one;
5-(3-methoxycarbonyl-4-methylphenyl)-7-benzyl-pyrido[2,3-d]pyridazin-8-one;
5-(4-carboxyphenyl)-7-benzylpyrido[2,3-d]pyridazin-8-one;
5-(4-carbamoylphenyl)-7-benzylpyrido[2,3-d]-pyridazin-8-one;
5-(4- N,N -dimethylcarbamoylphenyl)-7-benzylpyrido-[2,3-d]pyridazin-8-one; and
5-(3,4-methylenedioxyphenyl)-7-benzylpyrido[2,3-d]-pyridazin-8-one.

Example 25

Preparation of 5-(3-chlorophenyl)-7 - ethylpyrido[2,3-d]pyridazin-8-one

25A. Formula I, Where X is carbon, Y is nitrogen, Z is oxygen, $R^1$ is ethyl, $R^3$ is chloro and $R^2$, $R^4$, $R^5$ and $R^6$ are hydrogen.

Following the procedures of Example 17A and substituting for 8-(3-chlorophenyl)pyrido[2,3-d]pyridazin-5-one with 5-(3-chlorophenyl)pyrido[2,3-d]pyridazin-8-one there is obtained 5-(3-chlorophenyl)-7-ethylpyrido[2,3-d] pyridazin-8-one.

25B. Preparation of Other Compounds of Formula I, Where X is carbon, Y is nitrogen, and Z is oxygen.

By following the procedures of Example 25A and substituting for 5-(3 - chlorophenyl)-pyrido[2,3-d]pyridazin-8-one with the following:
5-(3-methoxyphenyl)-pyrido[2,3-d]pyridazin-8-one;
5-(4-methoxyphenyl)-pyrido[2,3-d]pyridazin-8-one;
5-(4- methylphenyl)-pyrido[2,3-d]pyridazin-8-one;
5-(3-bromophenyl)-pyrido[2,3-d]pyridazin-8-one;

5-(3-methoxycarbonylphenyl)-pyrido[2,3-d]pyridazin-one;
5-(4-methoxycarbonylphenyl)-pyrido[2,3-d]pyridazin-one;
5-(3-methoxycarbonyl-4-methylphenyl)-pyrido[2,3-d]-pyridazin-8-one;
5-(4-carboxyphenyl)-pyrido[2,3-d]pyridazin-8-one;
5-(4-carbamoylphenyl)-pyrido[2,3-d]pyridazin-8-one;
5-(4- N,N-dimethylcarbamoylphenyl)-pyrido[2,3-d]-pyridazin-8-one; and
5-(3,4-methylenedioxyphenyl)-pyrido[2,3-d]-pyridazin-8-one;
there are obtained the following compounds:
5-(3-methoxyphenyl)-7-ethylpyrido[2,3-d]pyridazin-8-one;
5-(4-methoxyphenyl)-7-ethylpyrido[2,3-d]pyridazin-8-one;
5-(4-methylphenyl)-7-ethylpyrido[2,3-d]pyridazin-8-one;
5-(3-bromophenyl)-7-ethylpyrido[2,3-d]pyridazin-8-one;
5-(3-methoxycarbonylphenyl)-7-ethylpyrido[2,3-d]-pyridazin-8-one;
5-(4-methoxycarbonylphenyl)-7-ethylpyrido[2,3-d]-pyridazin-8-one;
5-(3-methoxycarbonyl-4-methylphenyl)-7-ethylpyrido-[2,3-d]pyridazin-8-one;
5-(4-carboxyphenyl)-7-ethylpyrido[2,3-d]pyridazin-8-one;
5-(4-carbamoylphenyl)-7-ethylpyrido[2,3-d]-pyridazin-8-one;
5-(4-N,N-dimethylcarbamoylphenyl)-7-ethylpyrido-[2,3-d]pyridazin-8-one; and
5-(3,4-methylenedioxyphenyl)-7-ethylpyrido[2,3-d]-pyridazin-8-one.

Example 26

Preparation of 5-(3 - chlorophenyl)-7-(2-propyl) pyrido[2,3-d]pyridazin-8-one

26A. Formula I, Where X is carbon, Y is nitrogen, Z is oxygen, $R^1$ is 2-propyl, $R^3$ is chloro and $R^2$, $R^4$, $R^5$ and $R^6$ are hydrogen.

Following the procedures of Example 18A and substituting for 8-(3-chlorophenyl) pyrido[2,3-d]pyridazin-5-one with 5-(3- chlorophenyl) pyrido[2,3-d]pyridazin-8-one there is obtained 5-(3-chlorophenyl)-7-(2-propyl) pyrido[2,3-d]-pyridazin-8-one.

26B. Preparation of Other Compounds of Formula I, Where X is carbon, Y is nitrogen, and Z is oxygen.

By following the procedures of Example 26A and substituting for 5-(3-chlorophenyl)-pyrido[2,3-d]pyridazin-8-one with the following:
5-(3-methoxyphenyl)-pyrido[2,3-d]pyridazin-8-one;
5-(4-methoxyphenyl)-pyrido[2,3-d]pyridazin-8-one;
5-(4-methylphenyl)-pyrido[2,3-d]pyridazin-8-one;
5-(3-bromophenyl)-pyrido[2,3-d]pyridazin-8-one;
5-(3-methoxycarbonylphenyl)-pyrido[2,3-d]pyridazin-8-one;
5-(4-methoxycarbonylphenyl)-pyrido[2,3-d]pyridazin-8-one;
5-(3-methoxycarbonyl-4-methylphenyl)- pyrido[2,3-d]-pyridazin-8-one;
5-(4-carboxyphenyl)-pyrido[2,3-d]pyridazin-8-one;
5-(4-carbamoylphenyl)-pyrido[2,3-d]pyridazin-8-one;
5-(4- N,N-dimethylcarbamoylphenyl)-pyrido[2,3-d]-pyridazin-8-one; and
5-(3,4-methylenedioxyphenyl)-pyrido[2,3-d]-pyridazin-8-one;
there are obtained the following compounds:
5-(3-methoxyphenyl)-7-(2-propyl)pyrido[2,3-d]-pyridazin-8-one;
5-(4-methoxyphenyl)-7-(2-propyl)pyrido[2,3-d]-pyridazin-8-one;
5-(4-methylphenyl)-7-(2-propyl)pyrido[2,3-d]-pyridazin-8-one;
5-(3-bromophenyl)-7-(2-propyl)pyrido[2,3-d]-pyridazin-8-one;
5-(3-methoxycarbonylphenyl)-7-(2-propyl)pyrido-[2,3-d]pyridazin-8-one;
5-(4-methoxycarbonylphenyl)-7-(2-propyl) pyrido-[2,3-d]pyridazin-8-one;
5-(3-methoxycarbonyl-4-methylphenyl)-7-(2-propyl)-pyrido[2,3-d]pyridazin-8-one;
5-(4-carboxyphenyl)-7-(2-propyl) pyrido[2,3-d]-pyridazin-8-one;
5-(4-carbamoylphenyl)-7-(2-propyl) pyrido[2,3-d]-pyridazin-8-one;
5-(4- N,N-dimethylcarbamoylphenyl)-7-(2-propyl)-pyrido[2,3-d]pyridazin-8-one; and
5-(3,4-methylenedioxyphenyl)-7-(2-propyl)pyrido-[2,3-d]pyridazin-8-one.

Example 27

Preparation of 5-(3-chlorophenyl)-7-(4-pyridylmethyl)pyrido[2,3-d]pyridazin-8-one 27A. Formula I, Where X is carbon, Y is nitrogen, Z is oxygen, $R^1$ is 4-pyridylmethyl, $R^3$ is chloro and $R^2$, $R^4$, $R^5$ and $R^6$ are hydrogen.

Following the procedures of Example 19A and substituting for 8-(3-chlorophenyl)pyrido[2,3-d]pyridazin-5-one with 5-(3-chlorophenyl)-pyrido[2,3-d]pyridazin-8-one there is obtained 5-(3- chlorophenyl)-7-(4-pyridomethyl)pyrido[2,3-d]-pyridazin-8-one.

27B. Preparation of Other Compounds of Formula I, Where X is carbon, Y is nitrogen, and Z is oxygen.

By following the procedures of Example 27A and substituting for 5-(3-chlorophenyl)-pyrido[2,3-d]pyridazin-one with the following:
5-(3-methoxyphenyl)-pyrido[2,3-d]pyridazin-8-one;
5-(4-methoxyphenyl)-pyrido[2,3-d]pyridazin-8-one;
5-(4-methylphenyl)-pyrido[2,3-d]pyridazin-8-one;
5-(3-bromophenyl)-pyrido[2,3-d]pyridazin-8-one;
5-(3-methoxycarbonylphenyl)-pyrido[2,3-d]pyridazin-8-one;
5-(4-methoxycarbonylphenyl)-pyrido[2,3-d]pyridazin-8-one;
5-(3-methoxycarbonyl-4-methylphenyl)-pyrido[2,3-d]pyridazin-8-one;
5-(4-carboxyphenyl)-pyrido[2,3-d]pyridazin-8-one;
5-(4-carbamoylphenyl)-pyrido[2,3-d]pyridazin-8-one;
5-(4-N,N-dimethylcarbamoylphenyl)-pyrido[2,3-d]-pyridazin-8-one; and
5-(3,4-methylenedioxyphenyl)-pyrido[2,3-d]-pyridazin-8-one;
there are obtained the following compounds:
5-(3-methoxyphenyl)-7-(4-pyridylmethyl)pyrido-[2,3-d]pyridazin-8-one;
5-(4-methoxyphenyl)-7-(4-pyridylmethyl)pyrido-[2,3-d]pyridazin-8-one;
5-(4-methylphenyl)-7-(4-pyridylmethyl)pyrido-[2,3-d]pyridazin-8-one;
5-(3-bromophenyl)-7-(4-pyridylmethyl)pyrido[2,3-d]-pyridazin-8-one;
5-(3-methoxycarbonylphenyl)-7-(4-pyridylmethyl)-pyrido[2,3-d]pyridazin-8-one;
5-(4-methoxycarbonylphenyl)-7-(4-pyridylmethyl)-pyrido[2,3-d]pyridazin-8-one;
5-(3-methoxycarbonyl-4-methylphenyl)-7-(4-pyridylmethyl)pyrido[2,3-d]pyridazin-8-one;

5-(4-carboxyphenyl)-7-(4-pyridylmethyl)pyrido -[2,3-d]
  pyridazin-8-one;
5-(4-carbamoylphenyl)-7-(4-pyridylmethyl)pyrido-[2,3-d]
  pyridazin-8-one;
5-(4- N,N-dimethylcarbamoylphenyl)-7-(4-pyridylmethyl)
  pyrido[2,3-d]pyridazin-8-one; and
5-(3,4-methylenedioxyphenyl)-7-(4-pyridylmethyl)-pyrido
  [2,3-d]pyridazin-8-one.

EXAMPLE 28

Preparation of 2-Methoxycarbonyl-3-benzoylpyridine

28A. Formula II, Where X is carbon, Y is nitrogen and $R^2$, $R^3$, $R^4$, $R^5$ and $R^6$ are hydrogen.

A solution of 2,3-pyridyldicarboxylic anhydride (10 g, 67.1 moles) in dry benzene (80 ml, 888 moles) was stirred at 50°–55° C. while aluminum chloride ($AlCl_3$, 20 g, 148 moles) was gradually added. The mixture was refluxed for 18 hours. The reaction mixture was cooled and poured into 250 ml of 5% aqueous HCl and extracted with ethyl acetate. The ethyl acetate was removed and the residue was dried under vacuum. The residue was dissolved in 500 ml methanol and 4 ml concentrated $H_2SO_4$ (67.1 moles) was added. The solution was refluxed at 80° C. for 24 hours. The mixture was cooled, neutralized with saturated sodium bicarbonate solution and extracted with ethyl acetate. The ethyl acetate extract was washed with saturated brine and dried over sodium sulfate. The solution was filtered and the ethyl acetate removed under vacuum to yield 2-methoxycarbonyl-3-benzoylpyridine (7.92 g, 32.8 moles, 49% crude yield). The product was purified by column chromatography eluting with 5% ethyl acetate in methylene chloride to give after crystallization from ether the purified product (5.61 g, 23 moles, 35% yield), mp 85°–86° C.

Example 29

Preparation of 2-(3-nitrobenzoyl)-3-methoxycarbonylpyridine

29A. Formula II, Where X is nitrogen, Y is carbon, $R^3$ is nitro, and $R^2$, $R^4$, $R^5$ and $R^6$ are hydrogen.

2-Benzoyl-3-methoxycarbonylpyridine (3.86 g, 16.0 moles) was dissolved in $H_2SO_4$ (10 ml) to which a mixture of $HNO_3$ (0.88 ml) and $H_2SO_4$ (2.0 ml) was added dropwise. The reaction mixture was stirred for 30 minutes and poured onto ice. The solution was stirred for 60 minutes, basified to pH 7.8 with saturated sodium bicarbonate and extracted with ethyl acetate. The organic ethyl acetate solution was washed with brine and dried over magnesium sulfate. The solution was filtered and the solvent removed yielding 4.49 g of the crude product, 2-(3-nitrobenzoyl)-3-methoxycarbonylpyridine.

29B. Formula II, Where X is carbon, Y is nitrogen, $R^3$ is nitro, and $R^2$, $R^4$, $R^5$ and $R^6$ are hydrogen.

By following the procedure of Example 29A and substituting 2-methoxycarbonyl-3-benzoylpyridine for 2-benzoyl-3-methoxycarbonylpyridine there is obtained 2-methoxycarbonyl-3-(3-nitrobenzoyl)pyridine.

Example 30

Preparation of 5-(3-nitrophenyl)-pyrido[2,3-d] pyridazin-8-one

30A. Formula I, Where X is carbon, Y is nitrogen, Z is oxygen, $R^3$ is nitro and $R^1$, $R^2$, $R^4$, $R^5$ and $R^6$ are hydrogen.

Following the procedures of Example 5A and substituting for 2-(3-nitrobenzoyl)-3-methoxycarbonylpyridine with 2-methoxycarbonyl-3-(3-nitrobenzoyl)pyridine, as prepared according to the procedure of Example 29B, there is obtained 5-(3-nitrophenyl)- pyrido[2,3-d]pyridazin-8-one.

30B. Preparation of Other Compounds of Formula I, Where X is carbon, Y is nitrogen, and Z is oxygen.

By following the procedures of Example 30A and substituting for 2-methoxycarbonyl-3-(3-nitrobenzoyl)pyridine with the following:

2-methoxycarbonyl-3-(3-methoxybenzoyl)pyridine;
2-methoxycarbonyl-3-(4-methoxybenzoyl)pyridine;
2-methoxycarbonyl-3-(4-methylbenzoyl)pyridine;
2-methoxycarbonyl-3-(3-bromobenzoyl)pyridine;
2-methoxycarbonyl-3-(3-chlorobenzoyl)pyridine;
2-methoxycarbonyl-3-(3-methoxycarbonylbenzoyl) pyridine;
2-methoxycarbonyl-3-(4-methoxycarbonylbenzoyl) pyridine;
2-methoxycarbonyl-3-(3-methoxycarbonyl-4-methylbenzoyl)pyridine;
2-methoxycarbonyl-3-(4-carboxybenzoyl)pyridine;
2-methoxycarbonyl-3-(4-carbamoylbenzoyl)pyridine;
2-methoxycarbonyl-3-(4-N,N-dimethylcarbamoylbenzoyl) pyridine; and
2-methoxycarbonyl-3-(3,4-methylenedioxybenzoyl)-pyridine;

there are obtained the following compounds:
5-(3-methoxyphenyl)-pyrido[2,3-d]pyridazin-8-one;
5-(4-methoxyphenyl)-pyrido[2,3-d]pyridazin-8-one;
5-(4-methylphenyl)-pyrido[2,3-d]pyridazin-8-one;
5-(3-bromophenyl)- pyrido[2,3-d]pyridazin-8-one;
5-(3- chlorophenyl)-pyrido[2,3-d]pyridazin-8-one;
5-(3-methoxycarbonylphenyl)-pyrido[2,3-d]pyridazin-8-one;
5-(4-methoxycarbonylphenyl)-pyrido[2,3-d]pyridazin-8-one;
5-(3-methoxycarbonyl-4-methylphenyl)-pyrido[2,3-d] pyridazin-8-one;
5-(4-carboxyphenyl)-pyrido[2,3-d]pyridazin-8-one;
5-(4-carbamoylphenyl)-pyrido[2,3-d]pyridazin-8-one;
5-(4-N,N-dimethylcarbamoylphenyl)-pyrido[2,3-d]-pyridazin-8-one; and
5-(3,4-methylenedioxyphenyl)-pyrido[2,3-d]pyridazin-8-one.

Example 31

Preparation of 5-(3-nitrophenyl)-7-phenylpyrido[2,3-d]pyridazin-8-one

31A. Formula I, Where X is carbon, Y is nitrogen, Z is oxygen, $R^1$ is phenyl, $R^3$ is nitro and $R^2$, $R^4$, $R^5$ and $R^6$ are hydrogen.

Following the procedures of Example 6A and substituting for 2-(3-nitrobenzoyl)-3-methoxycarbonylpyridine with 2-methoxycarbonyl-3-(3-nitrobenzoyl) pyridine there is obtained 5-(3- nitrophenyl)-7-phenylpyrido[2,3-d] pyridazin-8-one.

31B. Preparation of Other Compounds of Formula I, Where X is carbon, Y is nitrogen, and Z is oxygen.

By following the procedures of Example 31A and substituting for 2-methoxycarbonyl-3-(3-nitrobenzoyl)pyridine with the following:

2-methoxycarbonyl-3-(3-methoxybenzoyl)pyridine;
2-methoxycarbonyl-3-(4-methoxybenzoyl)pyridine;
2-methoxycarbonyl-3-(4-methylbenzoyl)pyridine;
2-methoxycarbonyl-3-(3-bromobenzoyl)pyridine;

2-methoxycarbonyl-3-(3-chlorobenzoyl)pyridine;
2-methoxycarbonyl-3-(3-methoxycarbonylbenzoyl) pyridine;
2-methoxycarbonyl-3-(4-methoxycarbonylbenzoyl) pyridine;
2-methoxycarbonyl-3-(3-methoxycarbonyl-4-methylbenzoyl)pyridine;
2-methoxycarbonyl-3-(4-carboxybenzoyl)pyridine;
2-methoxycarbonyl-3-(4-carbamoylbenzoyl)pyridine;
2-methoxycarbonyl-3-(4-N,N-dimethylcarbamoylbenzoyl) pyridine; and
2- methoxycarbonyl-3-(3,4-methylenedioxybenzoyl) pyridine;

there are obtained the following compounds:
5-(3-methoxyphenyl)-7-phenylpyrido[2,3-d]pyridazin-8-one;
5-(4-methoxyphenyl)-7-phenylpyrido[2,3-d]pyridazin-8-one;
5-(4-methylphenyl)-7-phenylpyrido[2,3-d]pyridazin-8-one;
5-(3-bromophenyl)-7-phenylpyrido[2,3-d]pyridazin-8-one;
5-(3-chlorophenyl)-7-phenylpyrido[2,3-d]pyridazin-8-one;
5-(3-methoxycarbonylphenyl)-7-phenylpyrido[2,3-d]pyridazin -8-one;
5-(4-methoxycarbonylphenyl)-7-phenylpyrido[2,3-d]pyridazin-8-one;
5-(3-methoxycarbonyl -4-methylphenyl)-7-phenylpyrido[2,3-d]pyridazin-8-one;
5-(4-carboxyphenyl)-7-phenylpyrido[2,3-d]pyridazin-8-one;
5-(4-carbamoylphenyl)-7-phenylpyrido[2,3-d]-pyridazin-8-one;
5-(4-N,N-dimethylcarbamoylphenyl)-7-phenylpyrido-[2,3-d]pyridazin-8-one; and
5-(3,4-methylenedioxyphenyl)-7-phenylpyrido[2,3-d]-pyridazin-8-one.

Example 32

Preparation of 5-(3-nitrophenyl)-7-benzylpyrido[2,3-d]pyridazin-8-one

32A. Formula I, Where X is carbon, Y is nitrogen, Z is oxygen, $R^1$ is benzyl, $R^3$ is nitro and $R^2$, $R^4$, $R^5$ and $R^6$ are hydrogen.

Following the procedures of Example 7A and substituting for 2-(3-nitrobenzoyl)-3-methoxycarbonylpyridine with 2-methoxycarbonyl-3-(3-nitrobenzoyl) pyridine there is obtained 5-(3-nitrophenyl)-7-benzylpyrido[2,3-d]pyridazin-8-one.

32B. Preparation of Other Compounds of Formula I, Where X is carbon, Y is nitrogen, and Z is oxygen.

By following the procedures of Example 32A and substituting for 2-methoxycarbonyl-3-(3-nitrobenzoyl)pyridine with the following:
2-methoxycarbonyl-3-(3-methoxybenzoyl)pyridine;
2-methoxycarbonyl-3-(4-methoxybenzoyl)pyridine;
2-methoxycarbonyl-3-(4-methylbenzoyl)pyridine;
2-methoxycarbonyl-3-(3-bromobenzoyl)pyridine;
2-methoxycarbonyl-3-(3-chlorobenzoyl)pyridine;
2-methoxycarbonyl-3-(3-methoxycarbonylbenzoyl) pyridine;
2-methoxycarbonyl-3-(4-methoxycarbonylbenzoyl) pyridine;
2-methoxycarbonyl-3-(3-methoxycarbonyl-4-methylbenzoyl)pyridine;
2-methoxycarbonyl-3-(4-carboxybenzoyl)pyridine;
2-methoxycarbonyl-3-(4-carbamoylbenzoyl) pyridine;
2-methoxycarbonyl-3-(4-N,N-dimethylcarbamoylbenzoyl) pyridine; and
2-methoxycarbonyl-3-(3,4-methylenedioxybenzoyl) pyridine;

there are obtained the following compounds:
5-(3-methoxyphenyl)-7-benzylpyrido[2,3-d]pyridazin-8-one;
5-(4-methoxyphenyl)-7-benzylpyrido[2,3-d]pyridazin-8-one;
5-(4-methylphenyl)-7-benzylpyrido[2,3-d]pyridazin-8-one;
5-(3-bromophenyl)-7-benzylpyrido[2,3-d]pyridazin-8-one;
5-(3-chlorophenyl)-7-benzylpyrido[2,3-d]pyridazin-8-one;
5-(3-methoxycarbonylphenyl)-7-benzylpyrido[2,3-d]-pyridazin-8-one;
5-(4-methoxycarbonylphenyl)-7-benzylpyrido[2,3-d]-pyridazin-8-one;
5-(3-methoxycarbonyl -4-methylphenyl)-7-benzylpyrido[2,3-d]pyridazin-8-one;
5-(4-carboxyphenyl)-7-benzylpyrido[2,3-d]pyridazin-8-one;
5-(4-carbamoylphenyl)-7-benzylpyrido[2,3-d]-pyridazin-8-one;
5-(4-N,N-dimethylcarbamoylphenyl)-7-benzylpyrido-[2,3-d]pyridazin-8-one; and
5-(3,4-methylenedioxyphenyl)-7-benzylpyrido[2,3-d]-pyridazin-8-one.

Example 33

Preparation of 5-(3-nitrophenyl)-7 -ethylpyrido[2,3-d]pyridazin-8-one

33A. Formula I, Where X is carbon, Y is nitrogen, Z is oxygen, $R^1$ is ethyl, $R^3$ is nitro and $R^2$, $R^4$, $R^5$ and $R^6$ are hydrogen.

Following the procedures of Example 8A and substituting for 8-(3-nitrophenyl) pyrido[2,3-d]pyridazin-5-one with 5-(3-nitrophenyl)-pyrido[2,3-d]pyridazin-8-one there is obtained 5-(3-nitrophenyl)-7-ethylpyrido[2,3-d]pyridazin-8-one.

33B. Preparation of Other Compounds of Formula I, Where X is carbon, Y is nitrogen, and Z is oxygen.

By following the procedures of Example 33A and substituting for 5-(3-nitrophenyl)-pyrido[2,3-d]pyridazin-8-one with the following:
5-(3-methoxyphenyl)-pyrido[2,3-d]pyridazin-8-one;
5-(4-methoxyphenyl)-pyrido[2,3-d]pyridazin-8-one;
5-(4-methylphenyl)-pyrido[2,3-d]pyridazin-8-one;
5-(3-bromophenyl)-pyrido[2,3-d]pyridazin-8-one;
5-(3-chlorophenyl)-pyrido[2,3-d]pyridazin-8-one;
5-(3-methoxycarbonylphenyl)- pyrido[2,3-d]pyridazin-8-one;
5-(4-methoxycarbonylphenyl)-pyrido[2,3-d]pyridazin-8-one;
5-(3-methoxycarbonyl-4-methylphenyl)-pyrido[2,3-d] pyridazin-8-one;
5-(4-carboxyphenyl)-pyrido[2,3-d]pyridazin-8-one;
5-(4-carbamoylphenyl)-pyrido[2,3-d]pyridazin-8-one
5-(4-N,N-dimethylcarbamoylphenyl)-pyrido[2,3-d]-pyridazin-8-one; and
5-(3,4-methylenedioxyphenyl)-pyrido[2,3-d]pyridazin-8-one;

there are obtained the following compounds:
5-(3-methoxyphenyl)-7-ethylpyrido[2,3-d]pyridazin-8-one;
5-(4-methoxyphenyl)-7-ethylpyrido[2,3-d]pyridazin-8-one;
5-(4-methylphenyl)-7-ethylpyrido[2,3-d]pyridazin-8-one;
5-(3-bromophenyl)-7-ethylpyrido[2,3-d]pyridazin-8-one;
5-(3-chlorophenyl)-7-ethylpyrido[2,3-d]pyridazin-8-one;
5-(3-methoxycarbonylphenyl)-7-ethylpyrido[2,3-d] pyridazin-8-one;

5-(4-methoxycarbonylphenyl)-7-ethylpyrido[2,3-d]-pyridazin-8-one;
5-(3-methoxycarbonyl-4-methylphenyl)-7-ethylpyrido-[2,3-d]pyridazin-8-one;
5-(4-carboxyphenyl)-7-ethylpyrido[2,3-d]pyridazin-8-one;
5-(4-carbamoylphenyl)-7-ethylpyrido[2,3-d]-pyridazin-8-one;
5-(4-N,N-dimethylcarbamoylphenyl)-7-ethylpyrido-[2,3-d]pyridazin-8-one; and
5-(3,4-methylenedioxyphenyl)-7-ethylpyrido[2,3-d]-pyridazin-8-one.

Example 34

Preparation of 5-(3-nitrophenyl)-7-(4-pyridylmethyl) pyrido[2,3-d]pyridazin-8-one 34A. Formula I, Where X is carbon, Y is nitrogen, Z is oxygen, $R^1$ is 4-pyridylmethyl, $R^3$ is nitro and $R^2$, $R^4$, $R^5$ and $R^6$ are hydrogen.

Following the procedures of Example 9A and substituting for 8-(3-nitrophenyl) pyrido[2,3-d]pyridazin-5-one with 5-(3-nitrophenyl)-pyrido[2,3-d]pyridazin-8-one there is obtained 5-(3-nitrophenyl)-7-(4-pyridomethyl) pyrido[2,3-d]-pyridazin-8-one.

34B. Preparation of Other Compounds of Formula I, Where X is carbon, Y is nitrogen, and Z is oxygen.

By following the procedures of Example 34A and substituting for 5-(3-nitrophenyl)-pyrido[2,3-d]pyridazin-8-one with the following:

5-(3-methoxyphenyl)- pyrido[2,3-d]pyridazin-8-one;
5-(4-methoxyphenyl)-pyrido[2,3-d]pyridazin-8-one;
5-(4-methylphenyl)-pyrido[2,3-d]pyridazin-8-one;
5-(3-bromophenyl)- pyrido[2,3-d]pyridazin-8-one;
5-(3-chlorophenyl)-pyrido[2,3-d]pyridazin-8-one;
5-(3-methoxycarbonylphenyl)-pyrido[2,3-d]pyridazin-8-one;
5-(4-methoxycarbonylphenyl)-pyrido[2,3-d]pyridazin-8-one;
5-(3-methoxycarbonyl -4-methylphenyl)-pyrido[2,3-d]pyridazin-8-one;
5-(4-carboxyphenyl)- pyrido[2,3-d]pyridazin-8-one;
5-(4-carbamoylphenyl)- pyrido[2,3-d]pyridazin-8-one;
5-(4-N,N-dimethylcarbamoylphenyl)-pyrido[2,3-d]-pyridazin-8-one; and
5-(3,4-methylenedioxyphenyl)-pyrido[2,3-d]-pyridazin-8-one;

there are obtained the following compounds:

5-(3-methoxyphenyl)-7-(4-pyridomethyl)pyrido-[2,3-d]pyridazin-8-one;
5-(4-methoxyphenyl)-7-(4-pyridomethyl)pyrido-[2,3-d]pyridazin-8-one;
5-(4-methylphenyl)-7-(4-pyridomethyl)pyrido[2,3-d]-pyridazin-8-one;
5-(3-bromophenyl)-7-(4-pyridomethyl)pyrido[2,3-d]-pyridazin-8-one;
5-(3-chlorophenyl)-7-(4-pyridomethyl)pyrido[2,3-d]-pyridazin-8-one;
5-(3-methoxycarbonylphenyl)-7-(4-pyridomethyl)pyrido[2,3-d]pyridazin-8-one;
5-(4-methoxycarbonylphenyl)-7-(4-pyridomethyl)pyrido[2,3-d]pyridazin-8-one;
5-(3-methoxycarbonyl -4-methylphenyl)-7-(4-pyridomethyl)pyrido[2,3-d]pyridazin-8-one;
5-(4-carboxyphenyl)-7-(4-pyridomethyl)pyrido-[2,3-d]pyridazin-8-one;
5-(4-carbamoylphenyl)-7-(4-pyridomethyl)pyrido-[2,3-d]pyridazin-8-one;
5-(4-N,N-dimethyl carbamoylphenyl)-7-(4-pyridomethyl)pyrido[2,3-d]pyridazin-8-one; and
5-(3,4-methylenedioxyphenyl)-7-(4-pyridomethyl)pyrido[2,3-d]pyridazin-8-one.

Example 35

Preparation of 6-(3-thienylmethyl)-8-(3-chlorophenyl) pyrido[2,3-d]pyridazin -5-one 35A. Formula I, Where X is nitrogen, Y is carbon, Z is oxygen, $R^1$ is 3-thiophenemethyl, $R^3$ is chloro and $R^2$, $R^4$, $R^5$ and $R^6$ are hydrogen.

To a suspension of 8-(3-chlorophenyl) pyrido[2,3-d]pyridazin-5-one (0.21 g, 0.82 mmoles) in tetrahydrofuran (25 ml) was added 3-thiophenemethanol (0.085 ml, 0.9 moles) and triphenyl phosphine (0.32 g, 1.22 moles). To this mixture was added a solution of diisopropyl azodicarboxylate (0.24 ml, 1.22 moles) in tetrahydrofuran (5 ml) in a dropwise manner. The solution was stirred for 3 hours at room temperature. The solvent was removed and the residue chromatographed from hot methanol, yielding 0.15 g of 6-(3-thienylmethyl)-8-(3-chlorophenyl) pyrido[2,3-d]pyridazin-5-one, mp 165°–166° C.

35B. Preparation of Other Compounds of Formula I Where X is nitrogen, Y is carbon, and Z is oxygen.

Following the procedures of Example 35A and substituting for 3-thiophenemethanol with the following:

4-(2-hydroxyethyl)morpholine;
3-pyridinepropanol;
2-(hydroxyethyl)pyridine;
1-(2-hydroxyethyl)pyrrolidine; and
1-(2-hydroxyethyl )-2-pyrrol idinone, their were obtained the following compounds:

6-[4-(2-hydroxyethyl)morpholinyl]-8-(3-chlorophenyl) pyrido[2,3-d]pyridazin-5-one, mp 135° C.;
6-(3-pyridopropyl )-8-(3-chlorophenyl)pyrido[2,3-d]-pyridazin-5-one, mp 91° C.;
6-[2-(hydroxyethyl)pyridyl]-8-(3-chlorophenyl)-pyrido[2,3-d]pyridazin-5-one, mp 98° C.;
6-[1-(2-hydroxyethyl)pyrrolidyl]-8-(3-chlorophenyl)pyrido [2,3-d]pyridazin-5-one, mp 149° C.; and
6-[1-(2-hydroxyethyl )-2-pyrrolidinonyl]-8(3-chlorophenyl) pyrido[2,3-d]pyridazin-5-one, mp 78° C.

35C. Preparation of Other Compounds of Formula I Where X is nitrogen, Y is carbon, and Z is oxygen.

Following the procedures of Example 35A and substituting for 3-thiophenemethanol with the following:

furfuryl methanol;
4-(hydroxymethyl)imidazole;
2-thiophene methanol;
1-piperidine ethanol;
1-methyl-2-piperidine ethanol; and
1-methyl -3-piperidine ethanol, there are obtained the following respective compounds:

6-(furfurylmethyl)-8-(3-chlorophenyl) pyrido[2,3-d]-pyridazin-5-one;
6-[4-(hydroxymethyl)imidazolyl]-8(3-chlorophenyl) pyrido [2,3-d]pyridazin-5-one;
6-(2-thienylmethyl )-8-(3-chlorophenyl)pyrido-[2,3-d]pyridazin-5-one;
6-(1-piperidylethyl )-8-(3-chlorophenyl)pyrido-[2,3-d]pyridazin -5-one;
6-(1-methyl-2-piperidylethyl)-8-(3-chlorophenyl)-pyrido[2,3-d]pyridazin-5-one; and
6-(1-methyl-3-piperidylethyl)-8-(3-chlorophenyl)-pyrido[2,3-d]pyridazin-5-one.

35D. Preparation of Other Compounds of Formula I Where X is nitrogen, Y is carbon, Z fs oxygen, and $R^3$ is nitro.

By following the procedures of Example 35A and substituting for 8-(3-chlorophenyl)pyrido[2,3-d]pyridazin-5-one with 8-(3-nitrophenyl)pyrido[2,3-d]pyridazin-5-one there is obtained:

6-(3-thienylmethyl)-8-(3-nitrophenyl)pyrido[2,3-d]-pyridazin-5-one.

By following the procedures of Examples 35B and 35C and subtituting for 8-(3-chlorophenyl) pyrido[2,3-d]pyridazin-5-one with 8-(3-nitrophenyl) pyrido[2,3-d]pyridazin-5-one there are obtained the following compounds:

6-[4-(2-hydroxyethyl) morpholinyl]-8-(3-nitrophenyl) pyrido[2,3-d]pyridazin-5-one;
6-(3-pyridopropyl)-8-(3-nitrophenyl) pyrido[2,3-d]-pyridazin-5-one;
6-[2-(hydroxyethyl) pyridyl]-8-(3-nitrophenyl)-pyrido[2,3-d]pyridazin-5-one;
6-[1-(2-hydroxyethyl) pyrrolidyl]-8-(3-nitrophenyl)-pyrido[2,3-d]pyridazin-5-one;
6-[1-(2-hydroxyethyl )-2-pyrrolidinonyl]-8(3-nitrophenyl) pyrido[2,3-d]pyridazin-5-one;
6-( furfurylmethyl )-8-(3-nitrophenyl) pyrido[2,3-d]-pyridazin-5-one;
6-[4-(hydroxymethyl)imidazolyl]-8-(3-nitrophenyl)pyrido [2,3-d]pyridazin-5-one;
6-(2-thienylmethyl)-8-(3-nitrophenyl)pyrido[2,3-d]-pyridazin-5-one;
6-(1-piperidylethyl)-8-(3-nitrophenyl)pyrido-[2,3-d]pyridazin-5-one;
6-(1-methyl-2-piperidylethyl)-8-(3-nitrophenyl)-pyrido[2,3-d]pyridazin-5-one; and
6-(1-methyl-3-piperidylethyl)-8-(3-nitrophenyl) pyrido[2,3-d]pyridazin-5-one.

Example 36

Preparation of 6-(4-pyridylmethyl)-8-(3-nitrophenyl)pyrido-[2,3-d]pyridazin-5-one hydrochloride To a suspension of 6-(4-pyridylmethyl)-8-(3-nitrophenyl) pyrido[2,3-d]pyridazin-5-one in methanol is added 5% HCl/MeOH in a dropwise manner with stirring until a clear solution is obtained. The solvent is stripped off. The resulting solid is triturated with ethyl ether. The product is filtered off and dried under vacuum yielding 6-(4-pyridylmethyl)-8-(3-nitrophenyl)pyrido[2,3-d]pyridazin-5-one hydrochloride.

In a similar manner, all compounds of Formula I may be converted to the acid addition salts by treatment with the appropriate acid, for example, hydrobromic acid, sulfuric acid (giving the sulfate and bisulfate salts), nitric acid, phosphoric acid and the like.

Example 37

Prepared Compounds of Formula I

By following the procedures in Examples 1–36 the following compounds were made:
Formula I, where X is nitrogen, Y is carbon, and Z is oxygen.

$R^3$ is chloro, $R^1$ is 2-propyl, $R^2$, $R^4$, $R^5$ and $R^6$ are hydrogen, melting point 80° C.;

$R^3$ is chloro, $R^1$ is 4-pyridylmethyl, $R^2$, $R^4$, $R^5$ and $R^6$ are hydrogen, melting point 152° C.;

$R^3$ is chloro, $R^1$ is N-ethylmorpholinyl, $R^2$, $R^4$, $R^5$ and $R^6$ are hydrogen, melting point 135 ° C.;

$R^3$ is chloro, $R^1$ is N-ethylpyrrolidonyl, $R^2$, $R^4$, $R^5$ and $R^6$ are hydrogen, melting point 78° C.;

$R^3$ is chloro, $R^1$ is 3-thienylmethyl, $R^2$, $R^4$, $R^5$ and $R^6$ are hydrogen, melting point 165° C.;

$R^3$ is chloro, $R^1$ is 4-methoxy-3-pyridylmethyl, $R^2$, $R^4$, $R^5$ and $R^6$ are hydrogen, melting point 145° C.;

$R^3$ is chloro, $R^1$ is 3-pyridylmethyl, $R^2$, $R^4$, $R^5$ and $R^6$ are hydrogen, melting point 165° C.;

$R^3$ is chloro, $R^1$ is n-butyl, $R^2$, $R^4$, $R^5$ and $R^6$ are hydrogen, melting point 119° C.;

$R^3$ is chloro, $R^1$ is methyl, $R^2$, $R^4$, $R^5$ and $R^6$ are hydrogen, melting point 180° C.;

$R^3$ is chloro, $R^1$ is benzyl, $R^2$, $R^4$, $R^5$ and $R^6$ are hydrogen, melting point 111°–112° C.;

$R^3$ is chloro, $R^1$ is ethyl, $R^2$, $R^4$, $R^5$ and $R^6$ are hydrogen, melting point 117° C.;

$R^3$ is chloro, $R^1$, $R^2$, $R^4$, $R^5$ and $R^6$ are hydrogen, melting point 268°–269° C.;

$R^3$ is chloro, $R^1$ is phenyl, $R^2$, $R^4$, $R^5$ and $R^6$ are hydrogen, melting point 144°–145° C.;

$R^3$ is chloro, $R^1$ is N-methylpiperidinyl, $R^2$, $R^4$, $R^5$ and $R^6$ are hydrogen, melting point 142° C.;

$R^3$ is chloro, $R^1$ is 2-pyridylethyl, $R^2$, $R^4$, $R^5$ and $R^6$ are hydrogen, melting point 98° C.;

$R^3$ is chloro, $R^1$ is 3-pyridylpropyl, $R^2$, $R^4$, $R^5$ and $R^6$ are hydrogen, melting point 91° C.;

$R^3$ is chloro, $R^1$ is phenylethyl, $R^2$, $R^4$, $R^5$ and $R^6$ are hydrogen, melting point 108° C.;

$R^3$ is chloro, $R^1$ is cyclopentyl, $R^2$, $R^4$, $R^5$ and $R^6$ are hydrogen, melting point 93° C.;

$R^3$ is chloro, $R^1$ is cyclohexyl, $R^2$, $R^4$, $R^5$ and $R^6$ are hydrogen, melting point 98° C.;

$R^3$ is chloro, $R^1$ is N-ethylpyrrolidinyl, $R^2$, $R^4$, $R^5$ and $R^6$ are hydrogen, melting point 149° C.;

$R^3$ is chloro, $R^1$ is n-propyl, $R^2$, $R^4$, $R^5$ and $R^6$ are hydrogen, melting point 93° C.;

$R^3$ is chloro, $R^1$ is t-butyl, $R^2$, $R^4$, $R^5$ and $R^6$ are hydrogen, melting point 105° C.;

$R^3$ is chloro, $R^1$ is N-methylmorpholinyl, $R^2$, $R^4$, $R^5$ and $R^6$ are hydrogen, melting point 161° C.;

$R^3$ is chloro, $R^1$ is 2-methylaminoethyl and $R^2$, $R^4$, $R^5$ and $R^6$ are hydrogen, melting point 90° C.

$R^3$ is chloro, $R^1$ is cyclopentylmethyl and $R^2$, $R^4$, $R^5$ and $R^6$ are hydrogen, melting point 125° C.

$R^3$ is chloro, $R^1$ is 2-thienylmethyl and $R^2$, $R^4$, $R^5$ and $R^6$ are hydrogen, melting point 175° C.

$R^3$ is chloro, $R^1$ is furfuryl and $R^2$, $R^4$, $R^5$ and $R^6$ are hydrogen, melting point 164° C.

$R^3$ is chloro, $R^1$ is 4-pyridyl-N-oxide-methyl and $R^2$, $R^4$, and $R^6$ are hydrogen, melting point 175°–176° C. (recryst. from MeOH).

$R^3$ is chloro, $R^1$ is dimethylaminoethyl and $R^2$, $R^4$, $R^5$ and $R^6$ are hydrogen, melting point 90° C.

$R^3$ is fluoro, $R^1$ is 4-pyridylmethyl and $R^2$, $R^4$, $R^5$ and $R^6$ are hydrogen, melting point 158° C.

$R^3$ is fluoro, $R^1$ is 3-pyridinylmethyl and $R^2$, $R^4$, $R^5$ and $R^6$ are hydrogen, melting point 151° C.

$R^3$ is fluoro, $R^1$ is ethyl and $R^2$, $R^4$, $R^5$ and $R^6$ are hydrogen, melting point 117°–118° C.

$R^3$ is fluoro, $R^1$ is benzyl and $R^2$, $R^4$, $R^5$ and $R^6$ are hydrogen, melting point 130°–131° C.

$R^3$ is nitro, $R^1$ is 4-pyridylmethyl, $R^2$, $R^4$, $R^5$ and $R^6$ are hydrogen, melting point 172° C.;

$R^3$ is nitro, $R^1$ is 3-pyridylmethyl, $R^2$, $R^4$, $R^5$ and $R^6$ are hydrogen, melting point 190° C.;

$R^3$ is nitro, $R^1$ is 3-thienylmethyl, $R^2$, $R^4$, $R^5$ and $R^6$ are hydrogen, melting point 175° C.;

$R^3$ is nitro, $R^1$ is phenyl, $R^2$, $R^4$, $R^5$ and $R^6$ are hydrogen, melting point 167°–168° C.;

$R^3$ is nitro, $R^1$ is ethyl, $R^2$, $R^4$, $R^5$ and $R^6$ are hydrogen, melting point 138°–139° C.;

$R^3$ is nitro, $R^1$, $R^2$, $R^4$, $R^5$ and $R^6$ are hydrogen, melting point 302°–304° C.;

$R^3$ is nitro, $R^1$ is benzyl, $R^2$, $R^4$, $R^5$ and $R^6$ are hydrogen, melting point 141° C.;

$R^3$ is nitro, $R^1$ is cyclopentylmethyl, $R^2$, $R^4$, $R^5$ and $R^6$ are hydrogen, melting point 88° C.;

$R^3$ is nitro, $R^1$ is dimethylaminoethyl, $R^2$, $R^4$, $R^5$ and $R^6$ are hydrogen, melting point 108° C.;

$R^3$ is nitro, $R^1$ is 2-tetrahydrofuranylmethyl, $R^2$, $R^4$, $R^5$ and $R^6$ are hydrogen, melting point 109° C.;

$R^3$ is nitro, $R^1$ is 3-tetrahydrofuranylmethyl, $R^2$, $R^4$, $R^5$ and $R^6$ are hydrogen, melting point 76° C.;

$R^3$ is nitro, $R^1$ is cyclopropylmethyl, $R^2$, $R^4$, $R^5$ and $R^6$ are hydrogen, melting point 101° C.;

$R^3$ is nitro, $R^1$ is 4-pyridyl-N-oxide-methyl, $R^2$, $R^4$, $R^5$ and $R^6$ are hydrogen, melting point 208° C.;

$R^3$ is nitro, $R^1$ is 2-propyl, $R^2$, $R^4$, $R^5$ and $R^6$ are hydrogen, melting point 126° C.;

$R^3$ is nitro, $R^1$ is 1,2-methylenedioxybenzene-5-methyl, $R^2$, $R^4$, $R^5$ and $R^6$ are hydrogen, melting point 199° C.;

$R^3$ is nitro, $R^1$ is 2-bromoethyl, $R^2$, $R^4$, $R^5$ and $R^6$ are hydrogen, melting point 163° C.;

$R^3$ is nitro, $R^1$ is 2-fluoroethyl, $R^2$, $R^4$, $R^5$ and $R^6$ are hydrogen, melting point 167° C.;

$R^3$ is nitro, $R^1$ is 2-chloroethyl, $R^2$, $R^4$, $R^5$ and $R^6$ are hydrogen, melting point 166° C.;

$R^3$ is nitro, $R^x$ is 3-methylcyclobutyl-3-methyl, $R^2$, $R^4$, $R^5$ and $R^6$ are hydrogen, melting point 159° C.;

$R^3$ is nitro, $R^1$ is 2-cyanoethyl, $R^2$, $R^4$, $R^5$ and $R^6$ are hydrogen, melting point 145° C.;

$R^5$ is nitro, $R^1$ is 3-methyl-3-butenyl, $R^2$, $R^4$, $R^5$ and $R^6$ are hydrogen, melting point 97° C.;

$R^3$ is nitro, $R^1$ is methylthioethyl, $R^2$, $R^4$, $R^5$ and $R^6$ are hydrogen, melting point 96° C.;

$R^3$ is nitro, $R^1$ is 3-methyl-2-butenyl, $R^2$, $R^4$, $R^5$ and $R^6$ are hydrogen, melting point 119° C.;

$R^3$ is nitro, $R^1$ is methoxyethyl, $R^2$, $R^4$, $R^5$ and $R^6$ are hydrogen, melting point 135° C.;

$R^3$ is nitro, $R^1$ is methylthiopropyl, $R^2$, $R^4$, $R^5$ and $R^6$ are hydrogen, melting point 71° C.;

$R^3$ is nitro, $R^1$ is 3,4-dichlorophenyl, $R^2$, $R^4$, $R^5$ and $R^6$ are hydrogen, melting point 168° C.;

$R^3$ is nitro, $R^1$ is 2-hydroxyethyl, $R^2$, $R^4$, $R^5$ and $R^6$ are hydrogen, melting point 155° C.;

$R^3$ is nitro, $R^1$ is 2-thienylmethyl, $R^2$, $R^4$, $R^5$ and $R^6$ are hydrogen, melting point 173° C.;

$R^3$ is nitro, $R^1$ is benzyl, $R^2$, $R^4$, $R^5$ and $R^6$ are hydrogen, melting point 141° C.;

$R^3$ is nitro, $R^1$ is 1-pyrrolidinylethyl, $R^2$, $R^4$, $R^5$ and $R^6$ are hydrogen, melting point 149° C.;

$R^3$ is nitro, $R^1$ is furfuryl, $R^2$, $R^4$, $R^5$ and $R^6$ are hydrogen, melting point 159° C.;

$R^3$ is nitro, $R^1$ is 2-acetoxyethyl, $R^2$, $R^4$, $R^5$ and $R^6$ are hydrogen, melting point 116° C.;

$R^3$ is trifluoromethyl, $R^1$ is cyanoethyl, $R^2$, $R^4$, $R^5$ and $R^6$ are hydrogen, melting point 133° C.;

$R^3$ is trifluoromethyl, $R^1$ is ethyl, $R^2$, $R^4$, $R^5$ and $R^6$ are hydrogen, melting point 116° C.;

$R^3$ is trifluoromethyl, $R^1$ is 3-pyridylmethyl, $R^2$, $R^4$, $R^5$ and $R^6$ are hydrogen, melting point 142° C.;

$R^3$ is trifluoromethyl, $R^1$ is benzyl, $R^2$, $R^4$, $R^5$ and $R^6$ are hydrogen, melting point 137° C.;

$R^3$ is trifluoromethyl, $R^1$ is n-butyl, $R^2$, $R^4$, $R^5$ and $R^6$ are hydrogen, melting point 103° C.;

$R^3$ is cyano, $R^1$ is benzyl, $R^2$, $R^4$, $R^5$ and $R^6$ are hydrogen, melting point 158° C.;

$R^3$ is methyl, $R^1$ is benzyl, $R^2$, $R^4$, $R^5$ and $R^6$ are hydrogen, melting point 88° C.;

$R^3$ is methoxycarbonyl, $R^1$ is benzyl, $R^2$, $R^4$, $R^5$ and $R^6$ are hydrogen, melting point 128°–130° C.;

$R^1$ is benzyl, $R^2$, $R^3$, $R^4$, $R^5$ and $R^6$ are hydrogen, melting point 169°–170° C.;

$R^1$ is 4-pyridylmethyl, $R^2$, $R^3$, $R^4$, $R^5$ and $R^6$ are hydrogen, melting point 175°–176° C.;

$R^1$, $R^2$, $R^3$, $R^4$, $R^5$ and $R^6$ are hydrogen, melting point 230°–231° C.;

$R^1$ is ethyl, $R^3$, $R^2$, $R^4$, $R^5$ and $R^6$ are hydrogen, melting point 114°–115° C.;

$R^1$ is methoxycarbonylmethyl, $R^3$ is nitro, $R^2$, $R^4$, $R^5$ and $R^6$ are hydrogen, melting point 97° C.;

$R^1$ is ethyl, $R^4$ is fluoro, $R^2$, $R^3$, $R^5$ and $R^6$ are hydrogen, melting point 142° C.;

$R^1$ is α-methylbenzyl, $R^3$ is nitro, $R^2$, $R^4$, $R^5$ and $R^6$ are hydrogen, melting point 137° C.;

$R^1$ is α-methylcyclopropylmethyl, $R^3$ is nitro, $R^2$, $R^4$, $R^5$ and $R^6$ are hydrogen, melting point 99° C.;

$R^1$ is 4-(3,5-dimethylisoxazolyl)methyl, $R^3$ is nitro, $R^2$, $R^4$, $R^5$ and $R^6$ are hydrogen, melting point 177° C.;

$R^1$ is benzyl, $R^4$ is fluoro, $R^2$, $R^3$, $R^5$ and $R^6$ are hydrogen, melting point 136° C.;

$R^1$ is 2-cyanoethyl, $R^3$ is chloro, $R^2$, $R^4$, $R^5$ and $R^6$ are hydrogen, melting point 141° C.;

$R^1$ is benzyl, $R^3$ and $R^4$ are chloro, $R^2$, $R^5$ and $R^6$ are hydrogen, melting point 145° C.;

$R^1$ is ethyl, $R^3$ and $R^4$ are chloro, $R^2$, $R^5$ and $R^6$ are hydrogen, melting point 114° C.;

$R^1$ is isopropyl, $R^4$ is fluoro, $R^2$, $R^3$, $R^5$ and $R^6$ are hydrogen, melting point 155° C.;

$R^1$ is propanoyl, $R^3$ is nitro, $R^2$, $R^4$, $R^5$ and $R^6$ are hydrogen, melting point 203° C.;

$R^1$ is hydrogen, $R^3$ and $R^4$ are chloro, $R^2$, $R^5$ and $R^6$ are hydrogen, melting point 272° C.;

$R^1$ is 4-pyridylmethyl, $R^3$ and $R^4$ are chloro, $R^2$, $R^5$ and $R^6$ are hydrogen, melting point 162° C.;

$R^1$ is 2-(1,3-dioxolanyl)methyl, $R^3$ is nitro, $R^2$, $R^4$, $R^5$ and $R^6$ are hydrogen, melting point 129° C.;

$R^1$ is 4-pyridylmethyl, $R^4$ is fluoro, $R^2$, $R^3$, $R^5$ and $R^6$ are hydrogen, melting point 144° C.;

$R^1$ is methoxycarbonylmethyl, $R^3$ is nitro, $R^2$, $R^4$, $R^5$ and $R^6$ are hydrogen, melting point 128° C.;

$R^1$ is α-methylcyclopropylmethyl, $R^3$ is chloro, $R^2$, $R^4$, $R^5$ and $R^6$ are hydrogen, melting point 76° C.;

$R^1$ is methoxycarbonylpropyl, $R^3$ is nitro, $R^2$, $R^4$, $R^5$ and $R^6$ are hydrogen, melting point 95° C.;

$R^1$ is isopropyl, $R^3$ and $R^4$ are chloro, $R^2$, $R^5$ and $R^6$ are hydrogen, melting point 133° C.;

$R^1$ is 4-pyridylmethyl, $R^4$ is chloro, $R^2$, $R^3$, $R^5$ and $R^6$ are hydrogen, melting point 162° C.;

$R^1$ is benzyl, $R^4$ is chloro, $R^2$, $R^3$, $R^5$ and $R^6$ are hydrogen, melting point 133° C.;

$R^1$ is 3-(2-chloropyridyl)methyl, $R^3$ is nitro, $R^2$, $R^4$, $R^5$ and $R^6$ are hydrogen, melting point 177° C.;

$R^1$ is 3-pyridonylmethyl, $R^3$ is nitro, $R^2$, $R^4$, $R^5$ and $R^6$ are hydrogen, melting point 258° C.;

$R^1$ is methyl, $R^3$ is nitro, $R^2$, $R^4$, $R^5$ and $R^6$ are hydrogen, melting point 188° C.;

$R^1$ is 2-chloro-6-methyl-4-pyridylmethyl, $R^3$ is chloro, $R^2$, $R^4$, $R^5$ and $R^6$ are hydrogen, melting point 157° C.;

$R^1$ is cyclopropylmethyl, $R^3$ is chloro, $R^2$, $R^4$, $R^5$ and $R^6$ are hydrogen, melting point 146° C.;

$R^1$ is 2-trifluoroethyl, $R^3$ is chloro, $R^2$, $R^4$, $R^5$ and $R^6$ are hydrogen, melting point 153° C.;

$R^1$ is allyl, $R^3$ is nitro, $R^2$, $R^4$, $R^5$ and $R^6$ are hydrogen, melting point 99° C.;

$R^1$ is ethyl, $R^4$ is chloro, $R^2$, $R^3$, $R^5$ and $R^6$ are hydrogen, melting point 120° C.;

$R^1$ is 1-methyl-3-pyridonylmethyl, $R^3$ is chloro, $R^2$, $R^4$, $R^5$ and $R^6$ are hydrogen, melting point 171° C.;

$R^1$ is 5-(4-methylthiazolyl)ethyl, $R^3$ is chloro, $R^2$, $R^4$, $R^5$ and $R^6$ are hydrogen, melting point 158° C.;

$R^1$ is α-methylbenzyl, $R^3$ is chloro, $R^2$, $R^4$, $R^5$ and $R^6$ are hydrogen, melting point 99° C.;

$R^1$ is 2-chloro-6-methyl-4-pyridylmethyl, $R^3$ is nitro, $R^2$, $R^4$, $R^5$ and $R^6$ are hydrogen, melting point 192° C.;

$R^1$ is 3-methylpyridyl N-oxide, $R^3$ is nitro, $R^2$, $R^4$, $R^5$ and $R^6$ are hydrogen, melting point 222° C.;

$R^1$ is 1-methyl-3-pyridonylmethyl, $R^3$ is nitro, $R^2$, $R^4$, $R^5$ and $R^6$ are hydrogen, melting point 214° C.;

$R^1$ is 3-pyridonylmethyl, $R^3$ is chloro, $R^2$, $R^4$, $R^5$ and $R^6$ are hydrogen, melting point 233° C.;

$R^1$ is (±)tetrahydro-3-furanmethyl, $R^3$ is chloro, $R^2$, $R^4$, $R^5$ and $R^6$ are hydrogen, melting point 118° C.;

$R^1$ is 2-methoxy-5-pyridylmethyl, $R^3$ is chloro, $R^2$, $R^4$, $R^5$ and $R^6$ are hydrogen, melting point 145° C.;

$R^1$ is (±)tetrahydro-2-furanmethyl, $R^3$ is chloro, $R^2$, $R^4$, $R^5$ and $R^6$ are hydrogen, melting point 113° C.;

$R^1$ is 5-(4-methylthiazolyl)ethyl, $R^3$ is nitro, $R^2$, $R^4$, $R^5$ and $R^6$ are hydrogen, melting point 141° C.;

$R^1$ is 2-chloro-4-pyridylmethyl, $R^3$ is chloro, $R^2$, $R^4$, $R^5$ and $R^6$ are hydrogen, melting point 163° C.;

$R^1$ is 2-methoxy-5-pyridylmethyl, $R^3$ is nitro, $R^2$, $R^4$, $R^5$ and $R^6$ are hydrogen, melting point 141° C.;

$R^1$ is isopropyl, $R^4$ is chloro, $R^2$, $R^3$, $R^5$ and $R^6$ are hydrogen, melting point 132° C.;

$R^1$ is propargyl, $R^3$ is nitro, $R^2$, $R^4$, $R^5$ and $R^6$ are hydrogen, melting point 162° C.;

$R^1$ is carboxymethyl, $R^3$ is nitro, $R^2$, $R^4$, $R^5$ and $R^6$ are hydrogen, melting point 204° C.;

$R^1$ is 8-(6-fluorobenzo-1,3-dioxanyl)methyl, $R^3$ is nitro, $R^2$, $R^4$, $R^5$ and $R^6$ are hydrogen, melting point 161° C.;

$R^1$ is 3-[5-(4-methoxyphenyl)-1,2,4-oxadiazolyl)methyl], $R^3$ is nitro, $R^2$, $R^4$, $R^5$ and $R^6$ are hydrogen, melting point 168° C.;

$R^1$ is carboxybutyl, $R^3$ is nitro, $R^2$, $R^4$, $R^5$ and $R^6$ are hydrogen, melting point 152° C.;

$R^1$ is 1-(2-methyl-5-nitroimidazolyl)ethyl, $R^3$ is nitro, $R^2$, $R^4$, $R^5$ and $R^6$ are hydrogen, melting point 184° C.;

$R^1$ is 4-[2-(4-chlorophenyl)thiazolyl]methyl, $R^3$ is nitro, $R^2$, $R^4$, $R^5$ and $R^6$ are hydrogen, melting point 206° C.;

$R^1$ is 4-(2-methylthiazolyl)methyl, $R^3$ is nitro, $R^2$, $R^4$, $R^5$ and $R^6$ are hydrogen, melting point 170° C.;

$R^1$ is 4-nitrobenzyl, $R^3$ is nitro, $R^2$, $R^4$, $R^5$ and $R^6$ are hydrogen, melting point 205° C.;

$R^1$ is 3-(5-phenyl-1, 2,4-oxadiazolyl)methyl, $R^3$ is nitro, $R^2$, $R^4$, $R^5$ and $R^6$ are hydrogen, melting point 170° C.;

$R^1$ is 4-[2-(4-methoxybenzyl)thiazolyl]methyl, $R^3$ is nitro, $R^2$, $R^4$, $R^5$ and $R^6$ are hydrogen, 143° C.;

$R^1$ is 3-(1,2,4-oxadiazolyl)methyl, $R^3$ is nitro, $R^2$, $R^4$, $R^5$ and $R^6$ are hydrogen, melting point 116° C.;

$R^1$ is carboxypropyl, $R^3$ is nitro, $R^2$, $R^4$, $R^5$ and $R^6$ are hydrogen, melting point 147° C.;

$R^1$ is 2-furanylmethyl, $R^3$ is methoxy, $R^2$, $R^4$, $R^5$ and $R^6$ are hydrogen, melting point 136° C.;

$R^1$ is methoxycarbonylbutyl, $R^3$ is nitro, $R^2$, $R^4$, $R^5$ and $R^6$ are hydrogen, melting point 76° C.;

$R^1$ is 2-thienylmethyl, $R^3$ is methoxy, $R^2$, $R^4$, $R^5$ and $R^6$ are hydrogen, melting point 113° C.;

$R^1$ is 2-methyloxiranemethyl, $R^3$ is nitro, $R^2$, $R^4$, $R^5$ and are hydrogen, melting point 107° C.;

$R^1$ is 3-[5-(3,5-dimethylisoxazoyl-4-yl)-1,2,4,-oxadiazolyl]methyl, $R^3$ is nitro, $R^2$, $R^4$, $R^5$ and $R^6$ are hydrogen, melting point 190° C.;

$R^1$ is 4-fluorobenzyl, $R^3$ is nitro, $R^2$, $R^4$, $R^5$ and $R^6$ are hydrogen, melting point 155° C.;

$R^1$ is 4-methoxybenzyl, $R^3$ is nitro, $R^2$, $R^4$, $R^5$ and $R^6$ are hydrogen, melting point 205° C.;

$R^1$ is 2-methoxybenzyl, $R^3$ is nitro, $R^2$, $R^4$, $R^5$ and $R^6$ are hydrogen, melting point 189° C.;

$R^1$ is 3-methoxybenzyl, $R^3$ is nitro, $R^2$, $R^4$, $R^5$ and $R^6$ are hydrogen, melting point 162° C.;

$R^1$ is 3-fluorobenzyl, $R^3$ is nitro, $R^2$, $R^4$, $R^5$ and $R^6$ are hydrogen, melting point 139° C.;

$R^1$ is 4-methoxybenzyl, $R^3$ is nitro, $R^2$, $R^4$, $R^5$ and $R^6$ are hydrogen, melting point 155° C.;

$R^1$ is 4-chlorobenzyl, $R^3$ is nitro, $R^2$, $R^4$, $R^5$ and $R^6$ are hydrogen, melting point 177° C.;

$R^1$ is 3,5-dichlorobenzyl, $R^3$ is nitro, $R^2$, $R^4$, $R^5$ and $R^6$ are hydrogen, melting point 189° C.; and $R^1$ is 2-norboranylmethyl, $R^3$ is nitro, $R^2$, $R^4$, $R^5$ and $R^6$ are hydrogen, melting point 153° C.

Formula I, Where X is carbon, Y is nitrogen, and Z is oxygen.

$R^1$ is phenyl, $R^2$, $R^3$, $R^4$, $R^5$ and $R^6$ are hydrogen, having a melting point of 221°–222° C.;

$R^1$, $R^2$, $R^3$, $R^4$, $R^5$ and $R^6$ are hydrogen, having a melting point of 232°–233° C.;

$R^1$ is ethyl, $R^2$, $R^3$, $R^4$, $R^5$ and $R^6$ are hydrogen, having a melting point of 164°–165° C.;

$R^1$ is benzyl, $R^2$, $R^3$, $R^4$, $R^5$ and $R^6$ are hydrogen, having a melting point of 210°–211° C.; and $R^1$ is 4-pyridylmethyl, $R^2$, $R^3$, $R^4$, $R^5$ and $R^6$ are hydrogen, having a melting point of 230°–231° C.

Formula I, Where X is carbon, Y is carbon, and Z is oxygen.

$R^3$ is chloro, $R^1$ is n-butyl, $R^2$, $R^4$, $R^5$ and $R^6$ are hydrogen, melting point 100° C.;

$R^1$ is n-butyl, $R^2$, $R^3$, $R^4$, $R^5$ and $R^6$ are hydrogen, melting point 105° C.;

$R^1$ is n-pentyl, $R^2$, $R^3$, $R^4$, $R^5$ and $R^6$ are hydrogen, melting point 93 ° C.;

$R^3$ is chloro, $R^1$ is 4-pyridylmethyl, $R^2$, $R^4$, $R^5$ and $R^6$ are hydrogen, melting point 131° C.;

$R^3$ is chloro, $R^1$ is ethyl, $R^2$, $R^4$, $R^5$ and $R^6$ are hydrogen, melting point 104° C.;

$R^1$ is methyl, $R^2$, $R^3$, $R^4$, $R^5$ and $R^6$ are hydrogen, melting point 162° C.;

$R^3$ is chloro, $R^1$ is cyclopentyl, $R^2$, $R^4$, $R^5$ and $R^6$ are hydrogen, melting point 139° C.;

$R^3$ is chloro, $R^1$ is 2-propyl, $R^2$, $R^4$, $R^5$ and $R^6$ are hydrogen, melting point 85° C.;

$R^1$ is n-propyl, $R^2$, $R^3$, $R^4$, $R^5$ and $R^6$ are hydrogen, melting point 104° C.;

$R^3$ is trifluoromethyl, $R^1$ is methyl, $R^2$, $R^4$, $R^5$ and $R^6$ are hydrogen, melting point 136° C.;

$R^3$ is nitro, $R^1$ is ethyl, $R^2$, $R^4$, $R^5$ and $R^6$ are hydrogen, melting point 161° C.;

$R^3$ is nitro, $R^1$ is benzyl, $R^2$, $R^4$, $R^5$ and $R^6$ are hydrogen, melting point 150° C.;

$R^3$ is chloro, $R^1$ is hexyl, $R^2$, $R^4$, $R^5$ and $R^6$ are hydrogen, melting point 123° C.;

$R^3$ is chloro, $R^1$ is N-methylmorpholinyl, $R^2$, $R^4$, $R^5$ and $R^6$ are hydrogen, melting point 157° C.;

$R^3$ is trifluoromethyl, $R^1$ is benzyl, $R^2$, $R^4$, $R^5$ and $R^6$ are hydrogen, melting point 54° C.;

$R^3$ is chloro, $R^1$ is N-methylpiperidinyl, $R^2$, $R^4$, $R^5$ and $R^6$ are hydrogen, melting point 143° C.;

$R^1$ is 2-propyl, $R^2$, $R^3$, $R^4$, $R^5$ and $R^6$ are hydrogen, melting point 128° C.;

$R^3$ is chloro, $R^1$ is t-butyl, $R^2$, $R^4$, $R^5$ and $R^6$ are hydrogen, melting point 105° C.;

$R^3$ is chloro, $R^1$ is benzyl, $R^2$, $R^4$, $R^5$ and $R^6$ are hydrogen, melting point 137° C.;

$R^1$, $R^2$, $R^3$, $R^4$, $R^5$ and $R^6$ are hydrogen, melting point 227°–228° C.;

$R^1$ is benzyl, $R^2$, $R^3$, $R^4$, $R^5$ and $R^6$ are hydrogen, melting point 175°–176° C.;

$R^1$ is ethyl, $R^2$, $R^3$, $R^4$, $R^5$ and $R^6$ are hydrogen, melting point 120°–121° C.; and $R^1$ is 4-pyridylmethyl, $R^2$, $R^3$, $R^4$, $R^5$ and $R^6$ are hydrogen, melting point 201°–203° C.

Formula I, where X is nitrogen, Y is carbon, and Z is sulfur.

$R^3$ is chloro, $R^1$ is benzyl, $R^2$, $R^4$, $R^5$ and $R^6$ are hydrogen, melting point 132° C.;

Example 38

Preparation of 6-(4-pyridyl-N-oxide-methyl)-8-(3-chlorophenyl) pyrido[2,3-d]pyridazin-5-one 38A. Formula I, where X is nitrogen, Y is carbon, Z is oxygen, $R^1$ is 4-pyridyl-N-oxide-methyl, $R^3$ is chloro and $R^2$, $R^4$, $R^5$ and $R^6$ are hydrogen.

To a suspension of 8-(3-chlorophenyl)pyrido[2,3-d]pyridazin-5-one (0.50 g, 1.94 moles), 4-pyridylcarbinol N-oxide (0.27 g, 2.13 moles), triphenylphosphine (0.76 g, 2.9 moles) in tetrahydrofuran (50 ml) was added diisopropylazodicarboxylate (0.57 ml, 2.9 moles) in a dropwise fashion. The suspension was stirred under nitrogen for 18 hours at room temperature. The solvent was removed and the product purified by chromatography, eluted with 100% ethylacetate and 10% methanol/ethylacetate to yield 0.382 g of 6-(4-pyridyl-N-oxide-methyl)-8-(3-chlorophenyl)pyrido [2,3-d]pyridazin-5-one (54%), mp 99° C.

38B. Preparation of Other Compounds of Formula I.

By following the procedures of Example 48A and substituting for 8-(3-chlorophenyl)-pyrido[2,3-d]pyridazin-5-one with the following:

8-(3-methoxyphenyl)-pyrido[2,3-d]pyridazin-5-one;
8-(4-methoxyphenyl)-pyrido[2,3-d]pyridazin-5-one;
8-(4-methylphenyl)-pyrido[2,3-d]pyridazin-5-one;
8-(3-bromophenyl)-pyrido[2,3-d]pyridazin-5-one;
8-(3-nitrophenyl)-pyrido[2,3-d]pyridazin-5-one;
8-(3-nitro-4-chlorophenyl)-pyrido[2,3-d]pyridazin-5-one;
8-(3-nitro -4-methylphenyl)-pyrido[2,3-d]pyridazin-5-one;
8-(3-methoxycarbonylphenyl)-pyrido[2,3-d]pyridazin-5-one;
8-(4-methoxycarbonylphenyl)-pyrido[2,3-d]pyridazin-5-one;
8-(3-methoxycarbonyl -4-methylphenyl)-pyrido[2,3-d]pyridazin-5-one;
8-(4-carboxyphenyl)-pyrido[2,3-d]pyridazin-5-one;
8-(4-carbamoylphenyl)-pyrido[2,3-d]pyridazin-5-one;
8-(4-N,N-dimethylcarbamoylphenyl)-pyrido[2,3-d]pyridazin-5-one; and
8-(3,4-methylenedioxyphenyl)-pyrido[2,3-d]-pyridazin-5-one, there are obtained the following compounds:

6-(4-pyridyl-N-oxide-methyl)-8-(3-methoxyphenyl)-pyrido-[2,3-d]pyridazin-5-one;
6-(4-pyridyl-N-oxide-methyl)-8-(4-methoxyphenyl)-pyrido-[2,3-d]pyridazin-5-one;
6-(4-pyridyl-N-oxide-methyl)-8-(4-methylphenyl)-pyrido-[2,3-d]pyridazin-5-one;
6-(4-pyridyl-N-oxide-methyl)-8-(3-bromophenyl)-pyrido-[2,3-d]pyridazin-5-one;
6-(4-pyridyl-N-oxide-methyl)-8-(3-nitrophenyl)-pyrido-[2,3-d]pyridazin-5-one;
6-(4-pyridyl-N-oxide-methyl )-8-(3-nitro-4-chlorophenyl)-pyrido-[2,3-d]pyridazin-5-one;
6-(4-pyridyl-N-oxide-methyl)-8-(3-nitro-4-methylphenyl)-pyrido-[2,3-d]pyridazin-5-one;
6-(4-pyridyl-N-oxide-methyl)-8-(3-methoxycarbonylphenyl)-pyrido-[2,3-d]pyridazin-5-one;
6-(4-pyridyl-N-oxide-methyl)-8-(4-methoxycarbonylphenyl)-pyrido -[2,3-d]pyridazin-5-one;
6-(4-pyridyl-N-oxide-methyl)-8-(3-methoxycarbonyl-methylphenyl)-pyrido-[2,3-d]pyridazin-5-one;
6-(4-pyridyl-N-oxide-methyl)-8-(4-carboxyphenyl)-pyrido-[2,3-d]pyridazin -5-one;
6-(4-pyridyl-N-oxide-methyl)-8-(4-carbamoylphenyl)-pyrido-[2,3-d]pyridazin-5-one;
6-(4-pyridyl-N-oxide-methyl)-8-(4-N,N-dimethylcarbamoylphenyl)-pyrido-[2,3-d]pyridazin-5-one; and
6-(4-pyridyl-N-oxide-methyl)-8-(3,4-methylenedioxyphenyl)-pyrido[2,3-d]pyridazin-5-one.

Example 39

Preparation of 6-(4-pyridyl-N-oxide-methyl)-8-(3-nitrophenyl)pyrido[2,3-d]pyridazin-5-one 39A. Formula I, where X is nitrogen, Y is carbon, Z is oxygen, $R^1$ is 4-pyridyl-N-oxide-methyl, $R^3$ is nitro and $R^2$, $R^4$, $R^5$ and $R^6$ are hydrogen.

To a solution of 8-(3-nitrophenyl)-pyrido[2,3-d]-pyridazin-5-one (0.40 g, 1.5 moles), 4-pyridylcarbinol N-oxide (0.205 g, 1.64 moles), triphenylphosphine (0.587 g, 2.24 moles) in tetrahydrofuran (50 ml) was added diisopropylazodicarboxylate (0.44 ml, 2.24 moles) in a dropwise fashion. The suspension was stirred under nitrogen for 18 hours at room temperature. The solvent was removed and the product purified by chromatography, i.e., eluted with 100% ethylacetate and 10% methanol/ethylacetate. The fractions were combined, the solvent removed yielding 0.390 g of product which was recrystallized from methanol to give 0.237 g of 6-(4-pyridyl-N-oxide-methyl)-8-(3-nitrophenyl)-pyrido[2,3-d]pyridazin-5-one (42.1%), mp 208° C.

39B. Preparation of Other Compounds of Formula I.

By following the procedures of Example 49A and substituting for 8-(3-nitrophenyl)-pyrido[2,3-d]pyridazin-5-one with the following:

8(3-methoxyphenyl)-pyrido[2,3-d]pyridazin-5-one;
8-(4-methoxyphenyl)-pyrido[2,3-d]pyridazin-5-one;
8-(4-methylphenyl)-pyrido[2,3-d]pyridazin-5-one;
8-(3-bromophenyl)-pyrido[2,3-d]pyridazin-5-one;
8-(3-chlorophenyl)-pyrido[2,3-d]pyridazin-5-one;
8-(3-nitro -4-chlorophenyl)-pyrido[2,3-d]pyridazin-5-one;
8-(3-nitro-4-methylphenyl)-pyrido[2,3d]pyridazin-5-one;
8-(3-methoxycarbonylphenyl)-pyrido[2,3-d]pyridazin-5-one;
8-(4-methoxycarbonylphenyl)-pyrido[2,3-d]pyridazin-5-one;
8-(3-methoxycarbonyl -4-methylphenyl)-pyrido[2,3-d]-pyridazin-5-one;
8-(4-carboxyphenyl)-pyrido[2,3-d]pyridazin-5-one;
8-(4-carbamoylphenyl)-pyrido[2,3-d]pyridazin-5-one;
8-(4-N,N-dimethylcarbamoylphenyl)- pyrido[2,3-d]-pyridazin-5-one; and
8-(3,4-methylenedioxyphenyl)- pyrido[2,3-d]-pyridazin-5-one, there are obtained the following compounds:

6-(4-pyridyl-N-oxide-methyl)-8-(3-methoxyphenyl)-5 pyrido -[2,3-d]pyridazin-5-one;
6-(4-pyridyl-N-oxide-methyl)-8-(4-methoxyphenyl)-pyrido -[2,3-d]pyridazin-5-one;
6-(4-pyridyl-N-oxide-methyl)-8-(4-methylphenyl)-pyrido -[2,3-d]pyridazin-5-one;
6-(4-pyridyl-N-oxide-methyl)-8-(3-bromophenyl)-pyrido -[2,3-d]pyridazin-5-one;
6-(4-pyridyl-N-oxide-methyl)-8-(3-chlorophenyl)-pyrido -[2,3-d]pyridazin-5-one;
6-(4-pyridyl-N-oxide-methyl)-8-(3-nitro-4-chlorophenyl)-pyrido -[2,3-d]pyridazin-5-one;
6-(4-pyridyl-N-oxide-methyl)-8-(3-nitro-4-methylphenyl)- pyrido -[2,3-d]pyridazin-5-one;
6-(4-pyridyl-N-oxide-methyl)-8-(3-methoxycarbonylphenyl)-pyrido -[2,3-d]pyridazin-5-one;
6-(4-pyridyl-N-oxide-methyl)-8-(4-methoxycarbonylphenyl)-pyrido -[2,3-d]pyridazin-5-one;
6-(4-pyridyl-N-oxide-methyl)-8-(3-methoxycarbonyl-4-methylphenyl)-pyrido -[2,3-d]pyridazin-5-one;
6-(4-pyridyl-N-oxide-methyl)-8-(4-carboxyphenyl)-pyrido-[2,3-d]pyridazin-5-one;
6-(4-pyridyl-N-oxide-methyl)-8-(4-carbamoylphenyl)- pyrido -[2,3-d]pyridazin-5-one;
6-(4-pyridyl-N-oxide-methyl)-8-(4-N,N-dimethylcarbamoylphenyl)-pyrido[2,3-d]pyridazin-5-one; and
6-(4-pyridyl-N-oxide-methyl)-8-(3,4-methylenedioxyphenyl)-pyrido-[2,3-d]pyridazin-5-one.

Example 40

Preparation of 6-(n-butyl)-pyrrolo[3,4-b]-pyridine -5,7-dione

Formula 11, where X is nitrogen, Y is carbon and $R^7$ is n-butyl

A suspension of 2,3-pyridinyldicarboxylic anhydride (90 g, 603 moles) was prepared with 400 mL of ethyl acetate. The mixture was cooled to 3° C. and n-butylamine (61 mL, 610 moles) was added at such a rate that the temperature remained below 25° C. Following the addition, the cooling bath was removed and thionyl chloride (51 mL, 700 moles) was added at such a rate that the temperature remained below 50° C. The mixture was stirred for 1 hour. The resulting suspension was then cooled to 5° C. and dilute sodium hydroxide (240 mL of a 6M solution, 1.4 moles) was added at such a rate that the temperature remained below 35° C. The resulting layers were separated. The bulk of the ethyl acetate was removed by atmospheric distillation. Methanol (500 mL) was then added and the distillation continued until 250 mL of solution remained. The solution was allowed to cool during which time crystallization occured. Water (250 mL) was then added and the mixture aged for 18 hours. The product was isolated by filtration and washed twice with 200 mL of a 1:1 (v:v) mixture of water and methanol. After drying 115 g of product 6-(n-butyl)-pyrrolo[3,4-b]pyridine-5,7-dione was obtained.

Example 41

Preparation of 7-Hydroxy-7-phenyl-6-(n-butyl)-6,7-dihydropyrrolo[3,4-b]pyridin-5-one Preparation of Formula 13, Where X Is Nitrogen, Y Is Carbon, $R^7$ Is n-butyl, and $R^2$, $R^3$, $R^4$, $R^5$, $R^6$ Are Hydrogen.

6-(n-Butyl)-pyrrolo[3,4-b]pyridine-5,7-dione(40.4 g, 198 mmoles) was dissolved in toluene (1 L) and cooled to −65° C. Phenylmagnesium chloride (100 mL, 2M in THF, 200 moles) was added over 15 minutes. The cooling bath was then removed and the mixture allowed to warm to −10° C. The reaction was quenched by addition of 25 mL of saturated ammonium chloride solution. The room temperature solution was diluted with 500 mL of ethyl acetate and 500 mL of water. The layers were separated. Removal of most of the organic solvent was accomplished by atmospheric distillation. When the remaining volume reaches 150 mL the mixture was cooled to below 80 C and 1 L of hexanes was added. The resulting crystalline mass was filtered and dried to give 50.6 g of 7-hydroxy-7-phenyl-6-(n-butyl)-6,7-dihydropyrrolo[3,4-b]pyridin-5-one.

Example 42

Preparation of 7-hydroxy-7-(3-nitrophenyl)-7H -furo[3,4-b]pyridin -5-one

Preparation of Formula 15, Where X Is Nitrogen, $R^3$ Is Nitro, And $R^2$, $R^4$, $R^5$, $R^6$ Are Hydrogen 7-Hydroxy-7-phenyl-6-(n-butyl)-6,7-dihydropyrrolo-[3,4-b]pyridin-5-one (47.15 g, 167 moles) was mixed with 250 mL of concentrated sulfuric acid (96%). The resulting mixture was placed in a cooling bath. Nitric acid (70%, 12 mL, 189 moles) was added at such a rate that the temperature remained below 45° C. The mixture was stirred for 30 minutes poured onto ice (500 g) and diluted with 1 L of water. The mixture was extracted twice with 700 mL of ethyl acetate. The organic solvent was removed yielding 7-hydroxy-7-(3-nitrophenyl)-6-(n-butyl)-6,7-dihydropyrrolo[3,4-b]-pyridin-5-one, which was used without further purification.

The 7-hydroxy-7-(3-nitrophenyl)-6-(n-butyl)-6,7-dihydropyrrolo[3,4-b]pyridin-5-one was mixed with 500 mL of water and 250 mL of concentrated hydrochloric acid was added. The mixture was heated under reflux for 20 hours. After cooling the mixture was diluted with 500 mL of water and the solid was removed by filtration. After washing the solid with water (500 mL) and methanol (200 mL) the material was dried to give 39.85 of 7-hydroxy-7-(3-nitrophenyl)-7H-furo[3,4-b]pyridin-5-one.

Example 43

Preparation of 8-(3-nitrophenyl)-pyrido-[2,3-d]pyridazin-5-one

Preparation of Formula I, Where X Is Nitrogen, Y Is Carbon, $R^3$ Is Nitro, And $R^2$, $R^4$, $R^5$, $R^6$ Are Hydrogen 7-Hydroxy-7-(3-nitrophenyl)-7H-furo[3,4-b]pyridin-5-one (38.65 g, 142 mmoles) was mixed with 800 mL of methanol. To this mixture was added 35 mL of anhydrous hydrazine. The resulting solution was then heated under reflux for 5 hours. After 17 hours of aging at room temperature the product was isolated by filtration. The crystalline mass was washed twice with methanol (250 mL) and dried, yielding 25.6 g of 8-(3-nitrophenyl)- pyrido[2,3-d]pyridazin-5-one.

Example 44

Preparation of 6-(4-Pyridylmethyl)-8-(3-nitrophenyl)-pyrido[2,3-d]pyridazin-5-one 44A. Preparation Of Formula I, Where X Is Nitrogen, $R^1$ Is 4-Pyridylmethyl, $R^3$ Is Nitro, And $R^2$, $R^4$, $R^5$, And $R^6$ Are Hydrogen.

8-(3-nitrophenyl)-pyrido[2,3-d]pyridazin-5-one (5.12 g, 19.1 moles), sodium hydride (50% in oil, 1 g, 20.1 moles) were mixed in 100 mL of 1-methyl-2-pyrrolidone and the mixture heated to 65° C. In a separatory funnel, 4-picolyl chloride hydrochloride (4.5 g, 27.4 mmoles), 20 mL of saturated potassium carbonate and 75 mL of toluene are mixed. After separation, the toluene solution was added to the reaction mixture dropwise over the period of 1 hour. The reaction mixture was diluted with water (250 mL) and extracted twice with ethyl acetate (200 mL). After concentrating the organic fractions, methanol and hexanes (75 mL each) were added and the mixture allowed to stir at room temperature for 17 hours. The material was filtered and dried to yield 5.2 g of 6-(4-pyridylmethyl)-8-(3-nitro-phenyl)-pyrido[2,3-d]pyridazin-5-one.

44B. Formula I Varying $R^1$

By following the procedures of Example 44A and substituting for 4-picolyl chloride hydrochloride with the following:

3-picolyl chloride hydrochloride;
2-picolyl chloride hydrochloride;
2-imidazoylmethyl chloride hydrochloride; or
2-imidazoylethyl chloride hydrochloride;
there are obtained the following compounds:
6-(3-pyridylmethyl)-8-(3-nitrophenyl)-pyrido[2,3-d]-pyridazin-5-one;
6-(2-pyridylmethyl)-8-(3-nitrophenyl)-pyrido[2,3-d]-pyridazin-5-one;
6-(2-imidazoylmethyl)-8-(3-nitrophenyl)-pyrido[2,3-d]-pyridazin-5-one; or
6-(2-imidazoylethyl)-8-(3-nitrophenyl)-pyrido[2,3-d]-pyridazin-5-one.

Example 45

Preparation of 6-(4-Pyridyl-N-oxide-methyl)-8-(3-chlorophenyl)-pyrido[2,3-d]pyridazin-5-one 45A. Preparation of Formula I, Where X Is Nitrogen, Y Is Carbon, $R^1$ Is 4-Pyridylmethyl, $R^3$ Is Nitro, And $R^2$, $R^4$, $R^5$, $R^6$ Are Hydrogen 6-(4-pyridylmethyl)-8-(3-nitrophenyl)-pyrido[2,3-d]-pyridazin-5-one (4.2 g, 11.5 moles) was dissolved in 100 mL of methylene chloride. To this solution was added m-chloroperoxybenzoic acid (85%, 4.2 g, 20.7 moles). The solution was stirred for 17 hours. After partitioning between methylene chloride and potassium carbonate the organic layer was directly chromatographed using silica gel. The product was eluted with 20% methanol in ethyl acetate. After solvent removal, and filtering, recrystallization from methanol (200 mL) gave 3.2 g of 6-(4-pyridyl-N-oxide-methyl)-8-(3-chlorophenyl)-pyrido[2,3-d]pyridazin-5-one.

45B. Formula I Varying $R^1$

By following the procedures of Example 45A and substituting for 6-(4-pyridylmethyl)-8-(3-nitrophenyl)-pyrido [2,3-d]pyridazin-5-one with the following:

6-(3-pyridylmethyl)-8-(3-nitrophenyl)-pyrido[2,3-d]-pyridazin-5-one;
6-(2-pyridylmethyl)-8-(3-nitrophenyl)-pyrido[2,3-d]-pyridazin-5-one;
6-(2-imidazoylmethyl )-8-(3-nitrophenyl)-pyrido[2,3-d]-pyridazin-5-one; or
6-(2-imidazoylethyl)-8-(3-nitrophenyl)-pyrido[2,3-d]-pyridazin-5-one;
there are obtained the following compounds:
6-(3-pyridyl-N-oxide-methyl)-8-(3-nitrophenyl)-pyrido-[2,3-d]pyridazin-5-one;
6-(2-pyridyl-N-oxide-methyl)-8-(3-nitrophenyl)-pyrido-[2,3-d]pyridazin-5-one;
6-(2-imidazoyl-N-oxide-methyl)-8-(3-nitrophenyl)-pyrido-[2,3-d]pyridazin-5 -one; or
6-(2-imidazoyl-N-oxide-ethyl)-8-(3-nitrophenyl)-pyrido-[2,3-d]pyridazin-5-one.

Example 46

Preparation of 7-hydroxy-7-(3-chlorophenyl)-7H-furo[3,4-b]pyridin-5-one

Preparation Of Formula 19, Where X Is Nitrogen, Y Is Carbon, $R^7$ Is n-Butyl, $R^3$ Is Chloro And $R^2$, $R^4$, $R^5$, $R^6$ Are Hydrogen.

6-(n-Butyl)-pyrrolo[3,4-b]pyridine-5,7-dione (20 g, 98 mmole) was dissolved in toluene (500 mL) and cooled to −65° C. To this mixture was added 3-chlorophenylmagnesium bromide (prepared by heating under reflux 2.5 g magnesium metal, 20 g of 3-chlorobromobenzene and 100 mL of tetrahydrofuran for 1 hour) at such a rate that the temperature of the reaction remain below −40° C. After the addition was complete, the cooling bath was removed and the mixture was allowed to warm to 0° C. The reaction mixture was quenched with aqueous ammonium chloride (25 mL) diluted with ethyl acetate (250 mL) and water (250 mL). After separating the resulting 2 layers, the organic fraction was dried with sodium sulfate (50 g). Filtration, followed by solvent removal gave 7-hydroxy-7-(3-chlorophenyl)-6-(n-butyl)-6,7-dihydropyrrolo[3,4-b]pyridin-5-one as an oil, which was used in the next reaction without further purification.

To the 7-hydroxy-7-(3-chlorophenyl)-6-(n-butyl)-6,7-dihydropyrrolo[3,4-b]pyridin-5-one was added 500 mL of water, 250 mL of concentrated hydrochloric acid and the mixture was heated under reflux for 24 hours. The solution was then filtered, cooled and made basic with sodium hydroxide. An ethyl acetate extraction removed unhydrolyzed starting material and the pH of the resulting aqueous fraction was adjusted to pH 2 with hydrochloric acid. The resulting aqueous fraction was extracted twice with ethyl acetate (250 mL). The solvent was removed yielding 16 g of 7-hydroxy-7-(3-chlorophenyl)-7H-furo[3,4-b]pyridin-5-one, which was used without further purification.

Example 47

Preparation of 8-(3-chlorophenyl)-pyrido-[2,3-d]pyridazin-5-one

Preparation of Formula I, where X is nitrogen, $R^1$ is n-butyl, $R^3$ is chlorine, and $R^2$, $R^4$, $R^5$, $R^6$ are hydrogen 7-Hydroxy-7-(3-chlorophenyl)-7H-furo[3,4-b]pyridin-5-one was mixed with 100 mL of methanol. To this mixture was added 20 mL of anhydrous hydrazine. The mixture was heated under reflux for 2 hours at which time an additional 100 mL of methanol and 200 mL of xylenes were added. The mixture was heated under reflux for an additional 17 hours. Additional xylenes (200 mL) were added and 200 mL of solvent was distilled. Isolation of the product was accomplished by cooling the reaction mixture and filtration. The resulting crystalline mass was washed with toluene (200 mL) and dried to yield 14.2g of 8-(3-nitrophenyl)-pyrido[2,3-d]pyridazin-5-one.

Example 48

Preparation of 6-(4-pyridylmethyl)-8-(3-chlorophenyl)-pyrido[2,3-d]pyridazin-5-one 48A. Preparation of Formula I, Where X Is Nitrogen, Y Is Carbon, $R^1$ Is 4-Pyridylmethyl, $R^3$ Is Chloro, And $R^2$, $R^4$, $R^5$, $R^6$ Are Hydrogen.

8-(3-nitrophenyl)-pyrido[2,3-d]pyridazin-5-one (14.2 g, 55 mole) and sodium hydride (50% in oil, 2.7 g, 55 mole) were mixed in 150 mL of 1-methyl-2-pyrrolidone and the mixture was heated to 55° C. In a separatory funnel, 4-picolyl chloride hydrochloride (11 g, 67 mmoles), 50 mL of saturated potassium carbonate and 150 mL of toluene were mixed. After separation, the toluene solution was added to the reaction mixture dropwise over the period of 30 minutes. The mixture was heated to 60° C. for an additional 30 minutes, cooled to room temperature and poured into 300 mL of water. The mixture was extracted twice with ethyl acetate (500 mL). After drying the organic fraction with sodium sulfate (50 g), filtering and removal of the solvent the crude product was crystallized from isopropyl acetate (300 mL). The material was filtered and dried to yield 10.5 grams of 6-(2-pyridylmethyl)-8-(3-chlorophenyl)-pyrido[2,3-d]pyridazin-5-one. An additional 4.6 grams of the product was obtained as a second crop by concentration of the filtrates and filtering the resulting crystalline mass.

48B. Formula I Varying $R^1$

By following the procedures of Example 48A and substituting for 4-picolyl chloride hydrochloride with the following:
3-picolyl chloride hydrochloride;
2-picolyl chloride hydrochloride;
2-imidazoylmethyl chloride hydrochloride; or
2-imidazoylethyl chloride hydrochloride;
there are obtained the following compounds:
6-(3-pyridylmethyl)-8-(3-chlorophenyl)-pyrido[2,3-d]pyridazin-5-one;
6-(2-pyridylmethyl)-8-(3-chlorophenyl)-pyrido[2,3-d]pyridazin-5-one;
6-(2-imidazoylmethyl)-8-(3-chlorophenyl)-pyrido[2,3-d]pyridazin-5-one; or
6-(2-imidazoylethyl )-8-(3-chlorophenyl)- pyrido[2,3-d]pyridazin-5-one.

Example 49

Preparation of 6-(4-pyridyl-N-oxide-methyl)-8-(3-chlorophenyl)- pyrido[2,3-d]pyridazin-5-one 49A. Preparation of Formula I, where X is nitrogen, Y Is Carbon, $R^1$ Is 4-Pyridylmethyl, $R^3$ Is Chloro, And $R^2$, $R^4$, $R^5$, $R^6$ Are Hydrogen.

6-(2-Pyridylmethyl)-8-(3-chlorophenyl)-pyrido[2,3-d]-pyridazin-5-one (6 g, 17.2 mole) was mixed with m-chloroperoxybenzoic acid (85%, 4.5 g, 22.1 moles) in methylene chloride (50 mL). The mixture was stirred for 2 hours at room temperature. Saturated sodium carbonate (25 mL) was added the resulting layers separated and the methylene chloride fraction dried with sodium sulfate (25 g). After filtration, the solvent was removed and the resulting solid crystallized from methanol (20 mL). Filtration and drying yielded 3.8 g of 6-(2-pyridyl-N-oxide-methyl)-8-(3-chlorophenyl)-pyrido[2,3-d]pyridazin-5-one.

49B. Formula I Varying $R^1$

By following the procedures of Example 15A and substituting for 6-(2-pyridyl -N-oxide-methyl )-8-(3-chlorophenyl)-pyrido[2,3-d]pyridazin-5-one with the following:
6-(3-pyridylmethyl )-8-(3-chlorophenyl)-pyrido[2,3-d]pyridazin-5-one;
6-(2-pyridylmethyl )-8-(3-chlorophenyl)-pyrido[2,3-d]pyridazin-5-one;
6-(2-imidazoylmethyl)-8-(3-chlorophenyl)-pyrido[2,3-d]-pyridazin-5-one; or
6-(2-imidazoylethyl)-8-(3-chlorophenyl)-pyrido[2,3-d]-pyridazin-5-one
there are obtained the following compounds:
6-(3-pyridyl-N-oxide-methyl)-8-(3-chlorophenyl)-pyrido-[2,3-d]pyridazin-5-one;
6-(2-pyridyl-N-oxide-methyl)-8-(3-chlorophenyl)-pyrido-[2,3-d]pyridazin-5-one;
6-(2-imidazoyl-N-oxide-methyl)-8-(3-chlorophenyl)-pyrido [2,3-d]pyridazin-5-one; or
6-(2-imidazoyl-N-oxide-ethyl)-8-(3-chlorophenyl)-pyrido-[2,3-d]pyridazin-5-one.

Example 50

Preparation of 6-benzyl-8-(3-chlorophenyl)pyrido-[2,3-d]pyridazin-5-thione

Formula I Where X Is Nitrogen, Y Is Carbon, Z Is Sulfur, $R^1$ Is Benzyl, $R^3$ Is Chloro and $R^2$, $R^4$, $R^5$ and $R^6$ Are Hydrogen To a solution of 6-benzyl-8-(3-chlorophenyl)pyrido-[2,3-d]pyridazin-5-one (0.96 g, 2.76 mmoles) in toluene (100 mL) at room temperature under a nitrogen atmosphere was added solid 2,4-bis(4-methoxyphenyl)-1,3-dithia-2,4-diphosphetane-2,4-disulfide (Lawesson's Reagent) (0.67 g, 1.66 mmoles). The reaction mixture was heated under reflux for 18 hours, and then cooled and concentrated. Chromatography on silica gel using ethyl acetate/hexane (1:4) gave 0.233 g of 6-benzyl-8-(3-chlorophenyl)pyrido[2,3-d]pyridazin-5-thione (23.2%), mp 132° C.

Example 51

Preparation of 8-(3-chlorophenyl)-6-(6-methoxy-3-pyridylmethyl)pyrido[2,3-d]pyridazin-5-one Formula I, Where X Is Nitrogen, Y Is Carbon, Z Is Oxygen, $R^1$ is 6-Methoxy-3-pyridylmethyl, $R^3$ Is Chloro, And $R^2$, $R^4$, $R^5$, $R^6$ Are Hydrogen To a suspension of 8-(3-chlorophenyl)pyrido-[2,3-d] pyridazin-5-one (0.515 g, 2.0 moles), 6-methoxy-3-hydroxymethyl pyridine (0.306g, 2.2 moles) and triphenylphosphine (0.792 g, 3.0 moles) in THF (50 mL) was added diisopropylazodicarboxylate (0.6mL, 3.0 moles). The reaction mixture was stirred for 18 hours at room temperature. The solvent was removed and the product was purified by chromatography (ethyl acetate/hexane 2:3) and crystallized from methanol to yield 0.588g of 8-(3-chlorophenyl)

-6-(6-methoxy-3-pyridylmethyl)pyrido[2,3-d]-pyridazin-5-one, mp 145° C.

Example 52

Preparation of 8-(3-chlorophenyl)-6-(3-pyridon-6-yl methyl)pyrido-[2,3-d]pyridazin-5-one Formula I, where X is nitrogen, Y is carbon, Z is oxygen, $R^1$ is 3-pyridon-6-ylmethyl, $R^3$ is chloro, and $R^2$, $R^4$, $R^5$, $R^6$ are hydrogen.

To a solution of 8-(3-chlorophenyl)-6-(6-methoxy-3-pyridylmethyl)pyrido[2,3-d]pyridazin-5-one (0.566 g, 1.5 moles) in acetonitrile was added solid sodium iodide (0.224 g). The suspension was stirred for 30 min at room temperature, and then trimethylsilyl chloride (0.19 mL, 1.5 moles) was added. The reaction mixture was heated under reflux for 18 hours, then allowed to cool. Water (50 mL) was added. The solution was extracted with ethyl acetate, washed with 10% sodium thiosulfate and brine, dried over magnesium sulfate, filtered and concentrated. Chromatography with 10% methanol/ethyl acetate yielded 0.317 g of 8-(3-chlorophenyl)-6-(3-pyridon-6-ylmethyl)pyrido-[2,3-d]pyridazin-5-one, mp 233° C.

Example 53

Preparation of 8-(3-chlorophenyl)-6-(1-methyl-3-pyridon-6-ylmethyl)pyrido[2,3-d]pyridazin-5-one Formula I, Where X Is Nitrogen, Y Is Carbon, Z Is Oxygen, $R^1$ Is 1-Methyl-3-pyridon-6-ylmethyl, $R^3$ Is Chloro, And $R^2$, $R^4$, $R^5$, $R^6$ Are Hydrogen To a suspension of 8-(3-chlorophenyl)-6-(3-pyridon-6-ylmethyl)pyrido-[2,3-d]pyridazin-5-one (0.35 g, 0.96 moles) in DMF (15 mL) was added potassium carbonate (0.16 g, 1.15 mmoles). The suspension was stirred at room temperature for 1 hour under nitrogen, then methyl iodide (0.12 mL) was slowly added via syringe. The reaction mixture was heated under reflux for 18 hours, then allowed to cool. 1N HCl (35 mL) was added, the solid material collected, dried and chromatographed with ethyl acetate and then 5% methanol/ethyl acetate to give 0.055g of 8-(3-chloro-phenyl)-6-(1-methyl-3-pyridon-6-ylmethyl)pyrido [2,3-d]pyridazin-5-one, mp 171° C.

Example 54

Determination of Potency and Selectivity of Inhibitors for PDE IV

Preparation of Human Platelet Phosphodiesterase (PDE III)

Platelet high-affinity cAMP PDE (PDE III) was obtained from human blood in accordance with previously described procedures described in Mol. Pharmacol. 20:302–309, Alvarez, R., Taylor, A., Fazarri, J. J., and Jacobs, J. R. (1981).

Blood was collected into evacuated tubes containing EDTA (7.7 mM, final concentration). PRP was obtained by centrifuging the blood in polycarbonate tubes at 200×g for 15 min at 4° C. A platelet pellet was resuspended in a volume of buffer A (0.137 M NaCl, 12.3 mMTris-HCl buffer, pH 7.7, containing 1 mM $MgCl_2$. The hypotonically-lysed platelet suspension was centrifuged at 48,000×g for 15 min and the supernatant was saved. The pellets were frozen on dry ice and briefly thawed at 22° C. The supernatant was combined with the pellet fraction and the resulting suspension was centrifuged at 48,000×g for 30 min. The supernatant fraction was stored in 0.5 ml aliquots at −20° C. and used as the soluble PDE. Enzyme activity was adjusted to 10–20% hydrolysis after 10 minutes of incubation by dilution with 10mM cold Tris-HCl buffer, pH 7.7.

Preparation of Human Lymphocyte Phosphodiesterase (PDE IV)

Human B cell line (43D) was cultured at 37° C. in 7% $CO_2$ in RPMI 1640 with L-glutamine and 10% Nu-Serum. Prior to the assay ~1.5×10⁸ cells were centrifuged at 1000 rpm for 10 minutes in a table top clinical centrifuge. The pellet was resuspended in 2–3 ml of 45 mMTris-HCl buffer, pH 7.4. The suspension was homogenized and centrifuged at 12,000×g 4° C. for 10 minutes. The supernatant was diluted to 28 ml with Tris-HCl buffer and used directly in the assay or stored at −20° C. The final concentration of DMSO in the PDE incubation medium was 1%. Nitraquazone was included in each assay (10 and 100 µM) as a reference standard.

Human Platelet cAMP Phosphodiesterase Assay

The phosphodiesterase incubation medium contained 10 mM Tris-HCl buffer, pH 7.7, 10 mM $MgSO_4$, 0.1–1 µM [$^3$H]-AMP (0.2 µCi) in a total volume of 1.0 ml. Following addition of the enzyme, the contents were mixed and incubated for 10 min at 30° C. The reaction was terminated by immersing the tubes in a boiling-water bath for 90 sec. After the tubes were cooled in an ice-water bath, 0.1 ml (100µg) of 5'-nucleotidase from snake venom (Crotalus atrox, Sigma V-7000) was added to each tube. The contents were mixed and incubated for 30 min at 30° C. The nucleotidase reaction was terminated by immersing the tubes in a boiling water bath for 60 sec. Labeled adenosine was isolated from alumina coles according to the method described in Anal. Biochem., 52:505–516 (1973), Filburn, C. R., and Karn, J. Assays were performed in triplicate. Hydrolysis of cAMP ranged from 10–20%. Test compounds were dissolved in DMSO. The final concentration of DMSO in the phosphodiesterase assay was 1% when tested with compounds up to 0.1 mM. When tested at 1 mM the DMSO concentration was 10% and this activity was compared to control PDE activity in the presence of 10% DMSO.

Human Lymphocyte cAMP Phosphodiesterase Assay

The phosphodiesterase incubation medium contained 40 mM Tris-HCl buffer, pH 7.7, 0.1 mM $MgSO_4$, 3.75 mM mercaptoethanol, and 0.1–1.0 µM [$^3$H] cAMP (0.2 µCi) in a total volume of 1.0 ml. The reaction was performed and processed according to the procedure used (above) for human platelet PDE. The final concentration of DMSO was 1%.

The compounds of the present invention exhibit potency and selectivity as inhibitors of PDE IV when tested by this method.

| Inhibition of Human Lymphocyte PDE IV | | |
|---|---|---|
| Compound I | $IC_{50}$: | 0.00023 µM |
| Compound II | $IC_{50}$: | 0.001 µM |

Compound I is the compound of Formula I where X is nitrogen and Y is carbon, $R^1$ is 4-pyridylmethyl, $R^3$ is nitro, $R^2$, $R^4$, $R^5$ and $R^6$ are hydrogen, namely 6-(4-pyridylmethyl)-8-(3-nitrophenyl)-pyrido[2,3-d] pyridazin-5-one.

Compound II is the compound of Formula I where X is nitrogen and Y is carbon, $R^1$ is 4-pyridylmethyl, $R^3$ is chloro, $R^2$, $R^4$, $R^5$ and $R^6$ are hydrogen, namely 6-(4-pyridylmethyl)-8-(3-chlorophenyl)-pyrido[2,3-d] pyridazin-5-one.

Example 55

Determination of Immunosuppressive Activity Utilizing The Hemolytic Plaque Forming Cell Assay This procedure is a modification of "The agar plaque technique for recognizing antibody producing cells," a procedure initially described by Jerne, et al. [*Cell-bound Antibodies*, Amos and Kaprowski editors (Wistar Institute Press, Philadelphia, 1963) p. 109].

Groups of 5–6 adult C3H female mice were sensitized with $1.25 \times 10^8$ sheep red blood cells (SRBC) and simultaneously treated with an oral dosage form of the test material in an aqueous vehicle. Animals in a control group receive the same volume of vehicle. Four days after SRBC inoculation, spleens are dispersed in glass homogenizers. The number of nucleated cells (WBC) is determined and the spleen cell suspension is mixed with SRBC, guinea pig complement and agar solution at 0.5% concentration. Aliquots of the above mixture (0.1 ml) are dropped on four separate quadrants of a Petri dish and are covered with cover slips. After two hours incubation at 37° C., areas of hemolysis around plaque-forming cells (PFC) are counted with a dissecting microscope. Total WBC/spleen, PFC/spleen and PFC/$10^6$WBC (PPM) are calculated for each mouse spleen. Geometric means of each treatment group are then compared with the vehicle-treated control group.

The compounds of the present invention show immunosuppressive activity when tested by this method.

Immunosuppressive Activity of Compounds I and II

|  | Immune PFC |
| --- | --- |
|  | $ED_{50}$ |
| Compound I | 1 mg/kg |
| Compound II | 3 mg/kg |

Example 56

Determination of Immunosuppressive Activity Utilizing Responses of Human Peripheral Blood Lymphocytes to Mitogen This procedure is a modification of a procedure initially described by Greaves, et al. ["Activation of human T and B lymphocytes by polyclonal mitogens," Nature, 248, 698–701 (1974)].

Human mononuclear cells (PBL) are separated from heparinized whole blood by density gradient centrifugation in Ficoll-Paque (Pharmacia). After washing, $5 \times 10^4$ cells/well are cultured in microtiter plates with minimal essential media supplemented with 1% human serum, gentamicin, sodium bicarbonate, 2-mercaptoethanol, glutamine, nonessential amino acids, and sodium pyruvate. The mitogen concanavalin A (Sigma) is used at a concentration of 2 µg/ml. Test materials are tested at concentrations between $10^{-4}$ and $10^{-10}$M, by addition to the culture at time 0. Cultures are set up in quadruplicate and incubated at 37° C. in a humidified atmosphere with 5% $CO_2$ for 48 hours. A pulse of 1.0 µCi/well of $^3$H-thymidine is added for the last 4 hours. Cells are collected on glass fiber filters with an automatic harvester and radioactivity is measured by standard scintillation procedures. The 50% inhibitory concentration ("$IC_{50}$") for mitogenic stimulation is determined graphically. The compounds of the present invention show immunosuppressive activity when tested by this method.

EFFECT OF COMPOUNDS ON MITOGENIC RESPONSE OF HUMAN PBL TO CONCANAVALIN IN A STIMULATION

| | % Suppression | |
| --- | --- | --- |
| Concentration | Compound I | Compound II |
| 100 µM | 100 | 100 |
| 10 µM | 85 | 87 |
| 1 µM | 80 | 83 |
| 0.1 µM | 83 | 74 |

The % suppression represents test well counts minus background (wells with no concanavalin A) divided by controll well counts (wells with no compound) minus background times 100.

Example 57

Determination of Anti-Inflammatory Activity Utilizing Arachidonic Acid-Induced Ear Edema in the Mouse This procedure is a modification of a procedure described by Young et al., *J. Invest. Derm.*, 82:367–371 (1984).

Female Charles River ICR mice 23–27 grams are administered 0.2 ml of test material. The mice are later challenged with 20 µl of arachidonic acid applied topically to the ear. One hour after challenge the weight of an 8 mm disc is determined. The mean increase in ear plug weight is calculated. Materials with anti-inflammatory activity inhibit the increase in ear plug weight.

Antiinflammatory Activity of Compounds I and II

|  | AAEE $ED_{50}$ |
| --- | --- |
| Compound I | 0.003 mg/kg |
| Compound II | 0.009 mg/kg |

The compounds of the present invention exhibit anti-inflammatory activity when tested by this method.

Example 58

Capsule Formulation

This example illustrates the preparation of a representative pharmaceutical formulation for oral administration containing an active compound of Formula I.

| Ingredients | Quantity (mg/capsule) |
| --- | --- |
| Active compound | 200 |
| lactose, spray-dried | 148 |
| magnesium stearate | 2 |

The above ingredients are mixed and introduced into a hard-shell gelatin capsule.

Example 59

Oral Formulation

This example illustrates the preparation of a representative pharmaceutical formulation containing an active compound of Formula I.

An suspension for oral administration is prepared having the following composition:

| Ingredients | Quantity |
| --- | --- |
| Active compound | 1.0 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Other compounds of Formula I, such as those prepared in accordance with Examples 1–45 can be used as the active compound in the preparation of the orally administrable formulations of this example.

Example 60

Tablet Formulation

This example illustrates the preparation of a representative pharmaceutical formulation containing an active compound of Formula I.

A tablet for oral administration is prepared having the following composition:

| Ingredients | Quantity (mg/tablet) |
| --- | --- |
| Active compound | 400 |
| corn starch | 50 |
| lactose | 145 |
| magnesium stearate | 5 |

The above ingredients are mixed intimately and pressed into single scored tablets.

Other compounds of Formula I, such as those prepared in accordance with Examples 1–45 can be used as the active compound in the preparation of the tablet formulations of this example.

Example 61

Injectable Formulation

This example illustrates the preparation of a representative pharmaceutical formulation containing an active compound of Formula I.

An injectable preparation is prepared having the following composition:

| Ingredients | Quantity |
| --- | --- |
| Active compound | 0.2 g |
| water (distilled, sterile) | q.s. to 20.0 mL |

Other compounds of Formula I, such as those prepared in accordance with Examples 1–45 can be used as the active compound in the preparation of the injection administrable formulations of this example.

Example 62

Suppository Formulation

This example illustrates the preparation of a representative pharmaceutical formulation containing an active compound of Formula I.

A suppository totalling 2.5 grams is prepared having the following composition:

| Ingredients | Quantity |
| --- | --- |
| Active compound | 500 mg |
| Witepsol H-15* | q.s. to 2.5 g |

*(triglycerides of saturated vegatable fatty acid; a product of Riches-Nelson, Inc., New York, N.Y.).

Other compounds of Formula I, such as those prepared in accordance with Examples 1–45 can be used as the active compound in the preparation of the suppository formulations of this example.

Other compounds of Formula I, such as those prepared in accordance with Examples 1–45 can be used as the active compound in the preparation of the injection administrable formulations of this example.

| TOXICOLOGY | |
| --- | --- |
| SPECIES: | mice |
| COMPOUND: | compounds I, II |
| DOSAGE: | 3 to 25 mg/kg/day |
| DURATION OF DOSING: | 2 weeks |
| CONCLUSION: | no mortality occurred at any of the dose levels tested. |

The Ames test (in vitro Salmonella mutagenicity assay) was negative.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of the formula:

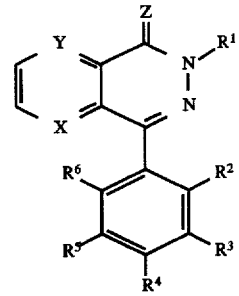

wherein:

X is nitrogen and Y is carbon, or X is carbon and Y is nitrogen;

Z is oxygen or sulfur;

$R^1$ is hydrogen, lower alkyl, cycloalkyl, cycloalkyl lower alkyl, aryl, aralkyl, heterocyclo lower alkyl (where the heterocyclo is selected from pyrrolidinyl, piperidinyl, N-methylpiperidinyl, or morpholinyl, or heteroaryl lower alkyl (where the heteroaryl is selected from 2-pyridyl, 3-pyridyl, 4-pyridyl, the N-oxides thereof, 2-thienyl, or 3-thienyl, each optionally substituted with halo or lower alkyl);

$R^2$, $R^3$, $R^4$, $R^5$ and $R^6$ are independently selected from hydrogen, lower alkyl, halo, carboxy, alkoxycarbonyl, carbamoyl, lower alkyl carbonyl, halocarbonyl, thiomethyl, trifluoromethyl, cyano or nitro;

or a pharmaceutically acceptable salt thereof.

2. The compound of claim 1 wherein X is nitrogen and Y is carbon.

3. The compound of claim 2 wherein $R^1$ is hydrogen.

4. The compound of claim 2 wherein $R^1$ is aralkyl.

5. The compound of claim 2 wherein $R^1$ is heterocyclo lower alkyl or heteroaryl lower alkyl.

6. The compound of claim 2 wherein $R^1$ is lower alkyl or cycloalkyl lower alkyl.

7. The compound of claim 2 wherein $R^2$, $R^4$, $R^5$ and $R^6$ are hydrogen and $R^3$ is chloro.

8. The compound of claim 7 wherein $R^1$ is hydrogen.

9. The compound of claim 7 wherein $R^1$ is aralkyl.

10. The compound of claim 7 wherein $R^1$ is benzyl.

11. The compound of claim 7 wherein $R^1$ is heterocyclo lower alkyl or heteroaryl lower alkyl.

12. The compound of claim 11 wherein $R^1$ is 4-pyridylmethyl.

13. The compound of claim 11 wherein $R^1$ is 3-pyridylmethyl.

14. The compound of claim 11 wherein $R^1$ is 3-thienylmethyl.

15. The compound of claim 7 wherein $R^1$ is lower alkyl or cycloalkyl lower alkyl.

16. The compound of claim 15 wherein $R^1$ is cyclopentylmethyl.

17. The compound of claim 15 wherein $R^1$ is 2-propyl.

18. The compound of claim 2 wherein $R^2$, $R^4$, $R^5$ and $R^6$ are hydrogen and $R^3$ is nitro.

19. The compound of claim 18 wherein $R^1$ is hydrogen.

20. The compound of claim 18 wherein $R^1$ is cyclopropylmethyl.

21. The compound of claim 18 wherein $R^1$ is aralkyl.

22. The compound of claim 21 wherein $R^1$ is benzyl.

23. The compound of claim 18 wherein $R^1$ is heterocyclo lower alkyl or heteroaryl lower alkyl.

24. The compound of claim 23 wherein $R^1$ is 4-pyridylmethyl.

25. The compound of claim 23 wherein $R^1$ is 3-pyridylmethyl.

26. The compound of claim 23 wherein $R^1$ is 3-thienylmethyl.

27. The compound of claim 18 wherein $R^1$ is lower alkyl or cycloalkyl lower alkyl.

28. The compound of claim 27 wherein $R^1$ is ethyl.

29. The compound of claim 2 wherein $R^2$, $R^3$, $R^4$, $R^5$ and $R^6$ are hydrogen.

30. The compound of claim 29 wherein $R^1$ is hydrogen.

31. The compound of claim 29 wherein $R^1$ is aralkyl.

32. The compound of claim 29 wherein $R^1$ is heterocyclo lower alkyl or heteroaryl lower alkyl.

33. The compound of claim 29 wherein $R^1$ is lower alkyl or cycloalkyl lower alkyl.

34. The compound of claim 1 wherein X is carbon and Y is nitrogen.

35. The compound of claim 34 wherein $R^1$ is hydrogen.

36. The compound of claim 34 wherein $R^1$ is aralkyl.

37. The compound of claim 34 wherein $R^1$ is heterocyclo lower alkyl or heteroaryl lower alkyl.

38. The compound of claim 34 wherein $R^1$ is lower alkyl.

39. The compound of claim 34 wherein $R^2$, $R^4$, $R^5$ and $R^6$ are hydrogen and $R^3$ is chloro.

40. The compound of claim 34 wherein $R^2$, $R^4$, $R^5$ and $R^6$ are hydrogen and $R^3$ is nitro.

41. The compound of claim 34 wherein $R^2$, $R^3$, $R^4$, $R^5$ and $R^6$ are hydrogen.

42. A compound of the formula:

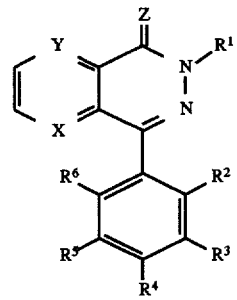

wherein:

X is nitrogen;

Y is carbon;

Z is oxygen or sulfur;

$R^1$ is hydrogen, lower alkyl, cycloalkyl, cycloalkyl lower alkyl, aryl, aralkyl, heterocyclo lower alkyl where the heterocyclo is selected from pyrrolidinyl, piperidinyl, N-methylpiperidinyl, or morpholinyl, or heteroaryl lower alkyl (where the heteroaryl is selected from 2-pyridyl, 3-pyridyl, 4-pyridyl, the N-oxides thereof, 2-thienyl, or 3-thienyl, each optionally substituted with halo or lower alkyl);

two adjacent members of $R^2$, $R^3$, $R^4$, $R^5$ and $R^6$ taken together are methylenedioxy, and the remaining members are hydrogen;

or a pharmaceutically acceptable salt thereof.

43. A pharmaceutical composition comprising a pharmaceutically acceptable excipient and a therapeutically effective amount of a compound of the formula:

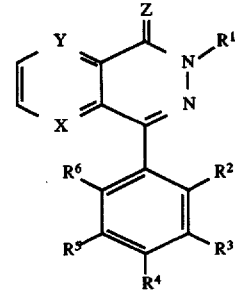

wherein:

X is nitrogen and Y is carbon, or X is carbon and Y is nitrogen;

Z is oxygen or sulfur;

$R^1$ is hydrogen, lower alkyl, cycloalkyl, cycloalkyl lower alkyl, aryl, aralkyl, heterocyclo lower alkyl (where the heterocyclo is selected from pyrrolidinyl, piperidinyl, N-methylpiperidinyl, or morpholinyl, or heteroaryl lower alkyl (where the heteroaryl is selected from 2-pyridyl, 3-pyridyl, 4-pyridyl, the N-oxides thereof, 2-thienyl, or 3-thienyl, each optionally substituted with halo or lower alkyl);

$R^2$, $R^3$, $R^4$, $R^5$ and $R^6$ are independently selected from hydrogen, lower alkyl, halo, carbonyl, halocarbonyl, carbamoyl, lower alkyl carbonyl, halocarbonyl, thiomethyl, triflaoromethyl, cyano or nitro;

or a pharmaceutically acceptable salt thereof.

44. A method of treating a disease state selcted from asthma and inflammation in a meal, comprising administering to a mammal in need thereof a therapeutically effective amount of a compound of the formula:

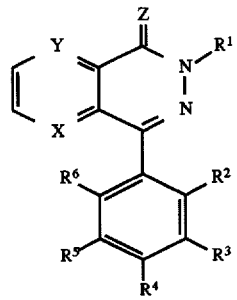

wherein:

X is nitrogen and Y is carbon, or X is carbon and Y is nitrogen;

Z is oxygen or sulfur;

$R^1$ is hydrogen, lower alkyl, cycloalkyl, cycloalkyl lower alkyl, aryl, aralkyl, heterocyclo lower atkyl (where the heterocyclo is selected from pyrrolidinyl, piperidinyl, N-methylpiperidinyl, or morpholinyl), or heteroaryl lower alkyl (where the heteroaryl is selected from 2-pyridyl, 3-pyridyl, 4-pyridyl, the N-oxides thereof, 2-thienyl, or 3-thienyl, each optionally substituted with halo or lower alkyl);

$R^2$, $R^3$, $R^4$, $R^5$ and $R^6$ are independently selected from hydrogen, lower alkyl, halo, carboxy, alkoxycarbonyl, carbamoyl, lower alkyl carbonyl, halocarbonyl, thiomethyl, trifluoromethyl, cyano or nitro;

or a pharmaceutically acceptable salt thereof.

45. The method of claim 44 where the disease state is asthma.

* * * * *

UNITED STATES PATENT AND TRADEMARK OFFICE
CERTIFICATE OF CORRECTION

PATENT NO. : 5,716,954
DATED : Feb. 10, 1998
INVENTOR(S) : Wilhelm et al.

It is certified that error appears in the above-indentified patent and that said Letters Patent is hereby corrected as shown below:

Claim 43, at column 80, line 67, after "halo"
 insert --carboxy, alkoxycarbonyl, carbamoyl, lower alkyl--.

Claim 44, at column 81, line 4, change "selcted" to --selected--.

Claim 44, at column 81, line 5, change "meal" to --mammal--.

Claim 44, at column 82, line 6, change "atkyl" to --alkyl--.

Signed and Sealed this

Twenty-eighth Day of July, 1998

Attest:

BRUCE LEHMAN

Attesting Officer  Commissioner of Patents and Trademarks